US010584180B2

(12) United States Patent
Gruber

(10) Patent No.: US 10,584,180 B2
(45) Date of Patent: Mar. 10, 2020

(54) ANTI-AGE ANTIBODIES FOR TREATING INFLAMMATION AND AUTO-IMMUNE DISORDERS

(71) Applicant: Siwa Corporation, Chicago, IL (US)

(72) Inventor: Lewis S. Gruber, Chicago, IL (US)

(73) Assignee: Siwa Corporation, Chicago, IL (US)

( * ) Notice: Subject to any disclaimer, the term of this patent is extended or adjusted under 35 U.S.C. 154(b) by 0 days.

(21) Appl. No.: 15/511,731

(22) PCT Filed: Sep. 15, 2015

(86) PCT No.: PCT/US2015/050154
§ 371 (c)(1),
(2) Date: Mar. 16, 2017

(87) PCT Pub. No.: WO2016/044252
PCT Pub. Date: Mar. 24, 2016

(65) Prior Publication Data
US 2017/0247472 A1  Aug. 31, 2017

Related U.S. Application Data

(60) Provisional application No. 62/053,018, filed on Sep. 19, 2014.

(51) Int. Cl.
*A61K 39/00* (2006.01)
*C07K 16/44* (2006.01)
*C07K 16/24* (2006.01)

(52) U.S. Cl.
CPC ............ *C07K 16/44* (2013.01); *C07K 16/241* (2013.01); *A61K 2039/505* (2013.01); *A61K 2039/507* (2013.01); *C07K 2317/21* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,217,344 A | 8/1980 | Vanlerberghe et al. | |
| 4,900,747 A | 2/1990 | Vlassara et al. | |
| 4,911,928 A | 3/1990 | Wallach | |
| 4,917,951 A | 4/1990 | Wallach | |
| 4,965,288 A | 10/1990 | Palfreyman | |
| 5,494,791 A | 2/1996 | Cohen | |
| 5,518,720 A | 5/1996 | Cohen | |
| 5,601,526 A | 2/1997 | Chapelon et al. | |
| 5,620,479 A | 4/1997 | Diederich | |
| 5,664,570 A | 9/1997 | Bishop | |
| 5,693,762 A | 12/1997 | Queen et al. | |
| 5,702,704 A | 12/1997 | Bucala | |
| 5,766,590 A | 6/1998 | Founds et al. | |
| 5,811,075 A | 9/1998 | Vlassara et al. | |
| 5,817,771 A | 10/1998 | Bayley et al. | |
| 5,984,882 A | 11/1999 | Rosenschein et al. | |
| 6,067,859 A | 5/2000 | Kas et al. | |
| 6,090,382 A | 7/2000 | Salfeld et al. | |
| 6,176,842 B1 | 1/2001 | Tachibana et al. | |
| 6,245,318 B1 | 6/2001 | Klibanov et al. | |
| 6,309,355 B1 | 10/2001 | Cain et al. | |
| 6,380,165 B1 | 4/2002 | Al-Abed et al. | |
| 6,387,373 B1 | 5/2002 | Wright et al. | |
| 6,670,136 B2 | 12/2003 | Schmidt et al. | |
| 6,676,963 B1 | 1/2004 | Lanza et al. | |
| 6,818,215 B2 | 11/2004 | Smith et al. | |
| 6,821,274 B2 | 11/2004 | McHale et al. | |
| 7,033,574 B1 | 4/2006 | Schneider et al. | |
| 7,101,838 B2 | 9/2006 | Stern et al. | |
| 7,256,273 B2 | 8/2007 | Basi et al. | |
| 7,347,855 B2 | 3/2008 | Eshel et al. | |
| 7,358,226 B2 | 4/2008 | Dayton et al. | |
| 7,367,988 B1 | 5/2008 | Litovitz | |
| 7,751,057 B2 | 7/2010 | Oldenburg et al. | |
| 7,815,570 B2 | 10/2010 | Eshel et al. | |
| 8,323,651 B2 | 12/2012 | Gu et al. | |
| 8,343,420 B2 | 1/2013 | Cioanta et al. | |
| 8,398,977 B2 | 3/2013 | Bleck et al. | |
| 8,721,571 B2 | 5/2014 | Gruber | |
| 9,161,810 B2 | 10/2015 | Gruber | |
| 9,320,919 B2 | 4/2016 | Gruber | |
| 9,649,376 B2 | 5/2017 | Gruber | |
| 9,993,535 B2 | 6/2018 | Gruber | |
| 10,226,531 B2 | 3/2019 | Gruber | |
| 2002/0193784 A1 | 12/2002 | McHale et al. | |

(Continued)

FOREIGN PATENT DOCUMENTS

AU  2009/248945  5/2014
DE  102008009461  8/2009

(Continued)

OTHER PUBLICATIONS

Baker et al., Nature 479:232-236 (Year: 2011).*
Lloyd et al. Protein Engineering, Design & Selection 2009, 22:159-168 (Year: 2009).*
Edwards et al., J Mol Biol. Nov. 14, 2003;334(1):103-118 (Year: 2003).*
R133, 4 pages, Aug. 8, 2017, 2015114990, RU.
R134, 12 pages, Aug. 23, 2017, 11776932.3, EP.
R135, 25 pages, Sep. 22, 2017, U.S. Appl. No. 14/974,095, US.
U.S. Appl. No. 15/720,912, filed Sep. 29, 2017.
R1, 6 pages, Jun. 14, 2012, U.S. Appl. No. 12/994,421, US.
R2, 19 pages, Jul. 21, 2009, PCT/US2009/44951, WO.
R3, 6 pages, Dec. 2, 2010, PCT/US2009/44951, WO.
R4, 13 pages, Apr. 26, 2012, PCT/US2011/053399, WO.

(Continued)

Primary Examiner — Daniel C Gamett
(74) Attorney, Agent, or Firm — Evan Law Group LLC

(57) ABSTRACT

A composition for treating inflammation or auto-immune disorders comprises (i) an antibody that binds to an AGE-modified protein on a cell, and (ii) an anti-inflammation antibody. Furthermore, the antibody that binds to an AGE-modified protein on a cell is also effective to treat inflammation or auto-immune disorders alone.

29 Claims, 1 Drawing Sheet
Specification includes a Sequence Listing.

(56) References Cited

U.S. PATENT DOCUMENTS

| | | |
|---|---|---|
| 2003/0073138 A1 | 4/2003 | Kientsch-Engel et al. |
| 2003/0170173 A1 | 9/2003 | Klaveness et al. |
| 2003/0229283 A1 | 12/2003 | Craig et al. |
| 2004/0039416 A1 | 2/2004 | Myhr |
| 2004/0141922 A1 | 7/2004 | Klaveness et al. |
| 2004/0208826 A1 | 10/2004 | Schneider et al. |
| 2004/0229830 A1 | 11/2004 | Tachibana et al. |
| 2005/0084538 A1 | 4/2005 | Dayton et al. |
| 2005/0283098 A1 | 12/2005 | Conston et al. |
| 2006/0078501 A1 | 4/2006 | Goertz et al. |
| 2006/0122543 A1 | 6/2006 | Mayer et al. |
| 2006/0188883 A1 | 8/2006 | Murray et al. |
| 2007/0059247 A1 | 3/2007 | Lindner et al. |
| 2007/0065415 A1 | 3/2007 | Kleinsek et al. |
| 2007/0065443 A1 | 3/2007 | Tobia |
| 2007/0078290 A1 | 4/2007 | Esenaliev |
| 2007/0083120 A1 | 4/2007 | Cain et al. |
| 2007/0128117 A1 | 6/2007 | Bettinger et al. |
| 2007/0129633 A1 | 6/2007 | Lee et al. |
| 2007/0225242 A1 | 9/2007 | Erler |
| 2008/0019986 A1 | 1/2008 | Stern et al. |
| 2008/0051680 A1 | 2/2008 | Luebcke |
| 2008/0063603 A1 | 3/2008 | Schneider et al. |
| 2008/0139942 A1 | 6/2008 | Gaud et al. |
| 2008/0160506 A1 | 7/2008 | Liu et al. |
| 2009/0022659 A1 | 1/2009 | Olson et al. |
| 2009/0076390 A1 | 3/2009 | Lee et al. |
| 2009/0306552 A1 | 12/2009 | Furuzono et al. |
| 2010/0028359 A1 | 2/2010 | Gu et al. |
| 2010/0226932 A1 | 9/2010 | Smith et al. |
| 2011/0105961 A1 | 5/2011 | Gruber |
| 2011/0319499 A1 | 12/2011 | Semba et al. |
| 2012/0130287 A1 | 5/2012 | Gruber |
| 2012/0156134 A1 | 6/2012 | Squires |
| 2012/0183534 A1 | 7/2012 | Gruber |
| 2013/0131006 A1 | 5/2013 | Lee et al. |
| 2013/0243785 A1 | 9/2013 | Gruber |
| 2014/0303526 A1 | 10/2014 | Gruber |
| 2016/0101299 A1 | 4/2016 | Gruber |
| 2016/0152697 A1 | 6/2016 | Gruber |
| 2016/0175413 A1 | 6/2016 | Gruber |
| 2016/0215043 A1 | 7/2016 | Gruber |
| 2016/0339019 A1 | 11/2016 | Laberge et al. |
| 2017/0216435 A1 | 8/2017 | Gruber |
| 2018/0044411 A1 | 2/2018 | Gruber |
| 2018/0111982 A2 | 4/2018 | Gruber |
| 2018/0298087 A1 | 10/2018 | Gruber |
| 2018/0312577 A1 | 11/2018 | Gruber |
| 2018/0326026 A1 | 11/2018 | Gruber |
| 2019/0031781 A1 | 1/2019 | Gruber |
| 2019/0119371 A1 | 4/2019 | Gruber |
| 2019/0328873 A1 | 10/2019 | Gruber |
| 2019/0328876 A1 | 10/2019 | Gruber |

FOREIGN PATENT DOCUMENTS

| | | |
|---|---|---|
| EP | 0 259 893 | 3/1988 |
| EP | 1 415 997 | 5/2004 |
| EP | 1 867 659 | 12/2007 |
| JP | 09178740 | 7/1997 |
| JP | 11246599 | 9/1999 |
| JP | 2003/160599 | 6/2003 |
| JP | 2006-249015 | 9/2006 |
| WO | 1996/20958 | 7/1996 |
| WO | 1997/49429 | 12/1997 |
| WO | 1999/07893 | 2/1999 |
| WO | 1999/14587 | 3/1999 |
| WO | 1999/64463 | 12/1999 |
| WO | 2000/20458 | 4/2000 |
| WO | 2004/011460 | 2/2004 |
| WO | 2004/016229 | 2/2004 |
| WO | 2004/076677 | 9/2004 |
| WO | 2006/012415 | 2/2006 |
| WO | 2006/017647 | 2/2006 |
| WO | 2006/040597 | 4/2006 |
| WO | 2009/136382 | 11/2009 |
| WO | 2009/143411 | 11/2009 |
| WO | 2010/005531 | 1/2010 |
| WO | 2012/047629 | 4/2012 |
| WO | 2012/071269 | 5/2012 |
| WO | 2012/135616 | 10/2012 |
| WO | 2013/009785 | 1/2013 |
| WO | 2013/043161 | 3/2013 |
| WO | 2013/070468 | 5/2013 |
| WO | 2014/136114 | 9/2014 |
| WO | 2015/112835 | 7/2015 |
| WO | 2015/116740 | 8/2015 |
| WO | 2016/044252 | 3/2016 |
| WO | 2017/065837 | 4/2017 |
| WO | 2017/181116 | 10/2017 |
| WO | 2018/204679 | 11/2018 |

OTHER PUBLICATIONS

R5, 3 pages, Jul. 2, 2012, U.S. Appl. No. 12/951,768, US.
R6, 21 pages, Mar. 30, 2012, U.S. Appl. No. 12/951,768, US.
R7, 12 pages, Jun. 13, 2012, PCT/US2011/061387, WO.
R8, 13 pages, Jun. 27, 2012, PCT/US12/31446, WO.
R9, 5 pages, May 14, 2012, 200980118817.6, CN.
R10, 9 pages, Nov. 8, 2011, 09 751 639.7, EP.
R11, 6 pages, Jun. 12, 2012, 09 751 639.7, EP.
R12, 3 pages, Jul. 20, 2012, U.S. Appl. No. 12/994,421, US.
R13, 4 pages, Jul. 13, 2012, 10-2012-7026063, KR.
R14, 27 pages, Sep. 10, 2012, U.S. Appl. No. 12/994,421, US.
R15, 9 pages, Nov. 5, 2012, U.S. Appl. No. 12/951,768, US.
R16, 4 pages, Nov. 8, 2012, 2009248945, AU.
R17, 4 pages, Aug. 20, 2012, 209513, IL.
R18, 6 pages, Jan. 3, 2013, 09 751 639.7, EP.
R19, 10 pages, Feb. 26, 2013, U.S. Appl. No. 12/994,421, US.
R20, 5 pages, Dec. 25, 2012, 2010152693, RU.
R21, 3 pages, Mar. 21, 2013, U.S. Appl. No. 12/951,768, US.
R22, 5 pages, Feb. 28, 2013, 200980118817.6, CN.
R23, 10 pages, Feb. 28, 2013, 10-2010-7026063, KR.
R24, 3 pages, Mar. 27, 2013, U.S. Appl. No. 12/951,768, US.
R25, 3 pages, Apr. 15, 2013, 2009248945, AU.
R26, 3 pages, May 21, 2013, U.S. Appl. No. 12/994,421, US.
R27, 9 pages, Apr. 23, 2013, 2010152693, RU.
R28, 7 pages, May 30, 2013, PCT/US2011/061387, WO.
R29, 3 pages, May 22, 2013, 209513, IL.
R30, 3 pages, Jul. 18, 2013, U.S. Appl. No. 12/994,421, US.
R31, 5 pages, Jul. 26, 2013, 09751639.7, EP.
R32, 7 pages, Apr. 2, 2013, 11776932.3, WO.
R33, 4 pages, Jul. 16, 2013, 2010/012473, MX.
R34, 14 pages, Jul. 29, 2013, U.S. Appl. No. 12/951,768, US.
R35, 5 pages, Sep. 30, 2013, 10-2010-7026063, KR.
R36, 3 pages, Nov. 15, 2013, U.S. Appl. No. 12/951,768, US.
R37, 6 pages, Oct. 10, 2013, PCT/US2012/031446, WO.
R38, 8 pages, Nov. 19, 2013, 2011-511734, JP.
R39, 8 pages, Oct. 10, 2013, 200980118817.6, CN.
R40, 15 pages, Dec. 20, 2013, U.S. Appl. No. 12/951,768, US.
R41, 7 pages, Dec. 23, 2013, 10-2010-7026063, KR.
R42, 6 pages, Jan. 23, 2014, 09751639.7, EP.
R43, 3 pages, Feb. 4, 2014, 2009248945, AU.
R44, 11 pages, Mar. 18, 2014, 2010/012473, MX.
R45, 5 pages, May 7, 2014, 200980118817.6, CN.
R46, 3 pages, May 25, 2014, 209513, IL.
R47, 7 pages, May 26, 2014, 2010152693, RU.
R48, 3 pages, Jun. 17, 2014, 2010/012473, MX.
R49, 3 pages, Jun. 20, 2014, 2,724,886, CA.
R50, 8 pages, Jun. 22, 2014, 10-2013-7028228, KR.
R51, 3 pages, Jul. 29, 2014, 10-2010-7026063, KR.
R52, 9 pages, Jul. 29, 2014, 10-2012-7026483, KR.
R53, 6 pages, Sep. 3, 2014, U.S. Appl. No. 13/332,976, US.
R54, 30 pages, Sep. 9, 2014, U.S. Appl. No. 14/247,081, US.
R55, 6 pages, Sep. 12, 2014, 14170802.4, EP.
R56, 7 pages, Oct. 8, 2014, 200980118817.6, CN.
R57, 51 pages, Nov. 18, 2014, U.S. Appl. No. 13/332,976, US.
R58, 34 pages, Nov. 18, 2014, U.S. Appl. No. 12/994,421, US.
R59, 3 pages, Dec. 2, 2014, 209513, IL.

(56) References Cited

OTHER PUBLICATIONS

R60, 8 pages, Dec. 3, 2014, 2011-511734, JP.
R61, 3 pages, Jan. 13, 2015, U.S. Appl. No. 14/247,081, US.
R62, 5 pages, Feb. 2, 2015, U.S. Appl. No. 14/247,081, US.
R63, 10 pages, Dec. 16, 2014, 2010152693, RU.
R64, 3 pages, Feb. 5, 2015, 2,724,886, CA.
R65, 6 pages, Feb. 27, 2015, 10-2012-7026483, KR.
R66, 5 pages, Mar. 13, 2015, U.S. Appl. No. 12/994,421, US.
R67, 6 pages, Mar. 13, 2015, U.S. Appl. No. 13/332,976, US.
R68, 44 pages, Mar. 27, 2015, U.S. Appl. No. 12/994,421, US.
R69, 25 pages, Apr. 1, 2015, U.S. Appl. No. 13/332,976, US.
R70, 4 pages, Mar. 26, 2015, 200980118817.6, CN.
R71, 3 pages, Apr. 23, 2015, U.S. Appl. No. 13/332,976, US.
R72, 3 pages, May 1, 2015, U.S. Appl. No. 13/332,976, US.
R73, 4 pages, Apr. 27, 2015, 10-2013-7028228, KR.
R74, 29 pages, May 6, 2015, U.S. Appl. No. 14/247,081, US.
R75, 7 pages, Apr. 20, 2015, 10-2015-7007520, KR.
R76, 18 pages, Jun. 11, 2015, U.S. Appl. No. 13/332,976, US.
R77, 3 pages, Jul. 10, 2015, U.S. Appl. No. 14/247,081, US.
R78, 11 pages, Jul. 21, 2015, U.S. Appl. No. 14/278,081, US.
R79, 8 pages, Jun. 22, 2015, 2015-076575, JP.
R80, 3 pages, Jun. 5, 2015, 2011332143, AU.
R81, 3 pages, Jun. 22, 2015, 2014202548, AU.
R82, 5 pages, Jul. 17, 2015, 14170802.4, EP.
R83, 54 pages, Sep. 10, 2015, U.S. Appl. No. 13/876,157, US.
R84, 4 pages, Sep. 2, 2015, U.S. Appl. No. 12/994,421, US.
R85, 5 pages, Sep. 8, 2015, 2,724,886, CA.
R86, 7 pages, Jul. 27, 2015, MX/a/2013/013310, MX.
R87, 4 pages, Nov. 27, 2015, 10-2015-7007520, KR.
R88, 5 pages, Dec. 10, 2015, 14170802.4, EP.
R89, 3 pages, Jan. 8, 2016, 2014202548, AU.
R90, 2 pages, Jan. 11, 2016, 2011332143, AU.
R91, 7 pages, Jan. 12, 2016, 2015-076575, JP.
R92, 35 pages, Jan. 19, 2016, U.S. Appl. No. 12/994,421, US.
R93, 2 pages, Jan. 25, 2016, 2011332143, AU.
R94, 8 pages, Mar. 30, 2016, U.S. Appl. No. 13/876,157, US.
R95, 17 pages, Mar. 31, 2016, PCT/US2015/050154, WO.
R96, 7 pages, Apr. 6, 2016, MX/a/2013/013310, MX.
R97, 5 pages, Apr. 14, 2016, 2,724,886, CA.
R98, 8 pages, Apr. 28, 2016, 2014202548, AU.
R99, 5 pages, Jun. 20, 2016, 2014202548, AU.
R100, 13 pages, Jun. 15, 2016, 201510303227.8, CN.
R101, 4 pages, Aug. 24, 2016, 2016204196, AU.
R102, 4 pages, Apr. 14, 2016, 240242, IL.
R103, 8 pages, Jul. 19, 2016, 2016-098558, JP.
R104, 9 pages, Jul. 13, 2016, 2015114990, RU.
R105, 15 pages, Oct. 17, 2016, U.S. Appl. No. 13/876,157, US.
R106, 5 pages, Oct. 26, 2016, 2,818,647, CA.
R107, 6 pages, Sep. 22, 2016, U.S. Appl. No. 14/974,095, US.
R108, 16 pages, Dec. 30, 2016, 201510303227.8, CN.
R109, 8 pages, Dec. 29, 2016, 4875/KOLNP/2010, IN.
R110, 9 pages, Jan. 5, 2017, U.S. Appl. No. 13/876,157, US.
R111, 16 pages, Dec. 2, 2016, PCT/US2016/039076, WO.
R112, 16 pages, Aug. 10, 2016, PCT/US2016/034880, WO.
R113, 8 pages, Feb. 21, 2017, 16198527.0, EP.
R114, 6 pages, Mar. 23, 2017, 11776932.3, EP.
R115, 4 pages, Feb. 20, 2017, 2,724,886, CA.
R116, 1 page, May 1, 2017, 2,724,886, CA.
R117, 4 pages, Jan. 23, 2017, 240242, IL.
R118, 9 pages, Dec. 19, 2016, 2016-098558, JP.
R119, 9 pages, Feb. 15, 2017, MX/a/2013/013310, MX.
R120, 6 pages, Mar. 23, 2017, 11776932.3, EP.
R121, 6 pages, Jan. 27, 2017, 2015114990, RU.
R122, 4 pages, Apr. 19, 2017, 2,818,647, CA.
R123, 45 pages, Feb. 13, 2017, U.S. Appl. No. 14/974,095, US.
R124, 20 pages, May 17, 2017, PCT/US2017/018185, WO.
R125, 16 pages, Aug. 10, 2016, PCT/US2016/034880, WO.
R126, 8 pages, Jun. 13, 2017, U.S. Appl. No. 14/974,561, US.
R127, 10 pages, Mar. 30, 2017, PCT/US2015/050154, WO.
R128, 5 pages, Jun. 27, 2017, U.S. Appl. No. 14/974,095, US.
R129, 2 pages, Nov. 24, 2016, 14170802.4, EP.
R130, 3 pages, May 10, 2017, 2017113349, RU.
R131, 14 pages, May 15, 2017, 201510303227.8, CN.
R132, 5 pages, May 29, 2017, 248652, IL.
U.S. Appl. No. 14/932,200, filed Nov. 4, 2015.
U.S. Appl. No. 15/489,624, filed Apr. 17, 2017.
U.S. Appl. No. 14/920,737, filed Oct. 22, 2015.
U.S. Appl. No. 14/974,561, filed Dec. 18, 2015.
U.S. Appl. No. 14/974,095, filed Dec. 18, 2015.
International Search Report and Written Opinion dated Sep. 29, 2017 for PCT application No. PCT/US2017/027773.
Capparelli, C. et al., "Autophagy and senescence in cancer-associated fibroblasts metabolically supports tumor growth and metastasis via glycolysis and ketone production", Cell Cycle, vol. 11, No. 12, pp. 2285-2302, (2012).
""Shelf life" of blood? Shorter than we think", Johns Hopkins Medicine, pp. 1-2 found at www.hopkinsmedicine.org/news/media/releases/shelf_life_of_blood_shorter_than_we_think, (2013).
Garay-Sevilla, M.E. et al., "Advanced glycosylation end products in skin, serum, saliva and urine and its association with complications of patients with Type 2 diabetes mellitus", Journal of Endocrinological Investigation, vol. 28, No. 5, pp. 223-230, (2005).
Joyal, S.V., "Aging and Glycation", Life Extension Magazine, issue 4, pp. 1-7, found at www.lifeextension.com/Magazine/2008/4/Aging-And-Glycation/Page-01, (2008).
Egberts, J-H. et al., "Anti-tumor necrosis factor therapy inhibits pancreatic tumor growth and metastasis", Cancer Research, vol. 68, pp. 1443-1450, (2008).
Lowe, R. et al., "Buccals are likely to be a more informative surrogate tissue than blood for epigenome-wide association studies", Epigenetics, vol. 8, No. 4, pp. 445-454, (2013).
Bian, C. et al., "Clinical outcome and expression of mutant P53, P16, and Smad4 in lung adenocarcinoma: a prospective study", World Journal of Surgical Oncology, vol. 13, No. 128, pp. 1-8, (2015).
Tape, C.J. et al., "Oncogenic KRAS regulates tumor cell signaling via stromal reciprocation", Cell, vol. 165, pp. 910-920, (2016).
Product description for "CD8+CD57+ T Cell Isolation Kit, human", Miltenyi Biotec, pp. 1-4, found at www.miltenyibiotec.com/en/products-and-services/macs-cell-separation/cell-separation-reagents/t-cells/cd8-cd57-t-cell-isolation-kit-human.aspx, printed on Aug. 16, 2017.
Warrington, K.J. et al., "CD28 loss in senescent CD4$^+$ T cells: reversal by interleukin-12 stimulation", Blood, vol. 101, No. 9, pp. 3543-3549, (2003).
Kared, H. et al., "CD57 in human natural killer cells and T-lymphocytes", Cancer Immunology, Immunotherapy, vol. 65, issue 4, pp. 441-452, (2016).
Li, Z. et al., "Cdkn2a suppresses metastasis in squamous cell carcinomas induced by the gain-of-function mutant $p53^{R172H}$", The Journal of Pathology, vol. 240, issue 2, pp. 224-234, (2016). (Abstract Only).
Demaria, M. et al., "Cellular senescence promotes adverse effects of chemotherapy and cancer relapse", Cancer Discovery, vol. 7, pp. 165-176, (2017).
Niu, L. et al., "Free and protein-bound $N^\varepsilon$-carboxymethyllysine and $N^\varepsilon$-carboxyethyllysine in fish muscle: Biological variation and effects of heat treatment", Journal of Food Composition and Analysis, vol. 57, pp. 56-63, (2017).
Yoon, M-S. et al., "Characterisation of advanced glycation endproducts in saliva from patients with diabetes mellitus", Biochemical and Biophysical Research Communications, vol. 323, issue 2, pp. 377-381, (2004).
Product description for "Carboxymethyl Lysine (CML) ELISA", Kamiya Biomedical Company, pp. 1-7, found at www.k-assay.com/pdf/KT-32428.pdf, printed on Aug. 16, 2017.
Baar, M.P. et al., "Targeted apoptosis of senescent cells restores tissue homeostasis in response to chemotoxicity and aging", Cell, vol. 169, pp. 132-147, (2017).
Kim, Y.H. et al., "Senescent tumor cells lead the collective invasion in thyroid cancer", Nature Communications, pp. 1-14, (2017).
Ciccone, T.G. et al., "Reversing OA—new treatment on the horizon", Practical Pain Management, pp. 1-5, found at www.

(56) References Cited

OTHER PUBLICATIONS practicalpainmanagement.com/resources/news-and-research/reversing-oa-new-treatment-horizon, printed on Aug. 17, 2017.
Cook, L.S., "Learning about blood component therapy", Nursing, vol. 39, No. 4, pp. 30-33, (2009).
Landesberg, R. et al., "The expression of the receptor for glycation endproducts (RAGE) in oral squamous cell carcinomas", Oral Surgery Oral Medicine Oral Pathology Oral Radiology, vol. 105, issue 5, pp. 617-624, (2008).
Zhou, H.W., "Recovery of function in osteoarthritic chondrocytes induced by $p16^{INK4a}$-specific siRNA in vitro", Rheumatology, vol. 43, pp. 555-568, (2004).
Fuijkschot, W.W. et al., "Prevention of age-induced N(ε)-(carboxymethyl)lysine accumulation in the microvasculature", European Journal of Clinical Investigation, vol. 46, issue 4, pp. 334-341, (2016). (Abstract Only).
Rasheed, Z.A. et al., "Pathology of pancreatic stroma in PDAC", Pancreatic Cancer and Tumor Microenvironment, pp. 1-10, (2012).
Morton, J.P. et al., "Mutant p53 drives metastasis and overcomes growth arrest/senescence in pancreatic cancer", PNAS, vol. 107, No. 1, pp. 246-251, (2010).
Verzijl, N. et al., "AGEing and osteoarthritis: a different perspective", Current Opinion in Rheumatology, vol. 15, issue 5, pp. 616-622, (2003).
Frescas, D. et al., "Senescent cells expose and secrete an oxidized form of membrane-bound vimentin as revealed by a natural polyreactive antibody", PNAS, vol. 114, No. 9, pp. E1668-E1677, (2017).
Oren, M. et al., "Mutant p53 gain-of-function in cancer", Cold Spring Harbor Perspectives in Biology, vol. 2, pp. 1-15, (2010).
"Senescence promotes chemotherapy side effects and cancer relapse", Medical Xpress, pp. 1-4, found at https://m.medicalxpress.com/news/2017-01-senescence-chemotherapy-side-effects-cancer.html, (2017).
Oh, J. et al., "Local clearance of senescent cells attenuates the development of post-traumatic osteoarthritis and creates a pro-regenerative environment", Nature Medicine, vol. 23, No. 6, pp. 1-9, (2017).
Protocols for "Isolation of untouched human T cells from peripheral blood mononuclear cells (PBMC)", Thermo Fisher Scientific, pp. 1-4, found at www.thermofisher.com/us/en/home/references/protocols/proteins-expression-isolation-and-analysis/cell-separation-methods/human-cell-separation-protocols/isolation-of-untouched-human-t-cells-.html, printed on Aug. 17, 2017.
Henrich, C.J. et al., "Isolation and characterization of a glycopeptide from human senescent erythrocytes", Carbohydrate Research, vol. 120, pp. 55-66, (1983).
Yang, S. et al., "Impact of oxidative stress biomarkers and carboxymethyllysine (an advanced glycation end product) on prostate cancer: A prospective study", Clinical Genitourinary Cancer, vol. 13, No. 5, pp. 1-14, (2015).
Tsai, K.K.C. et al., "Low-dose radiation-induced senescent stromal fibroblasts render nearby breast cancer cells radioresistant", Radiation Research, vol. 172, pp. 306-313, (2009).
Nie, H et al., "Impaired glial glutamate uptake induces extrasynaptic glutamate spillover in the spinal sensory synapses of neuropathic rats", Journal of Neurophysiology, vol. 103, pp. 2570-2580, (2010).
Garcia-Matas, S. et al., "Dysfunction of astrocytes in senescence-accelerated mice SAMP8 reduces their neuroprotective capacity", Aging Cell, vol. 7, pp. 630-640, (2008).
Danysz, W. et al., "Alzheimer's disease, β-amyloid, glutamate, NMDA receptors and memantine-searching for the connections", British Journal of Pharmacology, vol. 167, pp. 324-352, (2012).
Blasko, I. et al., "Glial cells: Astrocytes and oligodendrocytes during normal brain aging", Encyclopedia of Neuroscience, pp. 743-747, (2009).
Leonard, B.W. et al., "Subventricular zone neural progenitors from rapid brain autopsies of elderly subjects with and without neurodegenerative disease", The Journal of Comparative Neurology, vol. 515, pp. 269-294, (2009).

Louveau, A. et al., "Structural and functional features of central nervous system lymphatic vessels", Nature, vol. 523, issue 7560, pp. 337-341, (2015).
Torgan, C., "Lymphatic vessels discovered in central nervous system", NIH Research Matters, pp. 1-4, found at www.nih.gov/news-events/nih-research-matters/lymphatic-vessels-discovered-central-nervous-system, Jun. 15, 2015.
Boskovitz, A. et al., "Monoclonal antibodies for brain tumour treatment", Expert Opinion on Biological Therapy, vol. 4, No. 9, pp. 1453-1471, (2004).
Takami, A. et al., "Treatment of primary central nervous system lymphoma with induction of complement-dependent cytotoxicity by intraventricular administration of autologous-serum-supplemented rituximab", Cancer Science, vol. 97, No. 1, pp. 80-83, (2006).
Biran, A. et al., "Senescent cells communicate via intercellular protein transfer", Genes & Development, vol. 29, pp. 791-802, (2015).
Golde, T.E. et al., "Proteinopathy-induced neuronal senescence: a hypothesis for brain failure in Alzheimer's and other neurodegenerative diseases", Alzheimer's Research & Therapy, vol. 1, No. 2, pp. 1-12, (2009).
Ouroboros, "Sweet madness: Sporadic prion disease and age-related changes in protein glycosylation", Research in the Biology of Aging, pp. 1-4, found at https://ouroboros.wordpress.com/2006/12/14/sweet-madness-sporadic-prion-disease-and-age-related-changes-in-protein-glycosylation/, (2006).
Xellbiogene, "Amyotrophic lateral sclerosis, immunotherapy is offering some hope", Xellbiogene.com, pp. 1-3, (2014).
Definition of "Complement system" printed from Wikipedia, the free encyclopedia on Aug. 4, 2015 found at http://en.wikipedia.org/wiki/Complement_system.
Definition of "Ventricular system" printed from Wikipedia, the free encyclopedia on Oct. 30, 2017 found at http://en.wikipedia.org/wiki/Ventricular_system.
Urushitani, M., "Future perspectives of immunotherapy against ALS", Rinsho Shinkeigaku, vol. 49, No. 11, pp. 818-820, (2009). (Abstract Only).
Cabezas, I.L. et al., "The role of glial cells in Alzheimer disease: potential therapeutic implications", Neurologia, vol. 29, No. 5, pp. 305-309, (2014).
Definition of "Prion" printed from Wikipedia, the free encyclopedia on Nov. 17, 2015 found at http://en.wikipedia.org/wiki/Prion.
"Prion Diseases", National Institute of Allergy and Infectious Diseases, pp. 1-2, found at www.niaid.nih.gov/diseases-conditions/prion-diseases, printed on Oct. 30, 2017.
"Alzheimer basics: Plaques and tangles", ALZ.org, pp. 1-2, found at www.alz.org/norcal/in_my_community_20545.asp, printed on Nov. 17, 2015.
Definition of "Lewy body" printed from Wikipedia, the free encyclopedia on Nov. 17, 2015 found at http://en.wikipedia.org/wiki/Lewy_body.
Definition of "Myocyte" printed from Wikipedia, the free encyclopedia on Nov. 17, 2015 found at http://en.wikipedia.org/wiki/Myocyte.
Definition of "Myosatellite cell" printed from Wikipedia, the free encyclopedia on Nov. 17, 2015 found at http://en.wikipedia.org/wiki/Myosatellite_cell.
Definition of "Microglia" printed from Wikipedia, the free encyclopedia on Oct. 30, 2017 found at http://en.wikipedia.org/wiki/Microglia.
Definition of "Astrocyte" printed from Wikipedia, the free encyclopedia on Oct. 30, 2017 found at http://en.wikipedia.org/wiki/Astrocyte.
Ouroboros, "A role for microglial senescence in Alzheimer's?", Research in the Biology of Aging, pp. 1-3, found at https://ouroboros.wordpress.com/?s=a+role+for+microglial, (2007).
Chen, K.S. et al., "Monoclonal antibody therapy for malignant glioma", Glioma: Immunotherapeutic Approaches, chapter 10, pp. 121-141, (2012).
Reardon, S., "Alzheimer's drug sneaks through blood-brain barrier", Nature News, pp. 1-4, (2014).

(56) References Cited

OTHER PUBLICATIONS

"Astrocytes as a novel target in Alzheimer's disease", Expertsvar, pp. 1-2, (2012).
Myslinski, N., "Alzheimer's disease and the blood-brain barrier", Today's Geriatric Medicine, vol. 7, No. 1, pp. 1-10, (2014).
Hutter-Saunders, J.A.L. et al., "Pathways towards an effective immunotherapy for Parkinson's disease", Expert Reviews in Neurotherapeutics, vol. 11, No. 12, pp. 1703-1715, (2011).
Definition of "Intrathecal administration" printed from Wikipedia, the free encyclopedia on Oct. 30, 2017 found at http://en.wikipedia.org/wiki/Intrathecal_administration.
"What is ALS?", ALSA.org, found at www.alsa.org/2015-non-responsive-pages/about-als/what-is-als.html, printed on Mar. 31, 2016.
Rouger, K. et al., "Systemic delivery of allogenic muscle stem cells induces long-term muscle repair and clinical efficacy in Duchenne muscular dystrophy dogs", The American Journal of Pathology, vol. 179, No. 5, pp. 2501-2518, (2011).
Anderson, J.L. et al., "Brain function in Duchenne muscular dystrophy", Brain, vol. 125, pp. 4-13, (2002).
Jarius, S. et al., "AQP4 antibodies in neuromyelitis optica: diagnostic and pathogenetic relevance", Nature Reviews, vol. 6, pp. 383-392, (2010).
Wesolowski, J. et al., "Single domain antibodies: promising experimental and therapeutic tools in infection and immunity", Medical Microbiology and Immunology, vol. 198, pp. 157-174, (2009).
Definition of "Antibody" printed from Wikipedia, the free encyclopedia on Sep. 21, 2015 found at http://en.wikipedia.org/wiki/Antibody.
Definition of "Antibody-dependent cell-mediated cytotoxicity" printed from Wikipedia, the free encyclopedia on Dec. 28, 2015 found at http://en.wikipedia.org/wiki/Antibody-dependent_cell-mediated_cytotoxicity.
Definition of "Blocking antibody" printed from Wikipedia, the free encyclopedia on Dec. 28, 2015 found at http://en.wikipedia.org/wiki/Blocking_antibody.
Definition of "Fc receptor" printed from Wikipedia, the free encyclopedia on Dec. 28, 2015 found at http://en.wikipedia.org/wiki/Fc_receptor.
Definition of "Fragment crystallizable region" printed from Wikipedia, the free encyclopedia on Dec. 28, 2015 found at http://en.wikipedia.org/wiki/Fragment_crystallizable_region.
Definition of "Neutralizing antibody" printed from Wikipedia, the free encyclopedia on Dec. 28, 2015 found at http://en.wikipedia.org/wiki/Neutralizing_antibody.
Company Information on "NantKwest", pp. 1-4, found at www.nantkwest.com, printed on Apr. 1, 2016.
R136, 16 pages, Sep. 29, 2017, PCT/US2017/027773, WO.
R137, 4 pages, Oct. 13, 2017, 2,818,647, CA.
R138, 14 pages, Oct. 18, 2017, 2015114990, RU.
R139, 67 pages, Nov. 15, 2017, U.S. Appl. No. 14/974,561, US.
R140, 4 pages, Nov. 29, 2017, 2,818,647, CA.
R141, 7 pages, Nov. 30, 2017, U.S. Appl. No. 14/932,200, US.
R142, 3 pages, Jan. 11, 2018, U.S. Appl. No. 14/974,095, US.
R143, 19 pages, Jan. 30, 2018, U.S. Appl. No. 14/974,095, US.
R144, 5 pages, Feb. 8, 2018, U.S. Appl. No. 14/974,561, US.
R145, 81 pages, Feb. 21, 2018, U.S. Appl. No. 14/932,200, US.
R146, 17 pages, Mar. 16, 2018, 11776932.3, EP.
R147, 7 pages, Apr. 30, 2018, 2017-086871, JP.
R148, 4 pages, May 14, 2018, U.S. Appl. No. 14/974,095, US.
R149, 7 pages, May 14, 2018, U.S. Appl. No. 14/920,737, US.
R151, 51 pages, May 21, 2018, U.S. Appl. No. 15/489,624, US.
R152, 12 pages, May 29, 2018, U.S. Appl. No. 14/974,561, US.
R153, 1 page, Jun. 22, 2018, 2,818,647, CA.
R154, 1 page, Jul. 20, 2018, 2,818,647, CA.
U.S. Appl. No. 15/977,587, filed May 11, 2018.
U.S. Appl. No. 15/768,425, filed May 27, 2016.
U.S. Appl. No. 15/863,741, filed Jan. 5, 2018.
U.S. Appl. No. 15/863,784, filed Jan. 5, 2018.
U.S. Appl. No. 15/863,811, filed Jan. 5, 2018.
U.S. Appl. No. 15/863,828, filed Jan. 5, 2018.
U.S. Appl. No. 15/953,244, filed Apr. 13, 2018.
R155, 11 pages, Aug. 30, 2018, PCT/US2017/018185, WO.
R156, 40 pages, Sep. 5, 2018, U.S. Appl. No. 14/932,200, US.
R157, 51 pages, Sep. 12, 2018, U.S. Appl. No. 14/920,737, US.
R158, 7 pages, Sep. 14, 2018, 15772116.8, EP.
R159, 21 pages, Sep. 25, 2018, U.S. Appl. No. 14/974,561, US.
R160, 13 pages, Oct. 23, 2018, U.S. Appl. No. 15/489,624, US.
R161, 8 pages, Oct. 25, 2018, PCT/US2017/027773, WO.
R163, 6 pages, Nov. 28, 2018, U.S. Appl. No. 15/720,912, US.
R164, 9 pages, Dec. 6, 2018, 2017113349, RU.
R165, 10 pages, Dec. 13, 2018, U.S. Appl. No. 14/932,200, US.
R166, 3 pages, Jan. 11, 2019, 17708098.3, EP.
R167, 6 pages, Jan. 23, 2019, U.S. Appl. No. 15/489,624, US.
R168, 5 pages, Feb. 4, 2019, U.S. Appl. No. 15/863,811, US.
R169, 5 pages, Feb. 6, 2019, U.S. Appl. No. 14/974,561, US.
R170, 5 pages, Feb. 11, 2019, U.S. Appl. No. 15/863,784, US.
R172, 12 pages, Mar. 4, 2019, U.S. Appl. No. 14/920,737, US.
R173, 20 pages, Mar. 12, 2019, U.S. Appl. No. 14/974,561, US.
R174, 55 pages, Mar. 26, 2019, U.S. Appl. No. 15/720,912, US.
R175, 13 pages, Apr. 10, 2019, U.S. Appl. No. 15/863,741, US.
R176, 144 pages, Feb. 25, 2019, 17708098.3, EP.
R177, 9 pages, Dec. 25, 2018, PCT/US2016/039076, WO.
R178, 5 pages, Mar. 20, 2019, U.S. Appl. No. 15/863,828, US.
U.S. Appl. No. 16/265,875, filed Feb. 1, 2019.
U.S. Appl. No. 16/092,743, filed Apr. 14, 2017.
U.S. Appl. No. 16/077,713, filed Feb. 16, 2017.
U.S. Appl. No. 16/311,149, filed Dec. 18, 2018.
U.S. Appl. No. 16/228,293, filed Dec. 20, 2018.
U.S. Appl. No. 16/383,348, filed Apr. 12, 2019.
Forbes, J.M. et al., "Below the radar: Advanced glycation end products that detour "around the side"", Clinical Biochemist Reviews, vol. 26, pp. 123-134, (2005).
Paul, W.E., "Fundamental immunology, third edition", Raven Press New York, chapter 9, pp. 292-295, (1993).
Rudikoff, S. et al., "Single amino acid substitution altering antigen-binding specificity", Proceedings of the National Academy of Science USA, vol. 79, pp. 1979-1983, (1982).
Wu, H. et al., "Humanization of a murine monoclonal antibody by simultaneous optimization of framework and CDR residues", Journal of Molecular Biology, vol. 294, pp. 151-162, (1999).
Golay, J. et al., "Mechanism of action of therapeutic monoclonal antibodies: Promises and pitfalls of in vitro and in vivo assays", Archives of Biochemistry and Biophysics, vol. 526, pp. 146-153, (2012).
Tang, S-S. et al., "Reaction of aortic lysyl oxidase with β-Aminopropionitrile", The Journal of Biological Chemistry, vol. 258. No. 7, pp. 4331-4338, (1983).
Saito, H. et al., "Reguiation of a novel gene encoding a lysyl oxidase-related protein in cellular adhesion and senescence", The Journal of Biological Chemistry, vol. 272, No. 13, pp. 8157-8160, (1997).
Choi, Y-G. et al., "Nε-carboxymethyl modification of lysine residues in pathogenic prion isoforms", Molecular Neurobiology, vol. 53, pp. 3102-3112, (2016).
Wendel, U. et al., "A novel monoclonal antibody targeting carboxymethyllysine, an advanced glycation end product in atherosclerosis and pancreatic cancer", PLoS One, vol. 13, No. 2, pp. 1-22, (2018).
Hsia, T-C. et al., "Carboxymethyllysine, an advanced glycation end-product, promotes the invasion and migration of lung cancer A549 cells", Clinical Medicine Research, vol. 6. No. 5, pp. 149-156, (2017).
Nowotny, K. et al., "Advanced glycation end products and oxidative stress in type 2 diabetes mellitus", Biomolecules, vol. 5, pp. 194-222, (2015).
Yun, M.H. et al., "Recurrent turnover of senescent cells during regeneration of a complex structure", eLIFE, elifesciences.org, pp. 1-16, (2015).
Barja, G., "Aging in vertebrates, and the effect of caloric restriction: a mitochondrial free radical production-DNA damage mechanism?", Biological Reviews, vol. 79, No. 2, pp. 235-251, (2004). Abstract Only.

(56) References Cited

OTHER PUBLICATIONS

Pamplona, R. et al., "Aging increases nepsilon-(carboxymethyl)lysine and caloric restriction decreases nepsilon-(carboxyethyl)lysine and nepsilon-(malondialdehyde)lysine in rat heart proteins", Free Radical Research, vol. 36, No. 1, pp. 47-54, (2002). Abstract Only.

Yun, M.H., "Cellular senescence in regeneration", The Node, pp. 1-8, found at http://thenode.biologists.com/cellular-senescence-in-regeneration/research/, Jun. 28, 2015.

Kasper, M. et al., "Age-related changes in cells and tissues due to advanced glycation end products (AGES)", Archives of Gerontology and Geriatrics, vol. 32, issue 3, pp. 233-243, (2001). Abstract Only.

Wang, Z. et al., "Advanced glycation end-producat Nε-carboxymethyl-Lysine accelerates progression of atherosclerotic calcification in diabetes", Atherosclerosis, vol. 221, issue 2, pp. 387-396, (2012). Abstract Only.

Draber, P, et al., "Stability of monoclonal igM antibodies freeze-dried in the presence of trehalose", Journal of Immunological Mehtods, vol. 181, issue 1, pp. 37-43, (1995).

Kesari, S. et al., "Pritumumab binding to glioma cells induces ADCC and inhibits tumor growth", Journal of Clinical Oncology, vol. 35, No. 15, Supplemental, e14004-e14004, (2017). Abstract Only.

Babic, I. et al., "Pritumumab, the first therapeutic antibody for glioma patients", Human Antibodies, vol. 26, No. 2, pp. 95-101, (2017). Abstract Only.

Riva, P. et al., "Treatment of intracranial human glioblastoma by direct intratumoral administration of 131I-labelled anti-tenascin monoclonal antibody BC-2", International Journal of Cancer, vol. 51, No. 1, pp. 7-13, (1992). Abstract Only.

Ruster, M. et al., "Detection of elevated Nε-carboxymethyllysine levels in muscular tissue and in serum of patients with fibromyalgia", Scandinavian Journal of Rheumatology, vol. 34, issue 6, pp. 460-463, (2005). Abstract Only.

Niwa, H. et al., "Accelerated formation of Nε-(carboxymethyl) lysine, an advanced glycation end product, by glyoxal and 3-deoxygiucosone in cultured rat sensory neurons", Biochemical and Biophysical Research Communications, vol. 248, issue 1, pp. 93-97, (1998). Abstract Only.

Daly, C. et al., "Monocyte chemoattractant protein-1 (CCL2) in inflammatory disease and adaptive immunity: Therapeutic opportunities and controversies", Microcirculation, vol. 10, pp. 247-257, (2003).

Lee, S.T. et al., "Decreased number and function of endothelial progenitor cells in patients with migraine", Neurology, vol. 70, No. 17, pp. 1510-1517, (2008). Abstract Only.

Brown, J.N, et al., "Class effect of erythropoietin therapy on hemoglobin A1C in a patient with diabetes mellitus and chronic kidney disease not undergoing hemodialysis", Pharmacotherapy, The Journal of Human Pharmacology and Drug Therapy, vol. 29, No. 4, pp. 468-472, (2009). Abstract Only.

Liu, J. et al., "Accelerated senescence of renal tubular epithelial cells is associated with disease progression of patients with immunoglobulin A (IgA) nephropathy", Translational Research, vol. 159, issue 6, pp. 454-463, (2012). Abstract Only.

Khaw, K-T. et al., "Association hemoglobin A1c with cardiovascular disease and mortality in adults: The European prospective investigation into cancer in Norfolk", Annals of Internal Medicine, vol. 141, pp. 413-420, (2004).

Kohnert, K.D. et al., "Destruction of pancreatic beta cells in rats by complete Freund's adjuvant combined with non-diabetogenic doses of streptozotocin", Diabetes Research, vol. 5, No. 1, pp. 1-11, (1987). Abstract Only.

Staud, R., "Fibromyalgia pain: do we know the source?", Current Opinion in Rheumatology, vol. 16, issue 2, pp. 157-163, (2004), Abstract Only.

Fleurence, J. et al., "Targeting and killing glioblastoma with monoclonal antibody to O-acetyl GD2 ganglioside", Oncotarget, vol. 7, No. 27, pp. 41172-41185, (2016).

Velarde, M.C. et al., "Senescent cells and their secretory phenotype as targets for cancer therapy", Interdisciplinary Topics in Gerontology, vol. 38, pp. 17-27, (2013).

Wang, Z. et al., "CML/RAGE signal induces calcification cascade in diabetes", Diabetology & Metabolic Syndrome, vol. 8. No. 83, pp. 1-12, (2016).

Freise, A.C. et al., "In vivo imaging with antibodies and engineered fragments", Molecular Immunology, vol. 67, issue 2, pp. 142-152, (2015).

Pavlides, S. et al., "The reverse Warburg effect: Aerobic glycolysis in cancer associated fibroblasts and the tumor stroma", Cell Cycle, vol. 8, No. 23, pp. 3984-4001, (2009).

Dunn, G.P. et al., "Principles of immunology and its nuances in the central nervous system", Neuro-Oncology, vol. 17, pp. vii3-vii8, (2015).

Rettig, M,P, et al., "Evaluation of biochemical changes during in vivo erythrocyte senescence in the dog", Blood, vol. 93, No. 1, pp. 376-384, (1999).

Baraibar, M.A. et al., "Proteomic quantification and identification of carbonylated proteins upon oxidative stress and during cellular aging", Journal of Proteomics, vol. 92, pp. 63-70, (2013) Abstract Only.

Chaudhuri, J. et al., "A Caenorhabditis elegans model elucidates as a conserved role for TRPA1-Nrf signaling in reactive α-dicarbonyl detoxification", Current Biology, vol. 26, pp. 3014-3025, (2016).

Saleh, T. et al., "Reversibility of chemotherapy-induced senescence is independent of autophagy and a potential model for tumor dormancy and cancer recurrence", bioRxiv, pp. 1-29, 5 figures, (2017).

Hubert, P. et al., "Antibody-dependent cell cytotoxicity in monoclonal antibody-mediated tumor immunotherapy", OncoImmunology, vol. 1, issue 1, pp. 103-105, (2012).

Ouchi, R. et al., "Senescence from glioma stem cell differentiation promotes tumor growth", Biochemical and Biophysical Research Communications, vol. 470, No. 2, pp. 275-281, (2016).

Evans, A. et al., "Differentiating benign from malignant solid breast masses: value of shear wave elastography according to lesion stiffness combined with greyscale ultrasound according to BI-RADS classification", British Journal of Cancer, vol. 107, pp. 224-229, (2012).

Walen, K.H., "Normal human cell conversion to 3-D cancer-like growth: Genome damage, endopolyploidy, senescence escape, and cell polarity change/loss", Journal of Cancer Therapy, vol. 2, pp. 181-189, (2011).

Virella, G. et al., "Development of capture assays for different modifications of human low-density lipoprotein", Clinical and Diagnostic Laboratory Immunology, vol. 12, No. 1, pp. 68-75, (2005).

Moghaddam, A.E. et al., "Reactive carbonyls are a major Th2-inducing damage associated molecular pattern generated by oxidative stress", The Journal of Immunology, vol. 187, 1626-1633, (2011).

Kuilman. T. et al., "The essence of senescence", Genes & Development, vol. 24, pp. 2463-2479, (2010).

James, E.L. et al., "Senescent human fibroblasts show increased glycolysis and redox homeostasis with extracellular metabolomes that overlap with those of irreparable DNA damage, aging, and disease", Journal of Proteome Research, vol. 14, pp. 1854-1871, (2015).

Hein, G. et al., "Are advanced glycation end-product-modified proteins of pathogenetic importance in fibromyalgia?" Rheumatology, vol. 41, pp. 1163-1167, (2002).

Beausejour, C.M. et al., "Reversal of human cellular senescence: roles of the p53 and p16 pathways", The EMBO Journal, vol. 22, No. 16, pp. 4212-4222, (2003).

Simpson, R.J., "Aging, persistent viral infections, and immunosenescence: Can exercise "make space"?", Exercise and Sport Sciences Reviews, vol. 39, No. 1, pp. 23-33, (2011).

Gudkov, A., "Andrei Gudkov taped an expanded presentation of the slides he presented at 2017 Biology of Aging conference at Scripps, Florida Jan. 22-27", Everon Biosciences, found at everonbio.com/Andrei-gudkov-taped-an-expanded-presentation-of-the-slides-he-

(56) References Cited

OTHER PUBLICATIONS presented-at 2017-biology-of-aging-conference-at-scripps-florida-22-27-january, 2 pages, Mar. 21, 2017. Abstract Only.
Radoi, V. et al., "Advanced glycation end products in diabetes mellitus: Mechanism of action and focused treatment", Proceedings of the Romanian Academy, Series B, vol. 1, pp. 9-19, (2012).
Sieben, C.J. et al., "Two-step senescence-focused cancer therapies", Trends in Cell Biology, pp. 1-15, (2018).
Gaens, K.H.J. et al., "Nε-(carboxymethyl)lysine-receptor for advanced glycation end product axis is a key modulator of obesity-induced dysregulation of adipokine expression and insulin resistance", Arteriosclerosis, Thrombosis, and Vascular Biology, vol. 34, issue 6, pp. 1199-1208, pp. s1-s9, (2014).
Semba, R.D. et al., "Relationship of an advanced glycation end product, plasma carboxymethyl-lysine, with slow walking speed in older adults: the inCHIANTI study", European Journal of Applied Physiology, vol. 108, No. 1, pp. 191-195, (2010).
Wu, J. et al., "Sonoporation, anti-cancer drug and antibody delivery using ultrasound", Ultrasonics, vol. 44, supplement, pp. e21-e25, (2006). Abstract Only.
Meerwaldt, R. et al., "Skin autofluorescence is a strong predictor of cardiac mortality in diabetes", Diabetes Care, vol. 30, No. 1, pp. 107-112, (2007).
Nagai, R. et al., "Antibody-based detection of advanced glycation end-products: promises vs. limitations", Glyooconjugate Journal, vol. 33, No. 4, pp. 545-552, (2016).
Schmidt, A.M. et al., "The biology of the receptor for advanced glycation end products and its ligands", Biochimica et Biophysica Acta, vol. 1498, pp. 99-111, (2000).
Berens, M.E. et al., ""... those left behind." Biology and oncology of invasive glioma cells", Neoplasia, vol. 1, No. 3, pp. 208-219, (1999).
Hansen, K. et al., "Microneedle enabled intradermal delivery of biologics", 3M Drug Delivery Systems, 1 page, printed on Jul. 25, 2018.
Ikeda, K. et al., "Immunochemical approaches to AGE-structures: characterization of anti-AGE antibodies", Journal of Immunological Methods, vol. 215, No. 1-2, pp. 95-104, (1998).
De Vriese, A.S. et al., "Inhibition of the interaction of AGE-RAGE prevents hyperglycemia-induced fibrosis of the peritoneal membrane", Journal of the American Society of Nephrology, vol. 14, pp. 2109-2118, (2003).
Ott, C. et al., "Role of advanced glycation end products in cellular signaling", Redox Biology, vol. 2, pp. 411-429, (2014).
International Search Report and Written Opinion dated Aug. 7, 2018 for PCT application No. PCT/US2018/027653.
International Search Report and Written Opinion dated Sep. 10, 2018 for PCT application No. PCT/US2018/030931.
Edwards, B.M. et al., "The remarkable flexibility of the human antibody repertoire; Isolation of over one thousand different antibodies to a single protein, BLyS", The Journal of Molecular Biology, vol. 334, pp. 103-118, (2003).
Lloyd, C. et al., "Modelling the human immune response: performance of a $10^{11}$ human antibody repertoire against a broad panel of therapeutically relevant antigens", Protein Engineering, Design & Selection, vol. 22, No. 3, pp. 159-168, (2009).
Ansari, N.A. et al., "Glycated lysine residues: A marker for non-enzymatic protein glycation in age-related diseases", Disease Markers, vol. 30, pp. 317-324, (2011).
Blagosklonny, M.V. et al., "Cancer and aging", Cell Cycle, vol. 7, No. 17, pp. 2615-2618, (2008).
Chow, H-M. et al., "Senescent neurons in the alzheimer's brain kill nearby healthy neurons by blocking their WNT lifeline: The continuing saga of the zombie apocalypse", Alzheimer's & Dementia, vol. 12, No. 7(S), p. P658, (2016).
Dvorakova, E. et al., "Development of monoclonal antibodies specific for glycated prion protein", Journal of Toxicology and Environmental Health, Part A, vol. 74, pp. 1469-1475, (2011).
Search Results for "Carboxy Methyl Lysine Anitbody", 7 pages, antibodies-online.com, (2018).
Awwad, S. et al., "Overview of antibody drug delivery", Pharmaceutics, vol. 10, No. 83, pp. 1-24, (2018).
Farr, J.N. et al., "Targeting cellular senescence prevents age-related bone loss in mice", Nature Medicine, vol. 23, No. 9, pp. 1072-1079, (2017).
Hoenicke, L. et al., "Immune surveillance of senescent cells—biological significance in cancer-and non-cancer pathologies", Carcinogenesis, vol. 33, No. 6, pp. 1123-1126, (2012).
Kemmler, W. et al., "Prevalence of sarcopenia in Germany and the corresponding effect of osteoarthritis in females 70 years and older living in the community: results of the FORMoSA study", Clinical Interventions in Aging, vol. 10, pp. 1565-1573, (2015).
Myrianthopoulos, V. et al., "Senescence and senotherapeutics: a new field in cancer therapy", Pharmacology & Therapeutics, vol. 193, pp. 31-49, (2019).
Salahuddin, P. et al., "The role of advanced glycation end products in various types of neurodegenerative disease: A therapeutic approach", Cellular & Molecular Biology Letters, vol. 19, pp. 407-437, (2014).
Schosserer, M. et al., "The dual role of cellular senescence in developing tumors and their response to cancer therapy", Frontiers in Oncology, vol. 7, article 278, pp. 1-13, (2017).
Bussian, T.J. et al., "Clearance of senescent glial cells prevents tau-dependent pathology and cognitive decline", Nature Letters, vol. 562, pp. 578-582, (2018).
Penney, J. et al., "Senescence mediates neurodegeneration", Nature, vol. 562, pp. 503-504, (2018).
Trivedi, P.M. et al., "Repurposed JAK1/JAK2 inhibitor reverses established autoimmune insulitis in NOD mice", Diabetes, vol. 66, p. 1650-1660, (2017).
Wang, C. et al., "DNA damage response and cellular senescence in tissues of aging mice", Aging Cell, vol. 8, pp. 311-323, (2009).
Iizuka, K. et al., "Dasatinib improves insulin sensitivity and affects lipid metabolism in a patient with chronic myeloid leukaemia", BMJ Case Rep, pp. 1-3, (2016).
Jeon, O.H. et al., "Local clearance of senescent cells attenuates the development of posttraumatic osteoarthritis and creates a pro-regenerative environment", Nature Medicine, vol. 23, pp. 775-781, (2017). Abstract Only.
Duke Health News & Media, "Duke team finds missing immune cells that could fight lethal brain tumors", Duke University School of Medicine, pp. 1-5, (2018).
Apple, S., "An old idea, revived: Starve cancer to death", NYTimes.com, pp. 1-15, (2016).
Dock, J.N. et al., "Role of CD8 T cell replicative senescence in human aging and in HIV-mediated immunosenescence", Aging and Disease, vol. 2, No. 5, pp. 382-397, (2011).
Rayavarapu, S. et al., "Idiopathic inflammatory myopathies: pathogenic mechanisms of muscle weakness", Skeletal Muscle, vol. 3, No. 13, pp. 1-13, (2013).
Kudryashova, E. et al., "Satellite cell senescence underlies myopathy in a mouse model of limb-girdle muscular dystrophy 2H", The Journal of Clinical Investigation, vol. 122, No. 5, pp. 1764-1776, (2012).
Ratelade, J. et al., "Neuromyelitis optica IgG and natural killer cells produce NMO lesions in mice without myelin loss", Acta Neuropathologica, vol. 123, issue 6, pp. 861-872, (2012).
Vincent, T. et al., "Functional consequences of neuromyelitis optica-IgG astrocyte interactions on blood-brain barrier permeability and granulocyte recruitment", The Journal of Immunology, vol. 181, pp. 5730-5737, (2008).
Baarine, M. et al., "ABCD1 deletion-induced mitochondrial dysfunction is corrected by SAHA: implication for adrenoleukodystrophy", Journal of Neurochemistry, vol. 133, pp. 380-396, (2015).
Durieu, I. et al., "Subepithelial fibrosis and degradation of the bronchial extracellular matrix in cystic fibrosis", American Journal of Respiratory and Critical Care Medicine, vol. 158, No. 2, pp. 580-588, (1998).
Shapiro, B.L. et al., "Premature senescence in cultured skin fibroblasts from subjects with cystic fibrosis", Science, vol. 203, issue 4386, pp. 1251-1253, (1979). Abstract Only.

(56) References Cited

OTHER PUBLICATIONS

Fischer, B.M. et al., "Increased expression of senescence markers in cystic fibrosis airways", American Journal of Physiology Lung Cellular and Molecular Physiology, vol. 304, No. 6, pp. L394-L400, (2013).

Thom, M. et al., "An investigation of the expression of $G_1$-phase cell cycle proteins in focal cortical dysplasia type IIB", Journal of Neuropathology and Experimental Neurology, vol. 66, No. 11, pp. 1045-1055, (2007).

Valdivieso, A.G. et al., "CFTR activity and mitochondrial function", Redox Biology, vol. 1, pp. 190-202, (2013).

Chilosi, M. et al., "Premature lung aging and cellular senescence in the pathogenesis of idiopathic pulmonary fibrosis and COPD/emphysema", Translational Research, vol. 162, issue 3, pp. 156-173, (2013). Abstract Only.

Ribeiro, C.M.P., "The role of intracellular calcium signals in inflammatory responses of polarized cystic fibrosis human airway epithelia", Drugs in R&D, vol. 7, issue 1, pp. 17-31, (2006), Abstract Only.

Velisek L. et al., "Aging: effects of aging on seizures and epilepsy", Encyclopedia of Basic Epilepsy Research, pp. 37-40, (2009). Abstract Only.

Muller, S. et al., "Analysis of senescence markers in rodent pancreatic stellate cells", The Pancreapedia, pp. 1-8, (2013).

Lim, M., "Acute immunology, temporal lobe epilepsy and other disorders", YoungEpilepsy.Org, pp. 1-70, found at http://youngepilepsy.org.uk/dmdocuments/MIND-THE-GAP2015_Ming%20Lim.pdf, (2015).

Definition of "Cachexia" printed from Wikipedia, the free encyclopedia on Dec. 28, 2015 found at http://en.wikipedia.org/wiki/Cachexia.

Lok, C., "The last illness, researchers are gaining insight into the causes of Cachexia—a devastating form of muscle wasting that is often the final stage of cancer and other diseases", Nature, vol. 528, pp. 182-183, (2015).

da Rocha, O.M. et al., "Sarcopenia in rheumatoid cachexia: definition, mechanisms, clinical consequences and potential therapies", Revista Brasileira de Reumatologia, vol. 49, No. 3, pp. 294-301, (2009).

Tisdale, M.J., "Biology of Cachexia", Journal of the National Cancer Institute, vol. 89, No. 23, pp. 1763-1773, (1997).

Romanick, M. et al., "Murine models of atrophy, cachexia, and sarcopenia in skeletal muscle", Biochimica et Biophysics Acta—Molecular Basis of Disease, vol. 1832, issue 9, pp. 1410-1420, (2013).

Ali, S. et al., "Sarcopenia, cachexia and aging: Diagnosis, mechanisms and therapeutic options", Gerontology, vol. 60, No. 4, pp. 294-305, (2014).

Angelini, P.D. et al., "Constitutive HER2 signaling promotes breast cancer metastasis through cellular senescence", Cancer Research, vol. 73, No. 1, pp. 450-458, (2013).

Arai, Y. et al., "Inflammation, but not telomere length, predicts successful ageing at extreme old age: A longitudinal study of semi-supercentenarians", EBioMedicine, vol. 2, pp. 1549-1558, (2015).

Bedard, N. et al., "Inactivation of the ubiquitin-specific protease 19 deubiquitinating enzyme protects against muscle wasting", The FASEB Journal, vol. 29, No. 9, pp. 3889-3898, (2016).

Figueroa-Clarevega, A. et al., "Malignant *Drosophila* tumors interrupt insulin signaling to induce cachexia-like wasting", Developmental Cell, vol. 33, pp. 47-55, (2015).

Giacconi, R. et al., "Cellular senescence and inflammatory burden as determinants of mortality in elderly people until the extreme old age", EBioMedicine, vol. 2, pp. 1316-1317, (2015).

Jin, H. et al., "Protein modifications as potential biomarkers in breast cancer", Biomarker Insights, vol. 4, pp. 191-200, (2009).

Lee, S-J. et al., "Treating cancer cachexia to treat cancer", Skeletal Muscle, vol. 1, No. 2, pp. 1-5, (2011).

Mohamed, M.M. et al., "Human monocytes augment invasiveness and proteolytic activity of inflammatory breast cancer", Biological Chemistry, vol. 389, No. 8, pp. 1117-1121, (2008).

Pare, R. et al., "The significance of the senescence pathway in breast cancer progression", Journal of Clinical Pathology, vol. 66, pp. 491-495, (2013). Abstract Only.

Pinto, N.I. et al., "Cancer as a proinflammatory environment Metastasis and cachexia", Mediators of Inflammation, vol. 2015, pp. 1-13, (2015).

Tchkonia, T. et al., "Cellular senescence and the senescent secretory phenotype: therapeutic opportunities", The Journal of Clinical Investigation, vol. 123, No. 3, pp. 966-972, (2013).

Tesarova, P. et al.—"Carbonyl and oxidative stress in patients with breast cancer—is there a relation to the stage of the disease?", Neoplasma, vol. 54, No. 3, pp. 219-224, (2007).

Tseng, Y-C., et al., "Preclinical investigation of the novel histone deacetylase inhibitor AR-42 in the treatment of cancer-induced cachexia", Journal of the National Cancer Institute, vol. 107, No. 12, pp. 1-14, (2015).

Wang, S. et al., "Characterization of IGFBP-3, PAI-1 and SPARC mRNA expression in senescent fibroblasts", Mechanisms of Ageing and Development, vol. 92, issues 2-3, pp. 121-132, (1996). Abstract Only.

Yang, S. et al., "Impact of oxidative stress biomarkers and carboxymethyllysine (an advanced glycation end product) on prostate cancer: A prospective study", Clinical Genitourinary Cancer, vol. 13, issue 5, pp. e347-e351, (2015).

"Global Arthritis Research Network: $4^{th}$ World Congress on Arthritis in Montreal", Arthritis Research & Therapy, vol. 6, supplement 3, meeting abstracts, pp. S1-S41, Sep. 20-22, 2004.

Miller, R.E. et al., "Osteoarthritis joint pain: The cytokine connection", Cytokine, vol. 70, No. 2, pp. 185-193, (2014).

LifeExtension, "Chronic Pain", Lifeextension.com, pp. 1-18, found at www.lifeextension.com/protocols/health-concerns/chronic-pain/page-03, (2016).

Rush University Medical Center, "Scientists home in on cause of osteoarthritis pain". Science Daily, found at www.sciencedaily.com/releases/2012/12/121227173053.htm, pp. 1-4, (2012).

Kidd, B.L. et al., "Mechanisms of inflammatory pain", British Journal of Anesthesia, vol. 87, No. 1, pp. 3-11, (2001).

Price, J.S. et al., "The role of chondrocyte senescence in osteoarthritis", Aging Cell, vol. 1, pp. 57-65, (2002).

Morales, T.I., "Chondrocyte moves: clever strategies?", OsteoArthritis and Cartilage, vol. 15, pp. 861-871, (2007).

Martin, J.A. et al., "Effects of oxidative damage and telomerase activity on human articular cartilage chondrocyte senescence", Journal of Gerontology: Biological Sciences, vol. 59A, No. 4, pp. 324-337, (2004).

Ang, D.C. et al., "MCP-1 and IL-8 as pain biomarkers in fibromyalgia: A pilot study", Pain Medicine, vol. 12, pp. 1154-1161, (2011).

Burton, D.G.A. et al., "Microarray analysis of senescent vascular smooth muscle cells: A link to atherosclerosis and vascular calcification", Experimental Gerontology, vol. 44, issue 10, pp. 659-665, (2009).

Konttinen, Y.T. et al., "Chondrocyte-mediated collagenolysis correlates with cartilage destruction grades in osteoarthritis", Clinical and Experimental Rheumatology, vol. 23, pp. 19-26, (2005).

"Low back pain", U.S. Department of Health and Human Services, Public Health Service National Institutes of Health, 1-28, (2014).

Bicer, F. "CCL2 (MCP-1) mediates chronic pelvic pain through mast cells in experimental autoimmune cystitis", ETD Archive, pp. 1-120, (2012).

Loeser, R.F. "Aging and osteoarthritis: The role of chondrocyte senescence and aging changes in the cartilage matrix", Osteoarthritis and Cartilage, vol. 17, No. 8, pp. 971-979, (2009).

Zhou, H-W. et al., "Expressions of p16INK4a in healthy and osteoarthritic human articular cartilage and difference analysis", Research Gate, pp. 2148-2149, found at www.researchgate.net/publication/290275008_Expressions_of_p16INK4a_in_healthy_and_osteoarthritic_human_articular_cartilage_and_difference_analysis, (2004). Abstract Only.

(56) References Cited

OTHER PUBLICATIONS

Martin, J.A. et al., "Post-traumatic osteoarthritis: the role of accelerated chondrocyte senescence", Biorheology, vol. 41, pp. 479-491, (2004).
Martin, J.A. et al., "Human chondrocyte senescence and osteoarthritis", Biorheology, vol. 39, No. 1,2, pp. 145-152, (2002). Abstract Only.
Forliti, M., "Mayo clinic researchers link senescent cells to most common form of arthritis", Mayo Clinic, pp. 1-2, found at www.eurekalert.org/pub_releases/2016-08/mc-mcr081016.php, (2016).
Roubenoff, R., "Sarcopenic obesity: Does muscle loss cause fat gain? Lessons from Rheumatoid arthritis and osteoarthritis", Annals of the New York Academy of Sciences, vol. 904, pp. 553-557, (2000). Abstract Only.
De Ceuninck, F. et al., "Bearing arms against osteoarthritis and sarcopenia: When cartilage and skeletal muscle find common interest in talking together", Drug Discovery Today, vol. 19, issue 3, pp. 305-311, (2014). Abstract Only.
Chatterjea, D. "Mast cells and pain", Mastcell Basophil, pp. 1-5, found at www.mastcell-basophil.net/wiki/wiki-start/mast-cells-and-pain/, (2013).
Bach, B. "New drug promises relief for inflammatory pain, scientists say", News Center, Stanford Medicine PASiN, found at med.stanford.edu/news/all-news/2014/08/new-drug-promises-relief-for-inflammatory-pain-scientists-say.html, 3 pages, (2014).
Daly, C. et al., "Monocyte chemoattractant protein-1 (CCL2) in inflammatory disease and adaptive immunity: Therapeutic opportunities and controversies", Microcirculation, vol. 10, issue 3-4, pp. 247-257, (2003).
"MMP13 gene", NIH U.S. National Library of Medicine, found at ghr.nlm.nih.gov/gene/MMP13, 4 pages, (2016).
Hayami, T. et al., "MMP-1 (Collagenase-1) and MMP-13 (Collagenase-3) differentially regulate markers of osteoblastic differentiation in osteogenic cells", Matrix Biology, vol. 27, issue 8, pp. 682-692, (2008).
Attur, M.G. et al., "Autocrine production of IL-1 beta by human osteoarthritis-affected cartilage and differential regulation of endogenous nitric oxide, IL-6, prostaglandin E2, and IL-8", Proceedings of the Association of American Physicians, vol. 110, No. 1, pp. 65-72, (1998). Abstract Only.
Xu, Y-K. et al., "The role of MCP-1-CCR2 ligand-receptor axis in chondrocyte degradation and disease progress in knee osteoarthritis", Biological Research, vol. 48, No. 64, pp. 1-8, (2015).
Goldring, M.B., "The role of the chondrocyte in osteoarthritis", Arthritis & Rheumatism, vol. 43, No. 9, pp. 1916-1926, (2000).
Mobasheri, A. et al., "Chondrocyte and mesenchymal stem cell-based therapies for cartilage repair in osteoarthritis and related orthopaedic conditions", Maturitas, vol. 78, pp. 188-198, (2014).
"What are chondrocytes?", wiseGeek, found at www.wisegeek.org/what-are-chondrocytes.htm, 1 page, printed on Nov. 29, 2016.
Woolf, A.D. et al., "Burden of major musculoskeletal conditions", Bulletin of the World Health Organization, vol. 81, No. 9, pp. 646-656, (2003).
Pereira, D. et al., "The effect of osteoarthritis definition on prevalence and incidence estimates: a systematic review", Osteoarthritis and Cartilage, vol. 19, pp. 1270-1285, (2011).
Martin, J.A. et al., "Aging, articular cartilage chondrocyte senescence and osteoarthritis", Biogerontology, vol. 3, pp. 257-264, (2002).
"What is osteoarthritis?", NIH National Institute of Arthritis and Musculoskeletal and Skin Diseases, pp. 1-4, (2014).
Definition of "Osteoarthritis" printed from Wikipedia, the free encyclopedia, found at en.wikipedia.org/wiki/Osteoarthritis, Dec. 13, 2016.
"At a glance 2016, Arthritis, Improving the quality of life for people with arthritis", National Center for Chronic Disease Prevention and Health Promotion, pp. 1-4, (2016).
"IASP Taxonomy", International Association for the Study of Pain, found at www.iasp-pain.org/Taxonomy, pp. 1-9, (2014).

"Pain: Hope through research", National Institute of Neurological Disorders and Stroke, National Institutes of Health, pp. 1-46, (2014).
Definition of "Allodynia" printed from Wikipedia, the free encyclopedia, found at en.wikipedia.org/wiki/Allodynia, Dec. 13, 2016.
Quadros, A.U. et al., "Dynamic weight bearing is an efficient and predictable method for evaluation of arthritic nociception and its pathophysiological mechanisms in mice", Nature, Scientific Reports, pp. 1-11, (2015).
Leung, L. et al., "TNF-$\alpha$ and neuropathic pain—a review", Journal of Neuroinflammation, vol. 7, No. 27, pp. 1-11, (2010).
Schafers, M. et al., "Tumor necrosis factor-$\alpha$ induces mechanical allodynia after spinal nerve ligation by activation of p38 MAPK in primary sensory neurons", The Journal of Neuroscience, vol. 23, No. 7, pp. 2517-2521, (2003).
Sun, J.L. et al., "CX3CL1/CX3CR1 regulates nerve injury-induced pain hypersensitivity through the ERK5 signaling pathway", Journal of Neuroscience Research, vol. 91, No. 4, pp. 545-553, (2013). Abstract Only.
Watkins, L.R., et al., "Mechanisms of tumor necrosis factor-$\alpha$ (TNF-$\alpha$) hyperalgesia", Brain Research, vol. 692, issues 1-2, pp. 244-250, (1995). Abstract Only.
American Diabetes Association, "Diagnosis and classification of diabetes mellitus", Diabetes Care, vol. 31, supp. 1, pp. S55-S60, (2008).
"Global report on diabetes", World Health Organization, pp. 1-88, (2016).
"National diabetes statistics report, 2017: Estimates of diabetes and its burden in the United States", U.S. Department of Health and Human Services, Centers for Disease Control and Prevention, pp. 1-20, (2017).
O'Brien, P.D. et al., "Mouse models of diabetic neuropathy", Institute for Laboratory Animal Research Journal, vol. 54, No. 3, pp. 259-272, (2014).
O'Brien, P.D. et al., "BTBR ob/ob mice as a novel diabetic neuropathy model: Neurological characterization and gene expression analyses", Neurobiology of Disease, vol. 73, pp. 348-355, (2015).
Alpers, C.E. et al., "Mouse models of diabetic nephropathy", Current Opinion in Nephrology and Hypertension, vol. 20, No. 3, pp. 278-284, (2011).
Hudkins, K.L. et al., "BTBR ob/ob mutant mice model progressive diabetic nephropathy", Journal of the American Society of Nephrology, vol. 21, pp. 1533-1542, (2010).
O'Brien, K.D. et al., "Divergent effects of vasodilators on cardiac hypertrophy and inflammation in a murine model of diabetic cardiomyopathy", Journal of the American College of Cardiology, vol. 57, issue 17, p. e193, (2011). Abstract Only.
Lee, J-T. et al., "Macrophage metalloelastase (MMP12) regulates adipose tissue expansion, insulin sensitivity, and expression of inducible nitric oxide synthase", Endocrinology, vol. 155, No. 9, pp. 3409-3420, (2014).
Xu, X. et al., "A glimpse of matrix metalloproteinases in diabetic nephropathy", Current Medicinal Chemistry, vol. 21, No. 28, pp. 3244-3260, (2014).
Tsioufis, C. et al., "The role of matrix metalloproteinases in diabetes mellitus", Current Topics in Medicinal Chemistry, vol. 12, No. 10, pp. 1159-1165, (2012). Abstract Only.
Pechhold, K. et al., "Blood glucose levels regulate pancreatic $\beta$-cell proliferation during experimentally-induced and spontaneous autoimmune diabetes in mice", PLoS One, vol. 4, No. 3, pp. e4827, (2009).
Oh, K-J. et al., "Metabolic adaptation in obesity and type II diabetes: myokines, adipokines and hepatokines", International Journal of Molecular Sciences, vol. 18, No. 1, article 8, pp. 1-31, (2017).
Micov, A. et al., "Levetiracetam synergises with common analgesics in producing antinociception in a mouse model of painful diabetic neuropathy", Pharmacological Research, vol. 97, pp. 131-142, (2015). Abstract Only.
Feldman, E., "Tail flick assay", Animal Models of Diabetic Complications Consortium, pp. 1-3, (2004).

(56) References Cited

OTHER PUBLICATIONS

Bratwur, W., "ABT 263 was formulated in 10 ethano", found at www.selleckchem.com/blog/ABT-263-was-formulated-in-10-ethano.html, (2013). Abstract Only.
"Beta cell dysfunction", Diabetes and the Environment, found at www.diabetesandenvironment.org/home/mech/betacells, pp. 1-7, printed on Feb. 27, 2019.
Edelman, D., "Understanding beta cell exhaustion in Type 2 diabetics", Diabetes Daily, found at www.diabetesdaily.com/blog/2008/06/podcast-understanding-beta-cell-exhaustion-in-type-2-diabetics, pp. 1-6, (2008).
Cao, Y. et al., "Mechanisms of endothelial to mesenchymal transition in the retina in diabetes", Investigative Ophthalmology & Visual Science, vol. 55, pp. 7321-7331, (2014).
Palmer, A.K. et al., "Cellular senescence in Type 2 diabetes: a therapeutic opportunity", Diabetes, vol. 64, pp. 2289-2298, (2015).
Cummings, B.P. et al., "Maternal ileal interposition surgery confers metabolic improvements to offspring independent of effects on maternal body weight in UCD-T2DM rats", Obesity Surgery, vol. 23, No. 12, pp. 2042-2049, (2013).
Cummings, B.P. et al., "Development and characterization of a novel rat model of type 2 diabetes mellitus: the UC Davis type 2 diabetes mellitus UCD-T2DM rat", American Journal of Physiology Regulatory, Integrative and Comparative Physiology, vol. 295, pp. R1782-R1793, (2008).
Cummings, B.P. et al., "Bile-acid-mediated decrease in endoplasmic reticulum stress: a potential contributor to the metabolic benefits of ileal interposition surgery in UCD-T2DM rats", Disease Models & Mechanisms, vol. 6, No. 2, pp. 443-456, (2013).
Cummings, B.P. et al., "Vertical sleeve gastrectomy improves glucose and lipid metabolism and delays diabetes onset in the UCD-T2DM rats", Endocrinology, vol. 153, No. 8, pp. 3620-3632, (2012).
Cummings, B.P. et al., "Ileal interposition surgery improves glucose and lipid metabolism and delays diabetes onset in the UCD-T2DM rat", Gastroenterology, vol. 138, pp. 2437-2446, (2010).
American Diabetes Association, "Standards of medical care in diabetes—2016 abridged for primary care providers", Diabetes, vol. 34, No. 1, pp. 3-21, (2016).
Definition of "Methylglyoxal" printed from Wikipedia, the free encyclopedia, found at en.wikipedia.org/wiki/Methylglyoxal, Jun. 5, 2017.
Boesten, D.M.P.H.J. et al., "Effect of Nε-carboxymethyllysine on oxidative stress and the glutathione system in beta cells", Toxicology Reports, vol. 1, pp. 973-980, (2014).
Molla, B. et al., "Two different pathogenic mechanisms, dying-back axonal neuropathy and pancreatic senescence, are present in the YG8R mouse model of Friedreich ataxia", Disease Models & Mechanisms, vol. 9, pp. 647-657, (2016).
Kender, Z. et al., "Effect of metformin on methylglyoxal metabolism in patients with type 2 diabetes", Experimental and Clinical Endocrinology & Diabetes, vol. 122, No. 5, pp. 316-319, (2014). Abstract Only.
Ehrenmann, F. et al., "IMGT/3Dstructure-DB and IMGT/DomainGapAlign: a database and a tool for immunoglobulins or antibodies, T cell receptors, MHC, IgSF and MhcSF", Nucleic Acids Research, vol. 38, pp. D301-D307, (2010).
Glover, A., "Of mice and men", European Biophamaceutical Review, pp. 30-34, (2016).
"The basic guide to magnetic bead cell separation", Sepmag.eu, pp. 1-15, found at www.sepmag.eu/free-basic-guide-magnetic-bead-cell-separation, (2017).
Su, W-S. et al., "Controllable permeability of blood-brain barrier and reduced brain injury through low-intensity pulsed ultrasound stimulation", Oncotarget, vol. 6, No. 39, pp. 42290-42299, (2015).
International Search Report dated Jul. 21, 2009 for PCT application No. PCT/US2009/44951.
Lindsey, J.B. et al., "Receptor for advanced glycation end-products (RAGE) and soluble Rage (sRAGE): Cardiovascular implications", Diabetes Vascular Disease Research, vol. 6, No. 1, pp. 7-14, (2009).
Ando, K. et al., "Membrane proteins of human erythrocytes are modified by advanced glycation end products during aging in the circulation", Biochemical and Biophysical Research Communications, vol. 258, pp. 123-127, (1999).
Jandeleit-Dahm, K. et al., "The AGE/RAGE axis in diabetes-accelerated atherosclerosis", Clinical and Experimental Pharmacology and Physiology, vol. 35, pp. 329-334, (2008).
Sakata, N. et al., "Immunohistochemical localization of different epitopes of advanced glycation end products in human atherosclerotic lesions", Atherosclerosis, vol. 141, pp. 61-75, (1998).
Karachalias, N. et al., "Accumulation of fructosyl-lysine and advanced glycation end products in the kidney, retina and peripheral nerve of streptozotocin-induced diabetic rats", Biochemical Society Transactions, vol. 31, pp. 1423-1425, (2003).
Aroian, R. et al., "Pore-forming toxins and cellular non-immune defenses (CNIDs)", Current Opinion in Microbiology, vol. 10, pp. 57-61, (2007).
Dobson, J., "A twist on tumour targeting", Nature Materials, vol. 9, pp. 95-96, (2010).
Gutensohn, K. et al., "Extracorporeal plateletpheresis induces the interaction of activated platelets with white blood cells", Vox Sanguinis, vol. 78, No. 2, pp. 101-105, (2000).
Horiuchi, S. et al., "Immunochemical approach to characterize advanced glycation end products of the maillard reaction", The Journal of Biological Chemistry, vol. 266, No. 12, pp. 7329-7332, (1991).
Soetanto, K. et al., "Fundamental examination of cattle red blood cells damage with ultrasound exposure microscopic system (UEMS)", Japanese Journal of Applied Physics, vol. 37, part 1, No. 5B, pp. 3070-3073, (1998).
Harja, E. et al., "Vascular and inflammatory stresses mediate atherosclerosis via RAGE and its ligands in apoE-/- mice", The Journal of Clinical Investigation, vol. 118, No. 1, pp. 183-194, (2008).
Carstensen, E.L. et al., "Lysis of erythrocytes by exposure to cw ultrasound", Ultrasound in Medicine and Biology, vol. 19, No. 2, pp. 147-165, (1993).
Miller, M.W. et al., "Comparative sensitivity of human erythrocytes and lymphocytes to sonolysis by 1-MHz ultrasound", Ultrasound in Medicine and Biology, vol. 23, No. 4, pp. 635-638, (1997).
Iwata, H. et al., "Effect of carbonyl compounds on red blood cells deformability", Biochemical and Biophysical Research Communications vol. 321, pp. 700-706, (2004).
Schmitt, A. et al., "The binding of advanced glycation end products to cell surfaces can be measured using bead-reconstituted cellular membrane proteins", Biochimica et Biophysica Acta, vol. 1768, pp. 1389-1399, (2007).
Self-Medlin, Y. et al., "Glucose promotes membrane cholesterol crystalline domain formation by lipid peroxidation", Biochimica et Biophysica Acta, vol. 1788, pp. 1398-1403, (2009).
Singh, N. et al., "The PPAR-γ activator, rosiglitazone, inhibits actin polymerisation in monocytes: involvement of Akt and intracellular calcium", Biochemical and Biophysical Research Communications, vol. 333, pp. 455-462, (2005).
Li, Y-M. et al., "Effects of high glucose on mesenchymal stem cell proliferation and differentiation", Biochemical and Biophysical Research Communications, vol. 363, pp. 209-215, (2007).
Takata, K. et al., "Endocytic uptake of nonenzymatically glycosylated proteins is mediated by a scavenger receptor for aldehyde-modified proteins", The Journal of Biological Chemistry, vol. 263, No. 29, pp. 14819-14825, (1988).
Mi, Y. et al., "Apoptosis in leukemia cells is accompanied by alterations in the levels and localization of nucleolin", Journal of Biological Chemistry, vol. 278, pp. 8572-8579, (2003).
Christian, S. et al., "Nucleolin expressed at the cell surface is a marker of endothelial cells in angiogenic blood vessels", Journal of Cell Biology, vol. 163, No. 4, pp. 871-878, (2003).
Loo, T.W. et al., "Identification of residues in the drug translocation pathway of the human multidrug resistance P-glycoprotein by arginine mutagenesis", Journal of Biological Chemistry, vol. 284, No. 36, pp. 24074-24087, (2009).

(56) References Cited

OTHER PUBLICATIONS

Brundin, P. et al., "Prion-like transmission of protein aggregates in neurodegenerative diseases", Nature Reviews Molecular Cell Biology, vol. 11, No. 4, pp. 301-307, (2010).
Perez, C. et al., "Translational control of the abundance of cytoplasmic poly(A) binding protein in human cytomegalovirus-infected cells", Journal of Virology, vol. 85, No. 1, pp. 156-164, (2011).
Persson, J. et al., "Interleukin-Ibeta and tumour necrosis factor-alpha impede neutral lipid turnover in macrophage-derived foam cells", BMC Immunology, vol. 9, No. 70, pp. 1-11, (2008).
Vergne, I. et al., "Cell biology of *Mycobacterium tuberculosis* phagosome", Annu. Rev. Cell Dev. Biology, vol. 20, pp. 367-394, (2004).
Moskowitz, S.M. et al., "The role of *pseudomonas* lipopolysaccharide in cystic fibrosis airway Infection", Subcell Biochemistry, vol. 53, pp. 241-253, (2010).
Hall-Stoodley, L. et al., "Direct detection of bacterial biofilms on the middle-ear mucosa of children with chronic otitis media", JAMA, vol. 296, No. 2, pp. 202-211, (2006).
Franke-Fayard, B. et al., "Sequestration and tissue accumulation of human malaria parasites: Can we learn anything from rodent models of malaria?", PLoS Pathogens, vol. 6, issue 9, pp. 1-10, e1001032, (2010).
Zhang, S. et al., "Delineation of diverse macrophage activation programs in response to intracellular parasites and cytokines", PLoS Neglected Tropical Diseases, vol. 4, No. 3, e648 (2010).
Ma, Y. et al., "NS3 helicase domains involved in infectious intracellular hepatitis C virus particle assembly", Journal of Virology, vol. 82, No. 15, pp. 7624-7639, (2008).
Korant, B.D. et al., "Inhibition by zinc of rhinovirus protein cleavage: interaction of zinc with capsid polypeptides", Journal of Virology, vol. 18, No. 1, pp. 298-306, (1976).
Ameli, S. et al., "Effect of immunization with homologous LDL and oxidized LDL on early atherosclerosis in hypercholesterolemic rabbits", Arteriosclerosis, Thrombosis, and Vascular Biology, vol. 16, pp. 1074-1079, (1996).
Nilsson, J. et al., "Inflammation and immunity in diabetic vascular complications", Current Opinion in Lipidology, vol. 19, issue 5, pp. 519-524, (2008).
Schiopu, A. et al., "Recombinant antibodies to an oxidized low-density lipoprotein epitope induce rapid regression of atherosclerosis in apobec-1$^{-/-}$/low-density lipoprotein receptor$^{-/-}$-mice", Journal of the American College of Cardiology, vol. 50, No. 24, pp. 2313-2318, (2007).
Schiopu, A. et al., "Recombinant human antibodies against aldehyde-modified apolipoprotein B-100 peptide sequences inhibit atherosclerosis", Circulation, vol. 110, pp. 2047-2052, (2004).
Bassirat, M. et al., "Short- and long-term modulation of microvascular responses in streptozotocin-induced diabetic rats by glycosylated products", Journal of Diabetes and its Complications, vol. 24, pp. 64-72, (2010).
Ge, J. et al., "Advanced glycosylation end products might promote atherosclerosis through inducing the immune maturation of dendritic cells", Arteriosclerosis, Thrombosis, and Vascular Biology, vol. 25, pp. 2157-2163, (2005).
Gugliucci, A. et al., "Circulating advanced glycation peptides in streptozotocin-induced diabetic rats: evidence for preferential modification of IgG light chains", Life Sciences, vol. 62, No. 23, pp. 2141-2150, (1998).
Pullerits, R. et al., "Synovial fluid expression of autoantibodies specific for RAGE relates to less erosive course of rheumatoid arthritis", Rheumatology, vol. 46, pp. 1367-1371, (2007).
Bro, S. et al., "A neutralizing antibody against receptor for advanced glycation end products (RAGE) reduces atherosclerosis in uremic mice", Atherosclerosis, vol. 201, pp. 274-280, (2008).
Turk, Z. et al., "Detection of autoantibodies against advanced glycation endproducts and AGE-immune complexes in serum of patients with diabetes mellitus", Clinica Chimica Acta, vol. 303, pp. 105-115, (2001).
Li, M. et al., "Glycan changes: cancer metastasis and anti-cancer vaccines", Journal of Biosciences, vol. 35, No. 4, pp. 665-673, (2010).
Kyte, J.A. et al., "Third international conference on cancer vaccines/adjuvants/delivery for the next decade (CVADD 2009)", Expert Reviews Vaccines, vol. 9, No. 2, pp. 119-123, (2010).
Akbulut, H. et al., "Chemotherapy targeted to cancer tissue potentiates antigen-specific immune response induced by vaccine for in vivo antigen loading and activation of dendritic cells", Molecular Therapy, vol. 16, No. 10, pp. 1753-1760, (2008).
Li, Y.M. et al., "Glycation products in aged thioglycollate medium enhance the elicitation of peritoneal macrophages", Jounal of Immunological Methods, vol. 201, issue 2, pp. 183-188, (1997).
Poggioli, S. et al., "Age-related increase of protein glycation in peripheral blood lymphocytes is restricted to preferential target proteins", Experimental Gerontology, vol. 37, issue 10-11, pp. 1207-1215, (2002).
Poggioli, S. et al., "Evidence of preferential protein targets for age-related modifications in peripheral blood lymphocytes", Annals of the New York Academy of Sciences, vol. 1019, issue 1, pp. 211-214, (2004).
Dominaitiene, R. et al., "Effects of differently oxidized LDL on the expression of pro-inflammatory molecules in human monocytes in vitro", In Vitro and Molecular Toxicology, vol. 14, No. 2, pp. 83-97, (2001).
Jiang, Z-H. et al., "Synthetic vaccines: the role of adjuvants in immune targeting", Current Medicinal Chemistry, vol. 10, No. 15, pp. 1423-1439, (2003).
Buskas, T. et al., "Immunotherapy for cancer: Synthetic carbohydrate-based vaccines", Chemical Communications, Issue 36, pp. 5335-5349, (2009).
Cohen, M.P. et al., "Amelioration of diabetic nephropathy by treatment with monoclonal antibodies against glycated albumin", Kidney International, vol. 45, pp. 1673-1679, (1994).
Davis, P.J. et al., "How can thermal processing modify the antigenicity of proteins?", Allergy, vol. 56, supplemental 67, pp. 56-60, (2001).
Koga, M. et al. "Clinical impact of glycated albumin as another glycemic control marker", Endocrine Journal, vol. 57, No. 9, pp. 751-762, (2010).
Shcheglova, T. et al., "Reactive immunization suppresses advanced glycation and mitigates diabetic nephropathy", Journal of the American Society of Nephrology, vol. 20, No. 5, pp. 1012-1019, (2009).
Virella, G. et al., "Autoimmune response to advanced glycosylation end-products of human LDL", Journal of Lipid Research, vol. 44, pp. 487-493, (2003).
Ihssen, J. et al., "Production of glycoprotein vaccines in *Escherichia coli*", Microbial Cell Factories, vol. 9, No. 61, pp. 1-13, (2010).
Habets, K.L.L. et al., "Vaccination using oxidized low-density lipoprotein-pulsed dendritic cells reduces atherosclerosis in LDL receptor-deficient mice", Cardiovascular Research, vol. 85, pp. 622-630, (2010).
Mironova, R. et al., "Glycation and post-translational processing of human interferon-γ expressed in *Escherichia coli*", The Journal of Biological Chemistry, vol. 278, No. 51, pp. 51068-51074, (2003).
Vogel, F.R. et al., "A compendium of vaccine adjuvants and excipients", Pharmaceutical Biotechnology, vol. 6, pp. 141-228, (1995).
Monograph series, World Health Organization, "Methods of Vaccine Production", part 4, chapters 18-29, pp. 189-267, (1973).
Cohen, M.P. et al., "Prevention of diabetic nephropathy in db/db mice with glycated albumin antagonists: A novel treatment strategy", The Journal of Clinical Investigation, vol. 95, pp. 2338-2345, (1995).
Naka, Y. et al., "RAGE Axis, Animal models and novel insights into the vascular complications of diabetes", Arteriosclerosis, Thrombosis, and Vascular Biology, vol. 24, pp. 1342-1349, (2004).
European Search Report dated Nov. 8, 2011 for PCT application No. PCT/US2009/044951.
Bierhaus, A. et al., "AGEs and their interaction with AGE-receptors in vascular disease and diabetes mellitus. I. the AGE concept", Cardiovascular Research, vol. 37, No. 3, pp. 586-600, (1998).

(56) References Cited

OTHER PUBLICATIONS

Murphy, J.F. "Trends in cancer immunotherapy", Clinical Medicine Insights: Oncology, vol. 4, pp. 67-80, (2010).
Beier, K.C., "Master switches of T-cell activation and differentiation", European Respiratory Journal, vol. 29, pp. 804-812, (2007).
Schmidlin, H., "New insights in the regulation of human B cell differentiation", Trends in Immunology, vol. 30, No. 6, pp. 277-285, (2009).
Coler, R.N. et al., "Development and characterization of synthetic glucopyranosyl lipid adjuvant system as a vaccine adjuvant", PLoS One, vol. 6, No. 1, e16333, pp. 1-12, (2011).
Cheadle, E.J., "Bugs as drugs for cancer", Immunology, vol. 107, pp. 10-19, (2002).
The Pink Book, Epidemiology and Prevention of vaccine preventable diseases, 11$^{th}$ Ed., pp. B7-B13, (2009), Found at www.cdc.gov/vaccines/pubs/pinkbook/downloads/appendices/b/excipient-table-1.pdf.
The Pink Book, Epidemiology and Prevention of vaccine preventable diseases, 11$^{th}$ Ed., 4 pages, (2009), Found at www.cdc.gov/vaccines/pubs/pinkbook/downloads/appendices/b/excipient-table-2.pdf.
Book Reviews, International Microbiology, vol. 7, pp. 291-295, (2004).
"Glycation: How eating sugar causes wrinkles", www.brighthub.com/health/diet-nutrition/articles/18410.aspx, 1 page, published Oct. 8, 2009.
Ellis, G., "The myth of the glycemic index and its child: good carbs-bad carbs", Targeted Body Systems, www.targetedbodysystems.com/tag/low-carb-diet-plans/, pp. 1-5, published Feb. 16, 2009.
"Diabetic glycation and inflammation—what diabetes does to your coronary arteries", www.rebelheartsurgeon-antioxidants.net/diabetic-glycation.html, pp. 1-9, downloaded Aug. 17, 2010.
Dziarski, R., "Cell-bound albumin is the 70-kDa peptidoglycan-, lipopolysaccharide-, and lipoteichoic acid-binding protein on lymphocytes and macrophages", The Journal of Biological Chemistry, vol. 269, No. 32, pp. 20431-20436, (1994).
Peters Jr. T., "5-Metabolism: Albumin in the body", All About Albumin Biochemistry, Genetics, and Medical Applications, Chapter 5, pp. 188-250, (1995).
Vlassara, H. et al., "High-affinity-receptor-mediated uptake and degradation of glucose-modified proteins: A potential mechanism for the removal of senescent macromolecules", Proceeding of the National Academy of Science, USA, Biochemistry, vol. 82, pp. 5588-5592, (1985).
Wade, N., "Purging cells in mice is found to combat aging ills", New York Times, found at NYTimes.com, pp. 1-3, (2011).
Roll, P. et al., "Anti-CD20 therapy in patients with rheumatoid arthritis", Arthritis & Rheumatism, vol. 58, No. 6, pp. 1566-1575, (2008).
Kajstura J. et al., "Myocyte turnover in the aging human heart", Circulation Research, vol. 107, pp. 1374-1386, (2010).
Baker, D.J. et al., "Clearance of p16Ink4a-positive senescent cells delays ageing-associated disorders", Nature, vol. 479, pp. 232-236, (2011).
Breyer, V. et al., "Intracellular glycation of nuclear DNA, mitochondrial DNA, and cytosolic proteins during senescence-like growth arrest", DNA Cell Biology, vol. 30, No. 9, pp. 681-689, (2011).
Ravelojaona, V. et al., "Expression of senescence-associated beta-galactosidase (SA-beta-Gal) by human skin fibroblasts, effect of advanced glycation end-products and fucose or rhamnose-rich polysaccharides", Archives of Gerontology and Geriatrics, vol. 48, issue 2, pp. 151-154, (2009).
International Search Report dated Apr. 26, 2012 for PCT application No. PCT/US2011/053399.
International Search Report dated Jun. 13, 2012 for PCT application No. PCT/US2011/061387.
Wautier, J. -L. et al., "Advanced glycation end products (AGEs) on the surface of diabetic erythrocytes bind to the vessel wall via a specific receptor inducing oxidant stress in the vasculature: A link between surface-associated AGEs and diabetic complications", Proc. Natl. Acad. Sci. USA, vol. 91, No. 16, pp. 7742-7746, (1994).
Siegel, R. J. et al., "Ultrasonic plaque ablation: A new method for recanalization of partially or totally occluded arteries", Circulation, vol. 78, No. 6, pp. 1443-1448, (1988).
International Search Report dated Jun. 27, 2012 for PCT application No. PCT/US2012/031446.
Immuno, Catalog No. 637061, 637062, "Mouse, anti-age (advanced glycation end products), monoclonal antibody", http://www.mpbio.com/detailed_info.php?family_key=0863706, 2 pages, accessed Jul. 26, 2012.
Ahmed, E. K. et al., "Protein modification and replicative senescence of WI-38 human embryonic fibroblasts", Aging Cell, vol. 9, pp. 252-272, (2010).
Vlassara, H. et al, "Advanced glycosylation endproducts on erythrocyte cell surface induce receptor-mediated phagocytosis by macrophages", J. Exp. Med., The Rockefeller University Press, vol. 166, pp. 539-549, (1987).
Yang, Z. et al., "Two novel rat liver membrane proteins that bind advanced glycosylation endproducts: Relationship to macrophage receptor for glucose-modified proteins", J. Exp. Med., The Rockefeller University Press, vol. 174, pp. 515-524, (1991).
Vlassara, H. et al, "Advanced glycation endproducts promote adhesion molecule (VCAM-1, ICAM-1) expression and atheroma formation in normal rabbits", Molecular Medicine, vol. 1, No. 4, pp. 447-456, (1995).
Vaysse, J. et al., "Adhesion and erythrophagocytosis of human senescent erythrocytes by autologous monocytes and their inhibition by β-galactosyl derivatives", Proc. Natl. Acad. Sci. USA, Cell Biology, vol. 83, pp. 1339-1343, (1986).
Li, Y. M. et al., "Prevention of cardiovascular and renal pathology of aging by the advanced glycation inhibitor aminoguanidine", Proc. Natl. Acad. Sci. USA, Medical Sciences, vol. 93, pp. 3902-3907, (1996).
Manesso, E. et al., "Dynamics of β-cell turnover: evidence for β-cell turnover and regeneration from sources of β-cells other than β-cell replication in the HIP rat", American Journal of Physiology—Endocrinology and Metabolism, vol. 297, pp. E323-E330, (2009).
Stepanov, a.V. et al., "Design of targeted B cell killing agents", PLoS One, vol. 6, issue 6, e20991, pp. 1-10, (2011).
Fact Sheet, "Targeted Cancer Therapies", www.cancer.gov/cancertopics/factsheet/Therapy/Fs7_49.pdf, pp. 1-8, (2012).
Kay, M.M. "Generation of senescent cell antigen on old cells initiates IgG binding to a neoantigen", Cellular and Molecular Biology (Noisy-le-Grand, France), vol. 39, No. 2, pp. 131-153, (1993), Abstract Only.
Cirocchi, R. et al., "Meta-analysis of thyroidectomy with ultrasonic dissector versus conventional clamp and tie", World Journal of Surgical Oncology, vol. 8, No. 112, pp. 1-7, (2010).
Lingeman, J.E. et al., "Current perspective on adverse effects in shock wave lithotripsy", White Paper, American Urological Association Education and Research, found at www.auanet.org/content/guidelines-and-quality-care/clinical-guidelines/main-reports/whitepaper.pdf, 17 pages, (2009).
de Groot, K. et al., "Vascular endothelial damage and repair in antineutrophil cytoplasmic antibody-associated vasculitis", Arthritis & Rheumatism, vol. 56, No. 11, pp. 3847-3853, (2007).
Imani, F. et al., "Advanced glycosylation endproduct-specific receptors on human and rat t-lymphocytes mediate synthesis of interferon γ: role in tissue remodeling", J. Exp. Med., vol. 178, pp. 2165-2172, (1993).
Kirstein, M. et al., "Receptor-specific induction of insulin-like growth factor I in human monocytes by advanced glycosylation end product-modified proteins", J. Clin. Invest., vol. 90, pp. 439-446, (1992).
Le Grand, F. et al., "Skeletal muscle satellite cells and adult myogenesis", Curr. Opin. Cell Biology, vol. 19, No. 6, pp. 628-633, (2007).
Sasaki, M. et al., "Mesenchymal stem cells are recruited into wounded skin and contribute to wound repair by transdifferentiation into multiple skin cell type", The Journal of Immunology, vol. 180, pp. 2581-2587, (2008).

(56) References Cited

OTHER PUBLICATIONS

Misur, I. et al., "Advanced glycation endproducts in peripheral nerve in type 2 diabetes with neuropathy", Acta Diabetol, vol. 41, pp. 158-166, (2004).
Saltykov, B.B., "Mechanisms of development of diabetic macroangiopathy", Arkh Patol., vol. 63, No. 2, pp. 21-26, (2001), Abstract Only.
Grossin, N. et al., "Red blood cell adhesion in diabetes mellitus is mediated by advanced glycation end product receptor and is modulated by nitric oxide", Biorheology, vol. 46, No. 1, pp. 63-72, (2009).
Liang, Y. et al., "Rituximab for children with immune thrombocytopenia: A systematic review", PLoS One, vol. 7, issue 1, pp. 1-11, (2012).
Fehrenbach, H. et al., "Up-regulated expression of the receptor for advanced glycation end products in cultured rat hepatic stellate cells during transdifferentiation to myofibroblasts", Hepatology, vol. 34, No. 5, pp. 943-952, (2001).
Agostini, A. et al., "Targeted cargo delivery in senescent cells using capped mesoporous silica nanoparticles", Angewandte Chemie International Edition, vol. 51, pp. 10556-10560, (2012).
Larson, R.A. et al., "Tumor lysis syndrome: Definition, pathogenesis, clinical manifestations, etiology and risk factors", found at www.uptodate.com/contents/tumor-lysis-syndrome-definition-pathogenesis-clinical-manifestations-etiology-and-risk-factors?detectedLanguage=en&source=search_result&search=tumor+lysis+syndrome&selectedTitle=2~69&provider=noProvider, pp. 1-4, printed on Jun. 11, 2013.
Hansel, T.T. et al., "The safety and side effects of monoclonal antibodies", Nature Reviews, vol. 9, pp. 325-337, (2010).
Nass, N. et al., "Advanced glycation end products, diabetes and ageing", Zeitschrift fur Gerontologie und Geriatrie, vol. 40, issue 5, pp. 349-356, (2007).
Wautier, J-L. et al., Protein Glycation: "A firm link to endothelial cell dysfunction", Circulation Research, Journal of the American Heart Association, vol. 95, pp. 233-238, (2004).
Meuter, A. et al., "Markers of cellular senescence are elevated in murine blastocysts cultured in vitro: molecular consequences of culture in atmospheric oxygen", Journal of Assisted Reproduction and Genetics, vol. 31, issue 10, pp. 1259-1267, (2014).
Freund, A. et al., "Inflammatory networks during cellular senescence: causes and consequences", Trends in Molecular Medicine, vol. 16, No. 5, pp. 238-246, (2010).
Hadrabová, J. et al., "Chicken immunoglobulins for prophylaxis: Effect of inhaled antibodies on inflammatory parameters in rat airways", Journal of Applied Biomedicine, 4 pages, Available online May 5, 2014.
Ferraccioli, G. et al., "Interleukin-1β and Interleukin-6 in arthritis animal models: Roles in the early phase of transition from acute to chronic inflammation and relevance for human rheumatoid arthritis", Molecular Medicine, vol. 16, issue 11-12, pp. 552-557, (2010).
Zhao, Y. et al., "The bovine antibody repertoire", Developmental & Comparative Immunology, vol. 30, issues 1-2, pp. 175-186, (2006).
Wagner, B. et al., "The complete map of the Ig heavy chain constant gene region reveals evidence for seven IgG isotypes and for IgD in the horse", Journal of Immunology, vol. 173, No. 5, pp. 3230-3242, (2004).
Strietzel, C.J. et al., "In vitro functional characterization of feline IgGs", Veterinary Immunology and Immunopathology, vol. 158, issues 3-4, pp. 214-223, (2014).
Patel, M. et al., "Sequence of the dog immunoglobulin alpha and epsilon constant region genes", Immunogenetics, vol. 41, issue 5, pp. 282-286, (1995).
Maass, D.R. et al., "Alpaca (*Lama pacos*) as a convenient source of recombinant camelid heavy chain antibodies (VHHs)", Journal of Immunology Methods, vol. 324, issues 1-2, pp. 13-25, (2007).
European Search Report dated Sep. 12, 2014 for EP application No. EP14170802.4-1408.
Fessler, J. et al., "Senescent T cells promote bone loss in rheumatoid arthritis", Abstracts of the American College of Rheumatology/Association of Rheumatology Health Professionals, Annual Scientific Meeting, Washington, DC, Nov. 9-14, 2012, Arthritis & Rheumatism, vol. 64, supplement 10, p. 2312, (2012) found at http://blackwellpublishing.com/acrmeeting/abstract.asp?MeetingID=789&id=103040.
Weyand, C.M. et al., Abstract of "T-cell aging in rheumatoid arthritis", Current Opinion in Rheumatology, vol. 26, No. 1, pp. 93-100, (2014) found at http://www.ncbi.nlm.nih.gov/m/pubmed/24296720/.
Dvergsten, J. et al., "Prevalence of functionally active, senescent T cells in juvenile idiopathic arthritis", Abstracts of the American College of Rheumatology/Association of Rheumatology Health Professionals, Annual Scientific Meeting, Philadelphia, Oct. 16-21, 2009, Arthritis & Rheumatism, vol. 60, supplement 10, p. 1313, (2009), found at http://blackwellpublishing.com/acrmeeting/abstract.asp?MeetingID=761&id=80937.
Definition of "Dissociation constant" printed from Wikipedia, the free encyclopedia on Sep. 17, 2014 found at http://en.wikipedia.org/wiki/Dissociation_constant.
Sigma-Aldrich product specification of "Nα,Nα-Bis(carboxymethyl)-L-lysine trifluoroacetate salt ≥95% (TLC)", found at http://sigmaaldrich.com/catalog/product/sigma/c3205?lang=en&region=US, printed on Sep. 17, 2014.
"Pulmatrix demonstrates iSPERSE capabilities for inhaled dry powder delivery of antibiotics and antibodies", data presented at Respiratory Drug Delivery 2012, 3 pages, printed on Sep. 4, 2014, found at http://businesswire.com/news/home/20120515005279/en/Pulmatrix-Demonstrates-iSPERSE-Capabilities-Inhaled-Dry-Powder#.VEgU4hauNbs.
Chan, A.C. et al., "Therapeutic antibodies for autoimmunity and inflammation", Nature Reviews Immunology, vol. 10, pp. 301-316, (2010).
Pradat, P.F. et al., "Abnormalities of satellite cells function in amyotrophic lateral sclerosis", Amyotrophic Lateral Sclerosis, vol. 12, No. 4, pp. 264-271, (2011).
Kitada, K. et al., "Aldosterone induces p21-regulated apoptosis via increased synthesis and secretion of tumour necrosis factor-α in human proximal tubular cells", Clinical and Experimental Pharmacology and Physiology, vol. 39, No. 10, pp. 858-863, (2012).
Definition of "TNF inhibitor", printed from Wikipedia, the free encyclopedia on Oct. 4, 2014, 4 pages, found at http://en.wikipedia.org/wiki/TNF_inhibitor?oldid=628250399.
Definition of "Etanercept", printed from Wikipedia, the free encyclopedia on Aug. 24, 2014, 6 pages, found at http://en.wikipedia.org/wiki/Etanercept?oldid=622648157.
AbbVie, Inc., "Humira adalimumab: Learn about Humira", found at https://www.humira.com/rheumatoid-arthritis, 7 pages, printed on Aug. 11, 2014.
AbbVie, Inc., "Medication Guide for Humira", found at https://www.humira.com/rheumatoid-arthritis, 9 pages, printed on Aug. 11, 2014.
AbbVie, Inc., "Humira: A biologic that targets and helps block TNF-alpha", found at https://www.humira.com/rheumatoid-arthritis/how-humira-works-for-ra, 8 pages, printed on Aug. 11, 2014.
AbbVie, Inc., "How Humira (adalimumab) works video transcript", found at https://www.humira.com/rheumatoid-arthritis/how-humira-works-video-transcript, 5 pages, printed on Aug. 11, 2014.
AbbVie, Inc., "Humira and methotrexate—a combination that has demonstrated results", found at https://www.humira.com/rheumatoid-arthritis/humira-and-methotrexate, 7 pages, printed on Aug. 11, 2014.
Madhur, M.S. et al., "Senescent T cells and hypertension: New ideas about old cells", Hypertension, vol. 62, pp. 13-15, (2013).
James, P.E. et al., "Vasorelaxation by red blood cells and impairment in diabetes: Reduced nitric oxide and oxygen delivery by glycated hemoglobin", Circulation Research, vol. 94, pp. 976-983, (2004).
Shibayama, R. et al., "Autoantibody against N(epsilon)-(carboxymethyl)lysine: an advanced glycation end product of the Maillard reaction", Diabetes, vol. 48, No. 9, pp. 1842-1849, (1999).
Bumol, T.F. et al., "Monoclonal antibody and an antibody-toxin conjugate to a cell surface proteoglycan of melanoma cells suppress in vivo tumor growth", Proceeding of the National Academy of Science, vol. 80, pp. 529-533, (1983).

(56) References Cited

OTHER PUBLICATIONS

"AGEs (all species) antibody—Product Details", Antibodies Online, 4 pages, found at www.web.archive.org/web/20081229071154/http://www.antibodies-online.com/antibody/289931/AGEs+All+Species/, printed on Dec. 10, 2014.
"Antibody Engineering", Fusion Antibodies, 2 pages, found at www.web.archive.org/web/20080628225818/http://www.fusionantibodies.com/index.cfm/area/information/page/engineering?, printed on Dec. 16, 2014.
Hargreaves, R.E.G. et al., "Selective depletion of activated T cells: the CD40L-specific antibody experience", TRENDS in Molecular Medicine, vol. 10, No. 3, pp. 130-135, (2004).
Leinenga, G. et al., "Scanning ultrasound removes amyloid-β and restores memory in an Alzheimer's disease mouse model", Science Translational Medicine, vol. 7, issue 278, pp. 1-11, (2015).
Peppa, M. et al., "Glucose, advanced glycation end products, and diabetes complications: What is new and what works", Clinical Diabetes, vol. 21, No. 4, pp. 186-187, (2003).
Lv, Y. et al., "Low-intensity ultrasound combined with 5-aminolevulinic acid administration in the treatment of human tongue squamous carcinoma", Cellular Physiology and Biochemistry, vol. 30, pp. 321-333, (2012).
Campisi, J. et al., "Cellular senescence: when bad things happen to good cells", Nature Reviews: Molecular Cell Biology, vol. 8, pp. 729-749, (2007).
"ALSUntangled No. 23: The Rife Machine and retroviruses", Amyotrophic Lateral Sclerosis and Frontotemporal Degeneration, vol. 15, pp. 157-159, (2014).
Roylance, D., "Mechanical properties of materials", pp. 1-128, (2008), available at www.web.mit.edu/course/3/3.225/book.pdf.
Vidarsson, G. et al., "IgG subclasses and allotypes: from structure to effector functions", Frontiers in Immunology, vol. 5, article 520, pp. 1-17, (2014).
Lin, H-T. et al., "Stem cell therapy: an exercise in patience and prudence", Philosophical Transactions of the Royal Society B: Biological Sciences 368, (2013).
Waldmann, T.A., "Immunotherapy:past, present and future", Nature Medicine, vol. 9, No. 3, pp. 269-277, (2003).
Okamoto, T. et al., "Advanced glycation end products induce angiogenesis in vivo", Microvascular Research, vol. 63, pp. 186-195, (2002).
Nagal, R. et al., "Application of monoclonal antibody libraries for the measurement of glycation adducts", Biochemical Society Transactions, vol. 31, part 6, pp. 1438-1440, (2003).
De Genst, E. et al., "Antibody repertoire development in camelids", Developmental and Comparative Immunology, vol. 30, pp. 187-198, (2006).
Griffin, L.M. et al., "Analysis of hevy and light chain sequences of conventional camelid antibodies from *Camelus dromedarius* and *Camelus bactrianus* species", Journal of Immunological Methods, vol. 405, pp. 35-46, (2014).
Hamers-Casterman, C. et al., "Naturally occurring antibodies devoid of light chains", Nature, vol. 363, pp. 446-448, (1993).
Muyldermans, S. et al., "Sequence and structure of $V_H$ domain from naturally occurring camel heavy chain immunoglobulins lacking light chains", Protein Engineering, vol. 7, No. 9, pp. 1129-1135, (1994).
Nguyen, V. K. et al., "Camel heavy-chain antibodies: diverse germline VHH and specific mechanisms enlarge the antigen-binding repertoire", The EMBO Journal, vol. 19, No. 5, pp. 921-930, (2000).
Kirstein, et al., "Advanced protein glycosylation induces transendothelial human monocyte chemotaxis and secretion of platelet-derived growth factor: roll in vascular disease of diabetes and aging", PNAS, vol. 87, No. 22, pp. 9010-9014, (1990).
Invitation to Pay Additional Fees and Partial International Search Report dated Jan. 13, 2016 for PCT application No. PCT/US2015/050154.

Feldmann, M. et al., "Anti-TNFalpha therapy of rheumatoid arthritis: What have we learned?", Annual Review of Immunology, vol. 19, pp. 163-196, (2001).
Drinda, S. et al., "Identification of the advanced glycation end products N-carboxymethyllysine in the synovial tissue of patients with rheumatoid arthritis", Annals of the Rheumatic Diseases, vol. 61, No. 6, pp. 488-492, (2002).
Ahmad, S. et al., "Preferential recognition of epitopes on AGE-IgG by the autoantibodies in rheumatoid arthritis patients", Human Immunology, vol. 74, No. 1, pp. 23-27, (2013).
Johns, L.D., "Nonthermal effects of therapeutic ultrasound: The frequency resonance hypothesis", Journal of Athletic Training, vol. 37, No. 3, pp. 293-299, (2002).
Wang, B-L. et al., "Identification of monoclonal antibody of advanced glycation end products", Chinese Journal of Arteriosclerosis, vol. 14, No. 5, pp. 409-412, (2006).
Wang, J.C. et al., "Aging and Atherosclerosis mechanisms, functional consequences, and potential therapeutics for cellular senescence", Circulation Research, vol. 111, pp. 245-259, (2012).
Minamino, T. et al., "Vascular cell senescence contribution to Atherosclerosis", Circulation Research, vol. 100, pp. 15-26, (2007).
Isoda, K. et al., "Glycated LDL increases monocyte CC chemokine receptor 2 expression and monocyte chemoattractant protein-1-mediated chemotaxis", Atherosclerosis, vol. 198, No. 2, pp. 307-312, (2008).
Roos, C.M. et al., "Chronic senolytic treatment alleviates established vasomotor dysfunction in aged or atherosclerotic mice", Aging Cell, 8 pages, (2016).
Hall, B.M. et al., "Aging of mice is associated with p16(Ink4a)- and β-galactosidase-positive macrophage accumulation that can be induced in young mice by senescent cells", Aging, vol. 8, No. 7, pp. 1-18, (2016).
Mera, K. et al., "An autoantibody against $N^{249}$-(carboxyethyl)lysine (CEL): Possible involvement in the removal of CEL-modified proteins by macrophages", Biochemical and Biophysical Research Communications, vol. 407, pp. 420-425, (2011).
Reddy, S. et al., "$N^{\epsilon}$-(Carboxymethyplysine is a dominant advanced glycation end product (AGE) antigen in tissue proteins", Biochemistry, vol. 34, pp. 10872-10878, (1995).
Katcher, H.L., "Studies that shed new light on aging", Biochemistry (Moscow), vol. 78, No. 9, pp. 1061-1070, (2013).
Naylor, R.M. et al., "Senescent Cells: A novel therapeutic target for aging and age-related diseases", Clinical Pharmacology & Therapeutics, vol. 93, No. 1, pp. 105-116, (2013).
Beaulieu, L-P. et al., "Inhibitory effect of the cree traditional medicine wiishichimanaanh (vaccinium vitis-idaea) on advanced glycation endproduct formation: identification of active principles", Phytotherapy Research, vol. 24, pp. 741-747, (2010).
Ulrich, P. et al., "Protein glycation, diabetes, and aging", Recent Progress in Hormone Research, vol. 56, pp. 1-21, (2000).
Van Heijst, J.W.J. et al., "Advanced glycation end products in human cancer tissues: detection of $N^{\epsilon}$-(carboxymethyl)lysine and argpyrimidine", Annals of the New York Academy of Sciences, vol. 1043, pp. 725-733, (2005).
Fielding, R.A. et al., "Sarcopenia: An undiagnosed condition in older adults. Current consensus definition: Prevalence, etiology, and consequences", Journal of the American Medical Directors Association, vol. 12, No. 4, pp. 249-256, (2011).
Definition of "Sarcopenia", printed from Wikipedia, the free encyclopedia on Jul. 25, 2016, 5 pages, found at http://en.wikipedia.org/wiki/Sarcopenia.
"What is Sarcopenia?", International Osteoporosis Foundation, 2 pages, found at www.iofbonehealth.org/what-sarcopenia, (2014).
"Sarcopenia with aging", Webmd, 2 pages, found at www.webmd.com/healthy-aging/sarcopenia-with-aging, (2014).
Definition of "Keyhole limpet hemocyanin", printed from Wikipedia, the free encyclopedia on Jul. 25, 2016, 4 pages, found at https://en.wikipedia.org/wiki/Keyhole_limpet_hemocyanin.
Cell Biolabs, Inc., "CML-BSA Product Data Sheet", 3 pages, found at http://www.cellbiolabs.com/sites/default/files/STA-314-cml-bsa.pdf, (2010).

(56) References Cited

OTHER PUBLICATIONS

Cell Biolabs, Inc., "CML (N-epsilon-(Caboxymethyl)Lysine) Assays and Reagents", 1 page, found at http://www.cellbiolabs.com/cml-assays, (2014).
Cruz-Jentoft, A.J. et al., "Sarcopenia: European consensus on definition and diagnosis", Age and Ageing, vol. 39, pp. 412-423, (2010).
Rolland, Y. et al., "Sarcopenia: Its assessment, etiology, pathogenesis, consequences and future perspectives", The Journal of Nutrition, Health & Aging, vol. 12, No. 7, pp. 433-450, (2008).
Centers for Disease Control and Prevention, "Vaccine excipient and media summary", 4 pages, found at www.cdc.gov/vaccines/pubs/pinkbook/downloads/appendices/B/excipient-table-2.pdf?utm_content=buffer4538f&utm_medium=social&utm_source=linkedin.com&utm_campaign=buffer, (2015).
Definition of "N(6)-Carboxymethyllysine", printed from Wikipedia, the free encyclopedia on Dec. 8, 2013, 1 page, found at http://en.wikipedia.org/wiki/N(6)-Carboxymethyllysine.
Definition of "Lysine", printed from Wikipedia, the free encyclopedia on Dec. 8, 2013, 1 page, found at http://en.wikipedia.org/wiki/Lysine.
Jarvis, L.M., "Rethinking antibody-drug conjugates", Chemical & Engineering News, vol. 90, issue 25, pp. 12-18, (2012).
Mullin, R., "Cell-free approach to antibody-drug conjugates", Chemical & Engineering News, vol. 91, issue 44, 2 pages, (2013).
Thayer, A.M., "Building antibody-drug conjugates", Chemical & Engineering News, vol. 92, issue 3, pp. 13-21, (2014).
Feige, M.J. et al., "The structural analysis of shark IgNAR antibodies reveals evolutionary principles of immunoglobulins", Proceedings of the National Academy of Sciences, vol. 111, No. 22, pp. 8155-8160, (2014).
Philipot, D. et al., "p16$^{INK4a}$ and its regulator miR-24 link senescence and chondrocyte terminal differentiation-associated matrix remodeling in osteoarthritis", Arthritis Research & Therapy, vol. 16, No. 1, pp. 1-12, (2014).
International Search Report and Written Opinion dated Mar. 31, 2016 for PCT application No. PCT/US2015/050154.
Zhu, Y. et al., "The achilles' heel of senescent cells: from transcriptome to senolytic drugs", Aging Cell, vol. 14, pp. 644-658, (2015).
Zhu, L. et al., "Immunization with advanced glycation end products modified low density lipoprotein inhibits atherosclerosis progression in diabetic apoE and LDLR null mice", Cardiovascular Diabetology, vol. 13, No. 151, pp. 1-12, (2014).
DeNardo, S.J. et al., "Development of tumor targeting bioprobes ($^{111}$in-chimeric L6 monoclonal antibody nanoparticles) for alternating magnetic field cancer therapy", Clinical Cancer Research, vol. 11, 19 supplemental, pp. 7087s-7092s, (2005).
Chen, L. et al., "Cytolysis of human erythrocytes by a covalent antibody-selenium immunoconjugate", Free Radical Biology & Medicine, vol. 19, No. 6, pp. 713-724, (1995).
Yuan, Y. et al., "Advanced glycation end products (AGEs) increase human mesangial foam cell formation by increasing Golgi SCAP glycosylation in vitro", American Journal of Physiology—Renal Physiology, vol. 301.1, pp. F236-F243, (2011).
Hashimoto, M. et al., "Elimination of p19$^{ARF}$-expressing cells enhances pulmonary function in mice", JCI Insight, vol. 1, No. 12, pp. 1-15, (2016).
Yan, S.F. et al., "Soluble RAGE: Therapy & biomarker in unraveling the RAGE axis in chronic disease and aging", Biochemical Pharmacology, vol. 79, No. 10, pp. 1379-1386, (2010).
Xue, J. et al., "Advanced glycation end product (AGE) recognition by the receptor for AGEs (RAGE)", Structure, vol. 19, No. 5, pp. 722-732, (2011).
Chang, J. et al., "Clearance of senescent cells by ABT263 rejuvenates aged hematopoietic stem cells in mice", Nature Medicine, vol. 22, No. 1, pp. 78-83, (2016).
Geiger, H., "Depleting senescent cells to combat aging", Nature Medicine, vol. 22, No. 1, pp. 23-24, (2016).
Ni, J. et al., "Plasma protein pentosidine and carboxymethyllysine, biomarkers for age-related macular degeneration", Molecular & Cellular Proteomics, vol. 8, No. 8, pp. 1921-1933, (2009).
R&D Systems, a biotechne brand, product specification of "Carboxymethyl Lysine Antibody", found at https://www.rndsystems.com/products/carboxymethyl-lysine-antibody-318003_mab3247, 1 page, (2015).
Schalkwijk, C.G. et al., "Increased accumulation of the glycoxidation product N$^\varepsilon$-(carboxymethyl)lysine in hearts of diabetic patients: generation and characterization of a monoclonal anti-CML antibody", Biochimica et Biophysica Acta (BBA)—Molecular and Cell Biology of Lipids, vol. 1636, No. 2, pp. 82-89, (2004).
LaPak, K.M. et al., "The molecular balancing act of p16$^{INK4a}$ in cancer and aging", Molecular Cancer Research, vol. 12, No. 2, pp. 167-183, (2013).
Larsen, S.A. et al., "Glucose metabolite glyoxal induces senescence in telomerase-immortalized human mesenchymal stem cells", Chemistry Central Journal, vol. 6, No. 18, pp. 1-13, (2012).
Ahmed, M.U. et al., "N$^\varepsilon$-(carboxymethyl)lysine, a product of the chemical modification of proteins by methylglyoxal, increases with age in human lens proteins", Biochemical Journal, vol. 324, pp. 565-570, (1997).
Dunn, J.A. et al., "Age-dependent accumulation of N$^\varepsilon$-(Carboxymethyl)lysine and N$^\varepsilon$-(Carboxymethyl)hydroxylysine in human skin collagen", Biochemistry, vol. 30, pp. 1205-1210, (1991).
Finco, A.B. et al., "Generation and characterization of monoclonal antibody against advanced glycation end products in chronic kidney disease", Biochemistry and Biophysics Reports, vol. 6, pp. 142-148, (2016).
International Search Report and Written Opinion dated Aug. 10, 2016 for PCT application No. PCT/US2016/034880.
Liu, H. et al., "Abstract 154: Vaccination using advanced glycation end product of low-density lipoprotein pulsed dendritic cells reduces atherosclerosis in diabetic apoe$^{-/-}$ mice", Arteriosclerosis, Thrombosis, and Vascular Biology, pp. 1-4, (2012).
Mashitah, M.W. et al., "Immunization of AGE-modified albumin inhibits diabetic nephropathy progression in diabetic mice", Diabetes, Metabolic Syndrome and Obesity: Targets and Therapy, vol. 8, pp. 347-355, (2015).
Sayej, W.N. et al., "Advanced glycation end products induce obesity and hepatosteatosis in CD-1 wild-type mice", BioMed Research International, vol. 6, No. 39, pp. 1-12, (2016).
Srikanth, V. et al., "Advanced glycation endproducts and their receptor RAGE in alzheimer's disease", Neurobiology of Aging, vol. 32, No. 5, pp. 763-777, (2011).
International Search Report and Written Opinion dated Dec. 2, 2016 for PCT application No. PCT/US2016/039076.
Fu, M-X. et al., "The advanced glycation end product, N-(Carboxymethyl)lysine, is a product of both lipid peroxidation and glycoxidation reactions", The Journal of Biological Chemistry, vol. 271, No. 17, pp. 9982-9986, (1996).
Jorgensen, L. et al., "The relationship between atherosclerosis of the thoracic aorta and renal scarring in an autopsy material", Acta Pathol Microbiol Immunol Scand A., vol. 93, No. 5, pp. 251-255, (1985) Abstract Only.
"Senescent cells drive plaque formation in animal models of atherosclerosis, research shows", Mayo Clinic, pp. 1-2, (2016), found at www.news-medical.net/news/20161027/Senescent-cells-drive-plaque-formation-in-animal-models-of-atherosclerosis-research-shows.aspx.
Baker, D.J. et al., "Naturally occurring p16$^{Ink4a}$-positive cells shorten healthy lifespan", Nature, vol. 530, issue 7589, pp. 184-189, (2016).
Raquib, R., "The key to youth via senescent cell removal", Young Investigators Review, pp. 1-4, (2017), found at sbyireview.com/2017/01/23/the-key-to-youth-via-senescent-cell-removal.
Tiner, S., "Mayo clinic research links senescent cells and atherosclerosis progression", Mayo Clinic News Network, pp. 1-3, (2016), found at newsnetwork.mayoclinic.org/discussion/mayo-clinic-research-links-senescent-cells-and-atherosclerosis-progression.
Wiley, C., "Aging Fundamentals: Cellular senescence", Science of Aging Blog at the Buck Institute, pp. 1-4, (2015), found at sage.buckinstitute.org/aging-fundamentals-cellular-senescence.
Arichika, S. et al., "Correlation of retinal arterial wall thickness with atherosclerosis predictors in type 2 diabetes without clinical retinopathy", British Journal of Ophthalmology, vol. 101, pp. 69-74, (2017).

(56) References Cited

OTHER PUBLICATIONS

Lin, Z. et al., "Vaccination against AGE-LDL significant attenuates atherosclerosis in diabetic apoe mice", Heart, vol. 97, No. 21, supplement 3, p. A18, (2011) Abstract Only.
Thompson, L.V., "Age-related muscle dysfunction", Experimental Gerontology, vol. 44, pp. 106-111, (2009).
Sun, K. et al., "Elevated serum carboxymethyl-Lysine, an advanced glycation end product, predicts severe walking disability in older women: The women's health and aging study I", Journal of Aging Research, vol. 2012, pp. 1-8, (2012).
Kislinger, T. et al., "$N^\varepsilon$-(Carboxymethyl)Lysine adducts of proteins are ligands for receptor for advanced glycation end products that activate cell signaling pathways and modulate gene expression", The Journal of Biological Chemistry, vol. 274, No. 44, pp. 31740-31749, (1999).
Nakayama, H. et al., "Production and characterization of antibodies to advanced glycation products on proteins", Biochemical and Biophysical Research Communications, vol. 162, No. 2, pp. 740-745, (1989).
Gupta, R.K., "Aluminum compounds as vaccine adjuvants", Advanced Drug Delivery Review, vol. 32, No. 3, pp. 155-172, (1998), Abstract Only.
Tracy, J.M. et al., "Preservatives for poliomyelitis (Salk) vaccine II: Formaldehyde and esters of p-hydroxybenzoic acid", Journal of Pharmaceutical Sciences, vol. 53, Issue 6, pp. 659-663, (1964), Abstract Only.
Koito, W. et al., "Conventional antibody against $N^\varepsilon$-(Carboxymethyl)Lysine (CML) shows cross-reaction to $N^\varepsilon$-(Carboxyethyl)Lysine (CEL): Immunochemical quantification of CML with a specific antibody", The Journal of Biochemistry, vol. 135, No. 6, pp. 831-837, (2004).
Product Description of "Anti-Advanced Glycation End Products (AGE), Carboxy-Methyl Lysine (CML) [6C7] Antibody", Kerafast, www.kerafast.com/product/1779/anti-advanced-glycation-end-products-age-carboxy-methyl-lysine-cml-6c7-antibody, printed on Feb. 2, 2017.
Ikeda, K. et al., "$N^\varepsilon$-(Carboxymethyl)lysine protein adduct is a major immunological epitope in proteins modified with advanced glycation end products of the maillard reaction", Biochemistry, vol. 35, No. 24, pp. 8075-8083, (1996).
Dunn, J.A. et al., "Oxidation of glycated proteins: Age-dependent accumulation of $N^\varepsilon$-(Carboxymethyl)lysine in lens proteins", Biochemistry, vol. 28, No. 24, pp. 9464-9468, (1989).
Peppa, M. et al., "The role of advanced glycation end products in the development of atherosclerosis", Current Diabetes Reports, vol. 4, pp. 31-36, (2004).
Glenn, J.V. et al., "The role of advanced glycation end products in retinal ageing and disease", Biochimica Et Biophysica Acta, vol. 1790, No. 10. pp. 1109-1116, (2009).
European Search Report dated Feb. 21, 2017 for EP application No. 16198527.0.
Xu, M. et al., "Transplanted senescent cells induce an osteoarthritis-like condition in mice", The Journals of Gerontology Series A: Biological Sciences and Medical Sciences, pp. 1-6, (2016).
Ratliff, M. et al., "In senescence, age-associated B cells secrete TNFα and inhibit survival of B-cell precursors", Aging Cell, vol. 12, pp. 303-311, (2013).
Manestar-Blazic, T. et al., "The dynamic of senescent cells accumulation can explain the age-specific incidence of autoimmune diseases", Medical Hypotheses, vol. 73, pp. 667-669, (2009).
Tchkonia, T. et al., "Fat tissue, aging, and cellular senescence", Aging Cell, vol. 9, pp. 667-684, (2010).
Robbins, P. et al., "Scripps research, Mayo Clinic scientists find new class of drugs that dramatically increases healthy lifespan", The Scripps Research Institute, pp. 1-3, found at www.scripps.edu/news/press/2015/20150309agingcell.html, printed on Mar. 14, 2015.
Dorr, J.R. et al., "Synthetic lethal metabolic targeting of cellular senescence in cancer therapy", Nature, vol. 501, No. 7467, pp. 421-425, (2013).
Xu, M. et al., "Targeting senescent cells enhances adipogenesis and metabolic function in old age", eLife, vol. 4, pp. 1-20, (2015).
Minamino, T. et al., "Endothelial cell senescence in human atherosclerosis: Role of telomere in endothelial dysfunction", Circulation, vol. 105, issue 13, pp. 1541-1544, (2002).
Takino, J-I. et al., "Cancer malignancy is enhanced by glyceraldehyde-derived advanced glycation end-products", Journal of Oncology, vol. 2010, pp. 1-8, (2010).
Laberge, R-M. et al., "Epithelial-mesenchymal transition induced by senescent fibroblasts", Cancer Microenvironment, vol. 5, pp. 39-44, (2012).
Abe, R. et al., "Regulation of human melanoma growth and metastasis by AGE-AGE receptor interactions", Journal of Investigative Dermatology, vol. 122, No. 2, pp. 461-467, (2004).
Porporato, P.E. et al., "A mitochondrial switch promotes tumor metastasis", Cell Reports, vol. 8, pp. 754-766, (2014).
Boquio, A. et al., "Reversible cell cycle inhibition and premature aging features imposed by conditional expression of $p16^{ink4a}$", Aging Cell, vol. 14, pp. 139-147, (2015).
Nelson, G. et al., "A senescent cell bystander effect: senescence-induced senescence", Aging Cell, vol. 11, pp. 345-349, (2012).
Rayess, H. et al., "Cellular senescence and tumor suppressor gene p16", International Journal of Cancer, vol. 130, No. 8, pp. 1715-1725, (2012).
Greenfieldboyce, N., "Boosting life span by clearing out cellular clutter", NPR.ORG, 4 pages, found at www.npr.org/sections/health-shots/2016/02/03/465354874/boosting-lifespan-by-clearing-out-cellular-clutter, printed on Feb. 4, 2016.
Matus, D.Q. et al., "Invasive cell fate requires G1 cell-cycle arrest and histone deacetylase-mediated changes in gene expression", Developmental Cell, vol. 35, pp. 162-174, (2015).
Stony Brook University, "Targeting invasive cells not dividing cells to halt cancer, study suggests", ScienceDaily, pp. 1-2, found at www.sciencedaily.com/releases/2015/10/151026181610.htm, (2015).
Liu, D. et al., "Senescent human fibroblasts increase the early growth of xenograft tumors via matrix metalloproteinase secretion", Cancer Research, vol. 67, No. 7, pp. 3117-3126, (2007).
Hoke, Z. "Belgian researchers discover way to block cancer metastasis", VOZ News, pp. 1-3, found at www.voanews.com/a/belgian-researchers-discover-way-to-block-cancer-metastasis/2453790.html, (2014).
Di, G-H. et al., "IL-6 secreted from senescent mesenchymal stem cells promotes proliferation and migration of breast cancer cells", PloS one, vol. 9, No. 11, pp. 1-15, (2014).
Huang, L-W. et al., "$P16^{ink4a}$ overexpression predicts lymph node metastasis in cervical carcinomas", Journal of Clinical Pathology, vol. 65, pp. 117-121, (2012).
Romagosa, C. et al., "$P16^{ink4a}$ overexpression in cancer: a tumor suppressor gene associated with senescence and high-grade tumors", Oncogene, vol. 30, pp. 2087-2097, (2011).
Terman, A. et al., "Mitochondrial turnover and aging of long-lived postmitotic cells: The mitochondrial-lysosomal axis theory of aging", Antioxidants & Redox Signaling, vol. 12, No. 4, pp. 503-535, (2010).
Ralph, A. et al., "P16 and HPV discordance in metastatic carcinoma of cervical lymph nodes of unknown primary", Clinical Case Reports, vol. 3, No. 10, pp. 817-818, (2015).
Hipkiss, A.R. "Aging, proteotoxicity, mitochondria, glycation, NAD+ and carnosine: possible inter-relationships and resolution of the oxygen paradox", Frontiers in Aging Neuroscience, vol. 2, article 10, pp. 1-6, (2010).
Bakala, H. et al., "Changes in rat liver mitochondria with aging Ion protease-like activity and $N^\varepsilon$-carboxymethyllysine accumulation in the matrix", European Journal of Biochemistry, vol. 270, No. 10, pp. 2295-2302, (2003).
Leslie, M. "Suicide of aging cells prolongs life span in mice", Sciencemag.org, pp. 1-4, found at www.sciencemag.org/news/2016/02/suicide-aging-cells-prolongs-life-span-mice, (2016).
Eto, H. et al., "Selective imaging of malignant ascites in a mouse model of peritoneal metastasis using in vivo dynamic nuclear polarization-magnetic resonance imaging", Analytical Chemistry, vol. 88, pp. 2021-2027, (2016).

(56) References Cited

OTHER PUBLICATIONS

May Jr. K.F. et al., "Anti-human CTLA-4 monoclonal antibody promotes T-cell expansion and immunity in a hu-PBL-SCID model: a new method for preclinical screening of costimulatory monoclonal antibodies", Blood, vol. 105, pp. 1114-1120, (2005).

Schmitt, C.A. "Cellular senescence and cancer treatment", Biochimica et Biophysica Acta—Reviews on Cancer, vol. 1775, No. 1, pp. 5-20, (2007).

Gordon, R.R. et al., "Cellular senescence and cancer chemotherapy resistance", Drug Resistance Updates, vol. 15, No. 1-2, pp. 123-131, (2012).

Eyman, D. et al., "CCL5 secreted by senescent aged fibroblasts induces proliferation of prostate epithelial cells and expression of genes that modulate angiogenesis", Journal of Cellular Physiology, vol. 220, No. 2, pp. 376-381, (2009).

Nguyen, D.X. et al., "Metastasis: from dissemination to organ-specific colonization", Nature Reviews Cancer, vol. 9, No. 4, pp. 274-284, (2009).

Smit, M.A. et al., "Deregulating EMT and senescence: Double impact by a single twist", Cancer Cell, pp. 5-7, (2008).

Degenhardt, T.P. et al., "Chemical modification of proteins by methylglyoxal", Cellular and Molecular Biology (Noisy-le-Grand, France), vol. 44, No. 7, pp. 1139-1145, (1998) Abstract Only.

Gao, S.H. et al., "Monoclonal antibody humanness score and its applications", BMC Biotechnology, vol. 13, No. 1, pp. 1-12, (2013).

ClinicalTrials.gov, "A study evaluating the safety of ABT-263 in combination with etoposide/cisplatin in subjects with cancer", ClinicalTrials.gov, 4 pages, found at https://clinicaltrials.gov/ct2/show/NCT00878449+48 term=A+study+evaluating+the+safety+of+ABT-263+in+combination+with+etoposide%2Fcisplatin+in+subjects+with+cancer&rank=1, printed on Aug. 4, 2016.

Keating, D.J. "Mitochondrial dysfunction, oxidative stress, regulation of exocytosis and their relevance to neurodegenerative diseases", vol. 104, No. 2, pp. 298-305, (2008). Abstract Only.

Sas, K. et al., "Mitochondria, metabolic disturbances, oxidative stress and the kynurenine system, with focus on neurodegenerative disorders", Journal of the neurological sciences, vol. 257, No. 1, pp. 221-239, (2007). Abstract Only.

Ott, M. et al., "Mitochondria, oxidative stress and cell death", Apoptosis, vol. 12, No. 5, pp. 913-922, (2007). Abstract Only.

Trushina, E. et al., "Oxidative stress and mitochondrial dysfunction in neurodegenerative diseases", Neuroscience, vol. 145, No. 4, pp. 1233-1248, (2007). Abstract Only.

Moreira, P.I. et al., "Lipoic acid and N-acetyl cysteine decrease mitochondrial-related oxidative stress in Alzheimer disease patient fibroblasts", Journal of Alzheimer's Disease, vol. 12, No. 2, pp. 195-206, (2007). Abstract Only.

Yel, L. et al., "Thimerosal induces neuronal cell apoptosis by causing cytochrome c and apoptosis-inducing factor release from mitochondria", International Journal of Molecular Medicine, vol. 16, No. 6, pp. 971-977, (2005). Abstract Only.

Humphrey, M.L. et al., "Mitochondrial mediated thimerosal-induced apoptosis in a human neuroblastoma cell line (SK-N-SH)", Neurotoxicology, vol. 26, No. 3, pp. 407-416, (2005). Abstract Only.

Makani, S. et al., "Biochemical and molecular basis of thimerosal-induced apoptosis in T cells: a major role of mitochondrial pathway", Genes and Immunity, vol. 3, No. 5, pp. 270-278, (2002). Abstract Only.

Freitag, H. et al., "Inhibition of malate transport and activation of phosphate transport in mitochondria by ethylmercurithiosalicylate", FEBS Letters, vol. 117, No. 1, pp. 149-151, (1980). Citation Only.

Freitag, H. et al., "Ethylmercurithiosalicylate—a new reagent for the study of phosphate transport in mitochondria", FEBS Letters, vol. 114, No. 2, pp. 295-298, (1980). Citation Only.

Windham, G.C. et al., "Autism spectrum disorders in relation to distribution of hazardous air pollutants in the San Francisco bay area", Environmental Health Perspectives, pp. 1438-1444, (2006). Citation Only.

Ooe, H. et al., "Induction of reactive oxygen species by bisphenol A and abrogation of bisphenol A-induced cell injury by DJ-1", Toxicological Sciences, vol. 88, No. 1, pp. 114-126, (2005). Abstract Only.

Hanzel, C.E. et al., "Thallium induces hydrogen peroxide generation by impairing mitochondrial function", Toxicology and Applied Pharmacology, vol. 216, No. 3, pp. 485-492, (2006). Abstract Only.

Murugavel, P. et al., "Cadmium induced mitochondrial injury and apoptosis in vero cells: protective effect of diallyl tetrasufide from garlic", The International Journal of Biochemistry & Cell Biology, vol. 39, No. 1, pp. 161-170, (2007). Abstract Only.

Lasfer, M. et al., "Cadmium induces mitochondria-dependent apoptosis of normal human hepatocytes", Cell Biology and Toxicology, vol. 24, No. 1, pp. 55-62, (2008). Abstract Only.

Gash, D.M. et al., "Trichloroethylene: Parkinsonism and complex 1 mitochondrial neurotoxicity", Annals of neurology, vol. 63, No. 2, pp. 184-192, (2008). Abstract Only.

Banerjee, N. et al., "Arsenic-induced mitochondrial instability leading to programmed cell death in the exposed individuals", Toxicology, vol. 246, No. 2, pp. 101-111, (2008). Abstract Only.

Partridge, M.A. et al., "Arsenic induced mitochondrial DNA damage and altered mitochondrial oxidative function: Implication for genotoxic mechanisms in mammalian cells", Cancer Research, vol. 67, No. 11, pp. 5239-5247, (2007). Abstract Only.

Santra, A. et al., "Arsenic induces apoptosis in mouse liver is mitochondria dependent and is abrogated by N-acetylcysteine", Toxicology and Applied Pharmacology, vol. 220, No. 2, pp. 146-155, (2007). Abstract Only.

Bouchard, H. et al., "Antibody-drug conjugates—A new wave of cancer drugs", Bioorganic & Medicinal Chemistry Letters, vol. 24, pp. 5357-5363, (2014).

Yang, H.M. et al., "Doxorubicin conjugated with a monoclonal antibody directed to a human melanoma-associated proteoglycan suppresses the growth of established tumor xenografts in nude mice", Proceeding of the National Academy of Science, vol. 85, pp. 1189-1193, (1988).

Childs, B.G. et al., "Senescent intimal foam cells are deleterious at all stages of atherosclerosis", Science, vol. 354, No. 6311, pp. 472-477, (2016).

Loaiza, N. et al., "Cellular senescence and tumor promotion: Is aging the key?", Biochimica et Biophysica Acta, vol. 1865, pp. 155-167, (2016).

Rodier, F. et al., "Four faces of cellular senescence", The Journal of Cell Biology, vol. 192, No. 4, pp. 547-556, (2011).

Shay, J.W. et al., "Hallmarks of senescence in carcinogenesis and cancer therapy", Oncogene, vol. 23, pp. 2919-2933, (2004).

Davalos, A.R. et al., "Senescent cells as a source of inflammatory factors for tumor progression", Cancer Metastasis Reviews, vol. 29, pp. 273-283, (2010).

Roninson, I.B., "Tumor cell senescence in cancer treatment", Cancer Research, vol. 63, pp. 2705-2715, (2003).

International Search Report and Written Opinion dated May 17, 2017 for PCT application No. PCT/US2017/018185.

Kobayashi, S. et al., "Overproduction of N(epsilon)-(carboxymethyl) lysine-induced neovascularization in cultured choroidal explant of aged rat", Biological & Pharmaceutical Bulletin, vol. 30, No. 1, pp. 133-138, (2007).

Foster, D. et al., "AGE metabolites: A biomarker linked to cancer disparity?" Cancer Epidemiology, Biomarkers and Prevention, vol. 23, No. 10, pp. 2186-2191, (2014).

Mir, A.R. et al., "Structural changed in histone H2A by methylglyoxal generate highly immunogenic amorphous aggregates with implications in auto-immune response in cancer", Glycobiology, vol. 26, No. 2, pp. 129-141, (2016).

Ko, S-Y. et al., "Cell migration is regulated by AGE-RAGE interaction in human oral cancer cells in vitro", PLOS One, vol. 9, No. 10, pp. 1-9, (2014).

Chen, H. et al., "Advanced glycation end products increase carbohydrate responsive element binding protein expression and promote cancer cell proliferation", Molecular and Cellular Endocrinology, vol. 395, No. 1-2, pp. 69-78, (2014).

(56) References Cited

OTHER PUBLICATIONS

Mercado-Pimentel, M.E. et al., "The S100P/RAGE signaling pathway regulates expression of microRNA-21 in colon cancer cells", FEBS Letters, vol. 589, No. 18, pp. 2388-2393, (2015).
Product description, "Carboxymethyl Lysine Antibody", R&D Systems, a biotechne brand, catalog No. MAB3247, 1 page, found at https://resources.rndsystems.com/pdfs/datasheets/mab3247.pdf, (2015).
Bhat, R. et al., "Astrocyte senescence as a component of Alzheimer's Disease", PLOS One, vol. 7, No. 9, pp. 1-10, (2012).
Flanary, B.E. et al., "Evidence that aging and amyloid promote microglial cell senescence", Rejuvenation Research, vol. 10, No. 1, pp. 61-74, (2007).
Takeda, A. et al., "Advanced glycation end products co-localize with astrocytes and microglial cells in Alzheimer's disease brain", Acta Neuropathologica, vol. 95, pp. 555-558, (1998).
Chinta, S.J. et al., "Environmental stress, ageing and glial cell senescence: a novel mechanistic link to Parkinson's disease?", Journal of Internal Medicine, vol. 273, pp. 429-436, (2013).
Mori, M., "The Parkinsonian Brain: Cellular senescence and neurodegeneration", SAGE, found at sage.buckinstitute.org/the-parkinsonian-brain-cellular-senescence-and-neurodegeneration, (2015).
Das, M.M. et al., "Astrocytes show reduced support of motor neurons with aging that is accelerated in a rodent model of ALS", Neurobiology of Aging, vol. 36, pp. 1130-1139, (2015).
Luessi, F. et al., "Neurodegeneration in multiple sclerosis: novel treatment strategies", Expert Rev. Neurother., vol. 9, pp. 1061-1077, (2012).
Wright, W.E., "Myoblast senescence in Muscular Dystrophy", Exp Cell Research, vol. 157, pp. 343-354, (1985).
King, O.D., et al., "The tip of the iceberg: RNA-binding proteins with prion-like domains in neurodegenerative disease", Brain Research, vol. 1462, pp. 61-80, (2012).
Dobson, D.M., "The structural basis of protein folding and its links with human disease", Philosophical Transactions of the Royal Society of London B: Biological Sciences, vol. 356, No. 1406, pp. 133-145, (2001).
Kato, S. et al., "Advanced glycation endproduct-modified superoxide dismutase-1 (SOD1)-positive inclusions are common to familial amyotrophic lateral sclerosis patients with SID1 gene mutations and transgenic mice expressing human SOD1 with a G85R mutation", Acta Neuropathologica, vol. 100, pp. 490-505, (2000).
U.S. Appl. No. 10/358,502, filed Jul. 2019, Gruber.
Haslbeck, K.M. et al., "The RAGE pathway in inflammatory myopathies and limb girdle muscular dystrophy", Acta Neuropatholoooica, vol. 110, issue 3, pp. 247-254, (2005).
Sternberg, Z. et al., "AGE-RAGE in multiple sclerosis brain", Immunological Investigations, vol. 40, issue 2, pp. 197-205 (2011).
Miyata, T. et al., "Increased pentosidine, an advanced glycation end product, in plasma and synovial fluid from patients with rheumatoid arthritis and its relation with inflammatory markers", Biochemical and Biophysical Research Communications, vol. 244, pp. 45-49, (1998).
Mulrennan: S. et ai., "The role of receptor for advanced glycation end products in airway inflammation in CF and CF related diabetes", Scientific Reports: vol. 5, No. 8931, pp. 1-9, (2016).
Weber, K. et al., "Distribution of advanced glycation end products in the cerebellar neurons of dogs", Brain Research, vol. 791, pp. 11-17, (1998).
Berg, T.J. et al., "The advanced glycation end product Nε-(carboxymethyl)lysine is increased in serum from children and adolescents with type 1 diabetes", Diabetes Care; vol. 21, No. 11; pp. 1997-2002, (1998).
Degenhardt, T.P. et al., "The serum concentration of the advanced glycation end-product Nε-(carboxymethyl)lysine is increased in uremia", Kidney International, vol. 52, pp. 1064-1067, (1997).
Hayase, F. et al., "Aging of proteins: Immunological detection of a glucose-derived pyrrole formed during maillard reaction in vivo", The Journal of Biological Chemistry, vol 263, No. 7, pp. 3758-3764, (1989).
Ikeda, K. et al., "Immunochemical approaches to AGE-structures: characterization of anti-AGE antibodies", The Maillard Reaction in Foods and Medicine, pp. 310-315, (1998).
Kume, S. et al., "Immunohistochemical and ultrastructural detection of advanced glycation end products in atherosclerotic lesions of human aorta with a novel specific monoclonal antibody", American Journal of Pathology, vol. 147, No. 3, pp. 654-667, (1995).
Makita, A. et al., "Immunochemical detection of advanced glycosylation end products in vivo", The Journal of Biological Chemistry, vol. 267, No. 8, pp. 5133-5138, (1992).
Niwa, T. et al., "Immunohistochemical detection of advanced giycation end products in dialysis-related amyloidosis", Kidney International, vol. 48, pp. 771-778, (1995).
Papanastasiou, P. et al., "Immunological quantification of advanced glycosylation end products in the serum of patients on hemodialysis of CAPD", Kidney International, vol. 46, pp. 216-222, (1994).
Schleicher, E.D. et al., "Increased accumulation of the glycoxidation product N(epsilon)-(Carboxymethyl)lysine in human tissues in diabetes and aging", The Journal of Clinical Investigation. vol. 99, No. 3, pp. 457-468, (1997).
Takeuchi, M. et al., "Immunological detection of a novel advanced glycation end-product", Molecular Medicine, vol. 7, No. 11, pp. 783-791, (2001).
Kobayashi, S. et al., "Nε-(Carboxymethyl)lysine-induced choroidal angiogenic potential facilitates retinal neovascularization in advanced-diabetic rat in vitro", The Open Pharmacology Journal vol. 2, pp. 79-85, (2008).
Tamemoto, H. et al., "AGE inhibitor-recent development", Diabetes Frontier, vol. 16, No. 5, pp. 541-546, (2005).
Nagai, R. et al., "Prevention of diabetic complication by AGE inhibitors", Progress of Medicine, vol. 207, No. 9, pp. 663-667, (2003).
Vistoli, G. et al., "Advanced glycoxidation and lipoxidation end products (AGEs and ALEs): an overview of their mechanisms of formation", Free Radical Research, vol. 47, supple. 1, pp. 3-27, (2013).
Bachmeier, B.E. et al., "Maillard products as biomarkers in cancer", Annals of the New York Academy of Sciences, vol. 1126, No. 1, pp. 283-287, (2008). Abstract Only.
Chen, Z. et al., "Senescent cells re-engineered to express soluble programmed death receptor-1 for inhibiting programmed death receptor-1/programmed death ligand-1 as a vaccination approach against breat cancer", Cancer Science, vol. 109, pp. 1753-1763. (2018).
Leontieva, O.V. et al., "Yeast-like chronological senescence in mammalian cells: phenomenon, mechanism and pharmacological supression", Aging, vol. 3, No. 11, pp. 1-14, (2011).
Moser, A.C. et al., "Immunoaffinity chromatography: an introduction to applications and recent developments", Bioanalysis, vol. 2, No. 4, pp. 769-790, (2010).
Prosser, C.G. et al., "Nε-carboxymethyllysine in nutritional milk formulas for infants", Food Chemistry, vol. 274, pp. 886-890, (2019).
Takeuchi, M. et al., "Detection of noncarboxymethyllysine and carboxymethyllysine advanced glycation end products (AGE) in serum of diabetic patients", Molecular Medicine, vol. 5, pp. 393. 405, (1999).
Teodorowicz, M. et al., Immunomodulation by processed animal feed: The role of maillard reaction products and advanced glycation end-products (AGEs), Frontiers in Immunology, vol. 9, article 2088, pp. 1-15, (2018).
Kwak, T. et al., "Targeting of RAGE-ligand signaling impairs breast cancer cell invasion and metastasis", Oncogene, vol. 11, pp. 1559-1572, (2017), Abstract Only.
Inui, H. et al., "A scFv antibody-based immunoaffinity chromatography column for clean-up of bisphenol a-contaminated water samples", Journal of Agricultural and Food Chemistry, vol. 57, No. 2, pp. 353-358, (2009), Abstract Only.
R179, 5 pages, Mar. 31, 2019, 2017086871, JP.
R180, 14 pages, Apr. 8, 2019, 2017113349, RU.
R181, 3 pages, Jun. 7, 2019, U.S. Appl. No. 14/932,200, US.
R182, 9 pages, Jul. 1, 2019, 2017-515740, JP.
R183, 24 pages, Aug. 15, 2019, U.S. Appl. No. 14/920,737, US.

(56) References Cited

OTHER PUBLICATIONS

R184, 15 pages, Jun. 19, 2019, 18184822.7, EP.
R186, 144 pages, Jul. 19, 2019, 17708098.3. EP.
U.S. Appl. No. 16/440,747, dated Jun. 13, 2019.
International Search Report and Written Opinion dated Nov. 25, 2019 for PCT application No. PCT/US2019/047762.
Dillon, P., "Focused ultrasound and pembrolizumab in metastatic breast cancer (breast-48)", ClinicalTrials.gov, pp. 1-7. (2017).
Masui, T. et al., "Low-intensity ultrasound enhances the anticancer activity of cetuximab in human head and neck cancer cells", Experimental and Therapeutic Medicine, vol. 5, pp. 11-16, (2013).
Khaibullina, A. et al., "Pulsed high-intensity focused ultrasound enhances uptake of radiolabeled monoclonal antibody to human epidermoid tumor in nude mice", The Journal of Nuclear Medicine, vol. 49, pp. 295-302, (2008).
Liao, A-H. et al., "Enhanced therapeutic epidermal growth factor receptor (EGFR) antibody delivery via pulsed ultrasound with targeting microbubbles for glioma treatment", Journal of Medical and Biological Engineering, vol. 35, pp. 156-164, (2015).
Liu, H-L. et al., "Focused ultrasound enhances central nervous system delivery of bevacizumab for malignant glioma treatment", Radiology, vol. 281, No. 1, pp. 99-108, (2016).
Kobus, T. et al., "Growth inhibition in a brain metastasis model by antibody delivery using focused ultrasound-mediated blood-brain barrier disruption", Journal of Controlled Release, vol. 238, pp. 281-288, (2016).
R202, 38 pages, Oct. 30, 2019, U.S. Appl. No. 15/720,912, US.
R203, 4 pages, Nov. 1, 2019, U.S. Appl. No. 15/863,811, US.
R204, 12 pages, Nov. 14, 2019, PCT/US2018/030931, WO.
R205, 28 pages, Nov. 20, 2019, U.S. Appl. No. 14/932,200, US.
R206, 3 pages, Nov. 21, 2019, U.S. Appl. No. 15/863,784, US.
R210, 63 pages, Dec. 5, 2019, U.S. Appl. No. 15/863,741, US.
R211, 8 pages, Dec. 11, 2019, U.S. Appl. No. 15/977,587, US.
R212, 3 pages, Dec. 11, 2019, 18726656.4, EP.
R213, 3 pages, Dec. 20, 2019, U.S. Appl. No. 15/863,828, US.

* cited by examiner

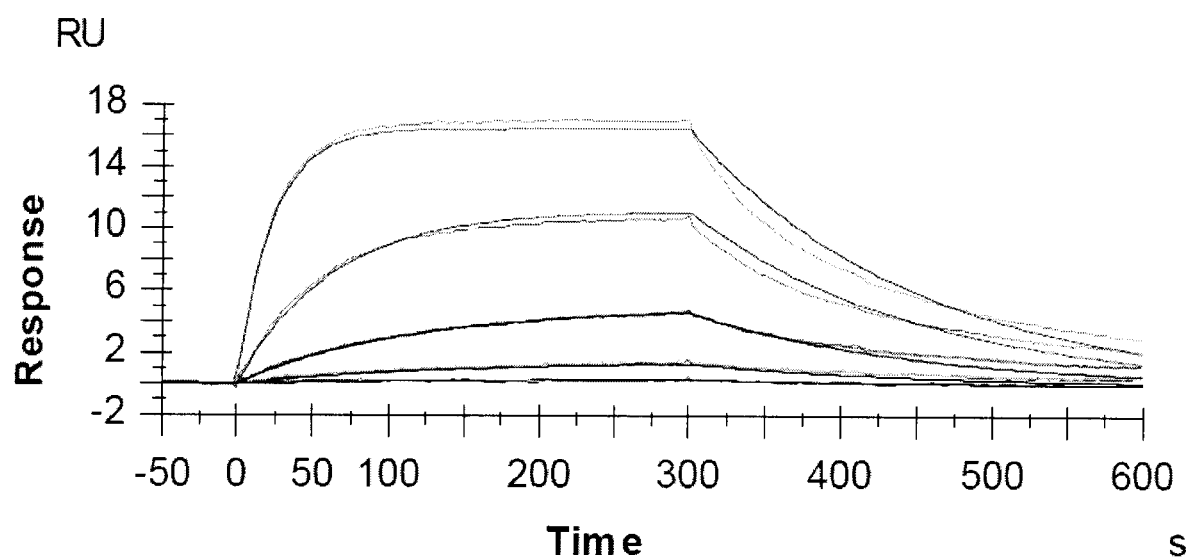

ANTI-AGE ANTIBODIES FOR TREATING INFLAMMATION AND AUTO-IMMUNE DISORDERS

BACKGROUND

Chronic inflammation is associated with a variety of diseases, including Alzheimer's disease, diabetes, atherosclerosis, and cancer. Autoimmune diseases, such as osteoarthritis and Crohn's disease are also associated with chronic inflammation. Chronic inflammation may be characterized by the presence of pro-inflammatory factors at levels higher than baseline near the site of pathology, but many fold lower than those found in acute inflammation. Examples of these factors include TNF, IL-1α, IL-1β, IL-5, IL-6, IL-8, IL-12, IL-23, CD2, CD3, CD20, CD22, CD52, CD80, CD86, C5 complement protein, BAFF, APRIL, IgE, α4β1 integrin and α4β7 integrin. Treatments of diseases associated with chronic inflammation include treatments which interfere with the action of pro-inflammatory factors, such as by binding the factors or binding to receptors for the factors.

An important class of drug for the treatment of chronic inflammation and the diseases associate with chronic inflammation include anti-inflammation antibodies. This class of drugs not only includes antibodies, but also other proteins that bind to pro-inflammatory factors or pro-inflammatory factor receptors, and include a constant region of antibody. Examples of anti-inflammation antibodies include abatacept, alefacept, alemtuzumab, atacicept, belimumab, canakinumab, eculizumab, epratuzumab, natalizumab, ocrelizumab, ofatumumab, omalizumab, otelixizumab, rituximab, teplizumab, vedolizumab, adalimumab, briakinumab, certolizumab pegol, etanercept, golimumab, infliximab, mepolizumab, reslizumab, tocilizumab and ustekinumab.

Senescent cells are cells in a state of irreversible proliferative arrest. Senescence is a distinct state of a cell, and is associated with biomarkers, such as activation of p16$^{Ink4a}$, and expression of β-galactosidase. Senescent cells are also associated with secretion of many factors involved in intercellular signaling, including pro-inflammatory factors; secretion of these factors has been termed the senescence-associated secretory phenotype, or SASP.

Advanced glycation end-products (AGEs; also referred to AGE-modified proteins, or glycation end-products) arise from a non-enzymatic reaction of sugars with protein side-chains in aging cells (Ando, K. et al., Membrane Proteins of Human Erythrocytes Are Modified by Advanced Glycation End Products during Aging in the Circulation, *Biochem Biophys Res Commun.*, Vol. 258, 123, 125 (1999)). This process begins with a reversible reaction between the reducing sugar and the amino group to form a Schiff base, which proceeds to form a covalently-bonded Amadori rearrangement product. Once formed, the Amadori product undergoes further rearrangement to produce AGEs. Hyperglycemia, caused by diabetes mellitus (DM), and oxidative stress promote this post-translational modification of membrane proteins (Lindsey J B, et al., "Receptor For Advanced Glycation End-Products (RAGE) and soluble RAGE (sRAGE): Cardiovascular Implications," *Diabetes Vascular Disease Research*, Vol. 6(1), 7-14, (2009)). AGEs have been associated with several pathological conditions including diabetic complications, inflammation, retinopathy, nephropathy, atherosclerosis, stroke, endothelial cell dysfunction, and neurodegenerative disorders (Bierhaus A, "AGEs and their interaction with AGE-receptors in vascular disease and diabetes mellitus. I. The AGE concept," Cardiovasc Res, Vol. 37(3), 586-600 (1998)).

AGE-modified proteins are also a marker of senescent cells. This association between glycation end-product and senescence is well known in the art. See, for example, Gruber, L. (WO 2009/143411, 26 Nov. 2009), Ando, K. et al. (Membrane Proteins of Human Erythrocytes Are Modified by Advanced Glycation End Products during Aging in the Circulation, *Biochem Biophys Res Commun.*, Vol. 258, 123, 125 (1999)), Ahmed, E. K. et al. ("Protein Modification and Replicative Senescence of WI-38 Human Embryonic Fibroblasts" *Aging Cells*, vol. 9, 252, 260 (2010)), Vlassara, H. et al. (Advanced Glycosylation Endproducts on Erythrocyte Cell Surface Induce Receptor-Mediated Phagocytosis by Macrophages, *J. Exp. Med., Vol.* 166, 539, 545 (1987)) and Vlassara et al. ("High-affinity-receptor-mediated Uptake and Degradation of Glucose-modified Proteins: A Potential Mechanism for the Removal of Senescent Macromolecules" *Proc. Natl. Acad. Sci. USAI*, Vol. 82, 5588, 5591 (1985)). Furthermore, Ahmed, E. K. et al. indicates that glycation end-products are "one of the major causes of spontaneous damage to cellular and extracellular proteins" (Ahmed, E. K. et al., see above, page 353). Accordingly, the accumulation of glycation end-product is associated with senescence and lack of function.

SUMMARY

In a first aspect, the present invention is a composition for treating inflammation or auto-immune disorders, comprising: (i) an antibody that binds to an AGE-modified protein on a cell, and (ii) an anti-inflammation antibody.

In a second aspect, the present invention is a method of treating inflammation or autoimmune disorders, comprising administering an antibody that binds to an AGE-modified protein on a cell.

In a third aspect, the present invention is a method of treating inflammation or auto-immune disorders, comprising interfering with the activity of a pro-inflammatory factor, and killing senescent cells.

Definitions

The term "advanced glycation end-products" or "AGE-modified protein" (also referred to as "glycation end-products") refers to modified proteins that are formed as the result of the reaction of sugars with protein side chains that further rearrange and form irreversible crosslinking. This process begins with a reversible reaction between the reducing sugar and the amino group to form a Schiff base, which proceeds to form a covalently-bonded Amadori rearrangement product. Once formed, the Amadori product undergoes further rearrangement to produce AGEs. AGE-modified proteins, and antibodies to AGE-modified proteins are described in U.S. Pat. No. 5,702,704 (Bucala) and U.S. Pat. No. 6,380,165 (Al-Abed et al.). Epitopes found on glycated proteins, such as N-deoxyfructosyllysine found on glycated albumin, are not AGEs. Examples of AGEs include 2-(2-furoyl)-4(5)-(2-furanyl)-1H-imidazole ("FFI"); 5-hydroxymethyl-1-alkylpyrrole-2-carbaldehyde ("Pyrraline"); 1-alkyl-2-formyl-3,4-diglycosyl pyrrole ("AFGP"), a non-fluorescent model AGE; carboxymethyllysine; and pentosidine. ALI, another AGE, is described in Al-Abed et al.

"An antibody that binds to an AGE-modified protein on a cell" means an antibody or other protein that binds to an AGE-modified protein and includes a constant region of an antibody, where the protein which has been AGE-modified is a protein normally found bound on the surface of a cell, preferably a mammalian cell, more preferably a human, cat, dog, horse, camelid (for example, camel or alpaca), cattle, sheep, or goat cell. AGE-modified albumin is not an AGE-modified protein on a cell, because albumin is not a protein normally found bound on the surface of cells. "An antibody that binds to an AGE-modified protein on a cell" only includes those antibodies which lead to removal, destruction, or death of the cell. Also included are antibodies which are conjugated, for example to a toxin, drug, or other chemical or particle. Preferably, the antibodies are monoclonal antibodies, but polyclonal antibodies are also possible.

"Pro-inflammatory factor" means a factor which promotes inflammation. Examples of pro-inflammatory factors include TNF or TNFα, IL-1α, IL-1β, IL-5, IL-6, IL-8, IL-12, IL-23, CD2, CD3, CD20, CD22, CD52, CD80, CD86, C5 complement protein, BAFF, APRIL, IgE, α4β1 integrin and α4β7 integrin. Many of these factors and/or their receptors may have a different structure in different animals. A small letter preceding the name will be used to designate that factor originating from different animals or humans, as follows: humans=h, cats=f, dogs=d, horses=e, camels (or alpaca)=c, cattle=b, sheep=o, and goats=g; for example hTNF means human TNF. Furthermore, an "R" following the name of the factor represents the receptor for the factor, such as TNF-R being the human receptor for TNF, or IL-6R being the receptor for IL-6. These designations may be used in combination, for example hIL-6R being the human receptor for IL-6.

"Anti-inflammation antibody" means an antibody or other protein that binds to a pro-inflammatory factor or pro-inflammatory factor receptor, reduces the activity of the factor or receptor, and includes a constant region of antibody. Examples of anti-inflammation antibodies include abatacept, alefacept, alemtuzumab, atacicept, belimumab, canakinumab, eculizumab, epratuzumab, natalizumab, ocrelizumab, ofatumumab, omalizumab, otelixizumab, rituximab, teplizumab, vedolizumab, adalimumab, briakinumab, certolizumab pegol, etanercept, golimumab, infliximab, mepolizumab, reslizumab, tocilizumab and ustekinumab. Preferably, the antibodies are monoclonal antibodies, but polyclonal antibodies are also possible.

"Senescent cell" means a cell which is in a state of irreversible proliferative arrest and expresses one or more biomarkers of senescence, such as activation of p16$^{Ink4a}$, or expression of β-galactosidase. Also included are cells which expresses one or more biomarkers of senescence, do not proliferate in vivo, but may proliferate in vitro under certain conditions, such as some satellite cells found in the muscles of ALS patients.

BRIEF DESCRIPTION OF THE DRAWINGS

FIG. 1 illustrates a graph of the maximum binding capacity (RU) versus time for the test antibody of Example 1.

DETAILED DESCRIPTION

Although senescent cells have been studied for some time, the in vivo effects of senescent cells have only recently been carried out. Once recent study, by Baker, D. J. et al. ("Clearance of p16Ink4a-positive senescent cells delays ageing-associated disorders", Nature, vol. 479, pp. 232-236, (2011)), examined the effects of clearance of senescent cells in mice. However, the effect on inflammation and pro-inflammatory factors was not noted. Prior to the present application, the effects of removal or killing of senescent cells on inflammation and pro-inflammatory factors, was unknown.

The present invention is based on the recognition that many cellular networks associated with inflammation have a positive feedback component. Because senescent cells produce pro-inflammatory factors, removal of these cells alone, produces a profound reduction in inflammation and the amount and concentration of pro-inflammatory factors. This may be done by administering an antibody that binds to an AGE-modified protein on a cell.

Furthermore, by coupling the reduction of the activity of pro-inflammatory factors, together with a reduction in the number of senescent cells, a synergistic effect is produced: the reduction in inflammation will be greater than what would have been expected, based on the effects of either component alone. This may be done, for example, by the administration of both an anti-inflammation antibody and an antibody that binds to an AGE-modified protein on a cell.

An antibody that binds to an AGE-modified protein on a cell (or "Anti-AGE antibody") is known in the art. Examples include those described in U.S. Pat. No. 5,702,704 (Bucala) and U.S. Pat. No. 6,380,165 (Al-Abed et al.). Examples include an antibody that binds to one or more AGEs, such as FFI, pyrraline, AFGP, ALI, carboxymethyllysine and pentosidine. Preferably, the antibody binds carboxymethyllysine. Preferably, the antibody is non-immunogenic to the animal in which it will be used, such as non-immunogenic to humans; companion animals including cats, dogs and horses; and commercially important animals, such camels (or alpaca), cattle (bovine), sheep, and goats. More preferably, the antibody has the same species constant region as antibodies of the animal to reduce the immune response against the antibody, such as being humanized (for humans), felinized (for cats), caninized (for dogs), equuinized (for horses), camelized (for camels or alpaca), bovinized (for cattle), ovinized (for sheep), or caperized (for goats). Most preferably, the antibody is identical to that of the animal in which it will be used (except for the variable region), such as a human antibody, a cat antibody, a dog antibody, a horse antibody, a camel antibody, a bovine antibody, a sheep antibody or a goat antibody. Details of the constant regions and other parts of antibodies for these animals are described below.

The anti-AGE antibody has low rate of dissociation from the antibody-antigen complex, or $k_d$ (also referred to as $k_{back}$ or off-rate), preferably at most $9\times10^{-3}$, $8\times10^{-3}$, $7\times10^{-3}$ or $6\times10^{-3}$ (sec$^{-1}$). The anti-AGE antibody has a high affinity for the AGE-modified protein of a cell, which may be expressed as a low dissociation constant $K_D$ of at most $9\times10^{-6}$, $8\times10^{-6}$, $7\times10^{-6}$, $6\times10^{-6}$, $5\times10^{-6}$, $4\times10^{-6}$ or $3\times10^{-6}$ (M).

The anti-AGE antibody can be conjugated to an agent that causes the destruction of AGE-modified cells. Such agents may be a toxin, a cytotoxic agent, magnetic nanoparticles, and magnetic spin-vortex discs.

A toxin, such as pore-forming toxins (PFT) (Aroian R. et al., "Pore-Forming Toxins and Cellular Non-Immune Defenses (CNIDs)," *Current Opinion in Microbiology*, 10:57-61 (2007)), conjugated to an anti-AGE antibody may be injected into a patient to selectively target and remove AGE-modified cells. The anti-AGE antibody recognizes and binds to AGE-modified cells. Then, the toxin causes pore formation at the cell surface and subsequent cell removal through osmotic lysis.

Magnetic nanoparticles conjugated to the anti-AGE antibody may be injected into a patient to target and remove AGE-modified cells. The magnetic nanoparticles can be heated by applying a magnetic field in order to selectively remove the AGE-modified cells.

As an alternative, magnetic spin-vortex discs, which are magnetized only when a magnetic field is applied to avoid self-aggregation that can block blood vessels, begin to spin when a magnetic field is applied, causing membrane disruption of target cells. Magnetic spin-vortex discs, conjugated to anti-AGE antibodies specifically target AGE-modified cell types, without removing other cells.

Antibodies typically comprise two heavy chains and two light chains of polypeptides joined to form a "Y" shaped molecule. The constant region determines the mechanism used to target the antigen. The amino acid sequence in the tips of the "Y" (the variable region) varies among different antibodies. This variation gives the antibody its specificity for binding antigen. The variable region, which includes the ends of the light and heavy chains, is further subdivided into hypervariable (HV—also sometimes referred to as complementarity determining regions, or CDRs) and framework (FR) regions. When antibodies are prepared recombinantly, it is also possible to have a single antibody with variable regions (or complementary determining regions) that bind to two different antigens, with each tip of the "Y" being specific to each antigen; these are referred to as bi-specific antibodies.

A humanized anti-AGE antibody according to the present invention may have the following human constant region sequence of amino acids:

```
           10          20          30          40
    ASTKGPSVFP  LAPCSRSTSE  STAALGCLVK  DYFPEPVTVS 50          60          70          80
    WNSGALTSGV  HTFPAVLQSS  GLYSLSSVVT  VPSSNFGTQT 90         100         110         120
    YTCNVDHKPS  NTKVDKTVER  KCCVECPPCP  APPVAGPSVF 130         140         150         160
    LFPPKPKDTL  MISRTPEVTC  VVVDVSHEDP  EVQFNWYVDG 170         180         190         200
    VEVHNAKTKP  REEQFNSTFR  VVSVLTVVHQ  DWLNGKEYKC 210         220         230         240
    KVSNKGLPAP  IEKTISKTKG  QPREPQVYTL  PPSREEMTKN 250         260         270         280
    QVSLTCLVKG  FYPSDISVEW  ESNGQPENNY  KTTPPMLDSD 290         300         310         320
    GSFFLYSKLT  VDKSRWQQGN  VFSCSVMHEA  LHNHYTQKSL

SLSPGK
```

The anti-AGE antibody may have one or more of the following complementarity determining regions:

```
    CDR1H (heavy Chain):    SYTMGVS

CDR2H (heavy Chain):    TISSGGGSTYYPDSVKG

CDR3H (heavy Chain):    QGGWLPPFAX

CDR1L (Light Chain):    RASKSVSTSSRGYSYMH

CDR2L (Light Chain):    LVSNLES

CDR3L (Light Chain):    QHIRELTRS
```

Anti-inflammation antibodies are well known, and many have already been approved for human use. Examples of anti-inflammation antibodies include abatacept, alefacept, alemtuzumab, atacicept, belimumab, canakinumab, eculizumab, epratuzumab, natalizumab, ocrelizumab, ofatumumab, omalizumab, otelixizumab, rituximab, teplizumab, vedolizumab, adalimumab, briakinumab, certolizumab pegol, etanercept, golimumab, infliximab, mepolizumab, reslizumab, tocilizumab and ustekinumab. Preferably, the anti-inflammation antibody is an antibody that binds to TNF or TNF-R. Any of the above antibodies may be modified to reduce any possible immune reaction in animals other than humans, by replacing the portion which does not bind a pro-inflammatory factor or pro-inflammatory factor receptor which the constant region of an antibody which originates from that animal, such as an antibody constant region of cats, dogs, horses, camels (or alpaca), cattle, sheep, or goats. Such constant regions, as well as other portions of the antibodies of these animals are well known, and some may be found in the following: Yaofeng Zhao, et al. "The bovine antibody repertoire" Developmental & Comparative Immunology, Vol. 30, Issues 1-2, 2006, Pages 175-186; Wagner B, et al. "the complete map of the Ig heavy chain constant gene region reveals evidence for seven IgG isotypes and for IgD in the horse" J Immunol. 2004 Sep. 1; 173(5):3230-42; Strietzel C J, et al. "In Vitro functional characterization of feline IgGs" Vet Immunol Immunopathol. 2014 Apr. 15; 158(3-4):214-23; Mayuri Patel, et al. "Sequence of the dog immunoglobulin alpha and epsilon constant region genes" Immunogenetics, March 1995, Volume 41, Issue 5, pp 282-286; and David R. Maass, et al. "Alpaca (*Lama pacos*) as a convenient source of recombinant camelid heavy chain antibodies (VHHs)" J Immunol Methods. Jul 31, 2007; 324(1-2): 13-25.

The anti-inflammation antibody has low rate of dissociation from the antibody-antigen complex, or $k_d$ (also referred to as $k_{back}$ or off-rate), preferably at most $9 \times 10^{-3}$, $8 \times 10^{-3}$, $7 \times 10^{-3}$, $6 \times 10^{-3}$, $5 \times 10^{-3}$, $4 \times 10^{-3}$, $3 \times 10^{-3}$, $2 \times 10^{-3}$, or $1 \times 10^{-3}$, (sec$^{-1}$). The anti-inflammation antibody has a affinity for its associated antigen, which may be expresses as a low dissociation constant $K_D$ of at most $9 \times 10^{-6}$, $8 \times 10^{-6}$, $7 \times 10^{-6}$, $6 \times 10^{-6}$, $5 \times 10^{-6}$, $4 \times 10^{-6}$, $3 \times 10^{-6}$, $2 \times 10^{-6}$, $1 \times 10^{-6}$, $1 \times 10^{-7}$ or $1 \times 10^{-8}$ (M).

Examples of such antibodies include those from U.S. Pat. No. 6,090,382, describing anti-TNF antibodies. Such antibodies may have one or more of the following:

CDR3L (light chain): Gln Arg Tyr Asn Arg Ala Pro Tyr Xaa, where Xaa is Thr or Ala.

CDR3H (heavy chain): Val Ser Tyr Leu Ser Thr Ala Ser Ser Leu Asp Xaa, where Xaa is Tyr or Asn.

Light chain variable region: Asp Ile Gln Met Thr Gln Ser Pro Ser Ser Leu Ser Ala Ser Val Gly Asp Arg Val Thr Ile Thr Cys Arg Ala Ser Gln Gly Ile Arg Asn Tyr Leu Ala Trp Tyr Gln Gln Lys Pro Gly Lys Ala Pro Lys Leu Leu Ile Tyr Ala Ala Ser Thr Leu Gln Ser Gly Val Pro Ser Arg Phe Ser Gly Ser Gly Ser Gly Thr Asp Phe Thr Leu Thr Ile Ser Ser Leu Gln Pro Glu Asp Val Ala Thr Tyr Tyr Cys Gln Arg Tyr Asn Arg Ala Pro Tyr Thr Phe Gly Gln Gly Thr Lys Val Glu Ile Lys.

Heavy chain variable region: Glu Val Gln Leu Val Glu Ser Gly Gly Gly Leu Val Gln Pro Gly Arg Ser Leu Arg Leu Ser Cys Ala Ala Ser Gly Phe Thr Phe Asp Asp Tyr Ala Met His Trp Val Arg Gln Ala Pro Gly Lys Gly Leu Glu Trp Val Ser Ala Ile Thr Trp Asn Ser Gly His Ile Asp Tyr Ala Asp Ser Val Glu Gly Arg Phe Thr Ile Ser Arg Asp Asn Ala Lys Asn Ser Leu Tyr Leu Gln Met Asn Ser Leu Arg Ala Glu Asp Thr Ala Val Tyr Tyr Cys Ala Lys Val Ser Tyr Leu Ser Thr Ala Ser Ser Leu Asp Tyr Trp Gly Gln Gly Thr Leu Val Thr Val Ser Ser.

Bi-specific antibodies, which are both anti-AGE antibodies and anti-inflammation antibodies, may also be used. Such antibodies will have a variable region (or complementary determining region) from those of anti-AGE antibodies, and a variable region (or complementary determining region) from anti-inflammation antibodies.

If additional antibodies are desired, they can be produced using well-known methods. For example, polyclonal antibodies (pAbs) can be raised in a mammalian host by one or more injections of an immunogen, and if desired, an adjuvant. Typically, the immunogen (and adjuvant) is injected in a mammal by a subcutaneous or intraperitoneal injection. The immunogen may be an AGE-modified protein of a cell, pro-inflammatory factor, pro-inflammatory factor receptor, or fragment thereof. Examples of adjuvants include Freund's complete, monophosphoryl Lipid A synthetic-trehalose dicorynomycolate, aluminum hydroxide (alum), heat shock proteins HSP 70 or HSP96, squalene emulsion containing monophosphoryl lipid A, α2-macroglobulin and surface active substances, including oil emulsions, pleuronic polyols, polyanions and dinitrophenol. To improve the immune response, an immunogen may be conjugated to a polypeptide that is immunogenic in the host, such as keyhole limpet hemocyanin (KLH), serum albumin, bovine thyroglobulin, cholera toxin, labile enterotoxin, silica particles or soybean trypsin inhibitor. Alternatively, pAbs may be made in chickens, producing IgY molecules.

Monoclonal antibodies (mAbs) may also be made by immunizing a host or lymphocytes from a host, harvesting the mAb-secreting (or potentially secreting) lymphocytes, fusing those lymphocytes to immortalized cells (for example, myeloma cells), and selecting those cells that secrete the desired mAb. Other techniques may be used, such as the EBV-hybridoma technique. Techniques for the generation of chimeric antibodies by splicing genes encoding the variable domains of antibodies to genes of the constant domains of human (or other animal) immunoglobulin result in "chimeric antibodies" that are substantially human (humanized) or substantially "ized" to another animal (such as cat, dog, horse, camel or alpaca, cattle, sheep, or goat) at the amino acid level. If desired, the mAbs may be purified from the culture medium or ascites fluid by conventional procedures, such as protein A-sepharose, hydroxylapatite chromatography, gel electrophoresis, dialysis, ammonium sulfate precipitation or affinity chromatography. Additionally, human monoclonal antibodies can be generated by immunization of transgenic mice containing a third copy IgG human trans-loci and silenced endogenous mouse Ig loci or using human-transgenic mice. Production of humanized monoclonal antibodies and fragments thereof can also be generated through phage display technologies.

A "pharmaceutically acceptable carrier" includes any and all solvents, dispersion media, coatings, antibacterial and antifungal agents, isotonic and absorption delaying agents, and the like, compatible with pharmaceutical administration. Preferred examples of such carriers or diluents include water, saline, Ringer's solutions and dextrose solution. Supplementary active compounds can also be incorporated into the compositions. Solutions and suspensions used for parenteral administration can include a sterile diluent, such as water for injection, saline solution, polyethylene glycols, glycerin, propylene glycol or other synthetic solvents; antibacterial agents such as benzyl alcohol or methyl parabens; antioxidants such as ascorbic acid or sodium bisulfite; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection include sterile aqueous solutions or dispersions for the extemporaneous preparation of sterile injectable solutions or dispersion. For intravenous administration, suitable carriers include physiological saline, bacteriostatic water, CREMOPHOR EL® (BASF; Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. Various antibacterial and anti-fungal agents, for example, parabens, chlorobutanol, phenol, ascorbic acid, and thimerosal, can contain microorganism contamination. Isotonic agents such as sugars, polyalcohols, such as manitol, sorbitol, and sodium chloride can be included in the composition. Compositions that can delay absorption include agents such as aluminum monostearate and gelatin. Sterile injectable solutions can be prepared by incorporating antibodies, and optionally other therapeutic components, in the required amount in an appropriate solvent with one or a combination of ingredients as required, followed by sterilization. Methods of preparation of sterile solids for the preparation of sterile injectable solutions include vacuum drying and freeze-drying to yield a solid.

For administration by inhalation, the antibodies are delivered as an aerosol spray from a nebulizer or a pressurized container that contains a suitable propellant, for example, a gas such as carbon dioxide. Antibodies may also be delivered via inhalation as a dry powder, for example using the iSPERSE™ inhaled drug deliver platform (PULMATRIX, Lexington, Mass.). The use of chicken antibodies (IgY) may be non-immunogenic in a variety of animals, including humans, when administered by inhalation.

An appropriate dosage level of each type of antibody will generally be about 0.01 to 500 mg per kg patient body weight. Preferably, the dosage level will be about 0.1 to about 250 mg/kg; more preferably about 0.5 to about 100 mg/kg. A suitable dosage level may be about 0.01 to 250 mg/kg, about 0.05 to 100 mg/kg, or about 0.1 to 50 mg/kg. Within this range the dosage may be 0.05 to 0.5, 0.5 to 5 or 5 to 50 mg/kg. Although each type of antibody may be administered on a regimen of 1 to 4 times per day, such as once or twice per day, antibodies typically have a long half-life in vivo. Accordingly, each type of antibody may be administered once a day, once a week, once every two or three weeks, once a month, or once every 60 to 90 days.

In order to determine the effectiveness of the treatment with an antibody that binds to an AGE-modified protein on a cell, either alone or in combination with an anti-inflammation antibody, or in combination with multiple anti-inflammation antibodies, or in combination with other anti-inflammation agents (for example NSAIDS and/or steroids), observation of the patient, or various tests may be used. For example, amelioration of symptoms of inflammation or autoimmune disorders may be observed in a patient (for example, a reduction in redness of the skin); blood tests for various pro-inflammatory factors (such as TNF) which show a reduction in the levels as compared to such levels prior to treatment; and tests for various pro-inflammatory factors (such as TNF) in tissue biopsies taken from at or near the site of inflammation which show a reduction in the levels as compared to such levels prior to treatment.

Unit dosage forms can be created to facilitate administration and dosage uniformity. Unit dosage form refers to physically discrete units suited as single dosages for the subject to be treated, containing a therapeutically effective quantity of one or more types of antibodies in association with the required pharmaceutical carrier. Preferably, the unit dosage form is in a sealed container and is sterile.

EXAMPLES

Example 1

In Vivo Study of the Administration of Anti-Glycation End-Product Antibody

To examine the effects of an anti-glycation end-product antibody, the antibody was administered to the aged CD1 (ICR) mouse (Charles River Laboratories), twice daily by intravenous injection, once a week, for three weeks (Days 1, 8 and 15), was followed by a 10 week treatment-free period. The test antibody was a commercially available mouse anti-glycation end-product antibody raised against carboxymethyl lysine, a common AGE epitope, conjugated with keyhole limpet hemocyanin. A control reference of physiological saline was used in the control animals.

Mice referred to a "young" were 8 weeks old, while mice referred to as "old" were 88 weeks (±2 days) old. No adverse events were noted from the administration of the antibody. The different groups of animals used in the study are shown in Table 1.

TABLE 1

| | | | | Number of Animals | |
|---|---|---|---|---|---|
| Group No. | Test Material | Mice | Dose Level (μg/gm/BID/week) | Main Study Females | Treatment-Free Females |
| 1 | Saline | young | 0 | 20 | — |
| 2 | Saline | old | 0 | 20 | 20 |
| 3 | Antibody | old | 2.5 | 20 | 20 |
| 4 | None | old | 0 | 20 | pre |
| 5 | Antibody | old | 5.0 | 20 | 20 |

— = Not Applicable,
Pre = Subset of animals euthanized prior to treatment start for collection of adipose tissue.

$P16^{INK4a}$ a marker for senescent cells, was quantified in adipose tissue of the groups by Real Time-qPCR. The results are shown in Table 2. In the table $\Delta\Delta Ct = \Delta Ct$ mean control Group (2)−$\Delta Ct$ mean experimental Group (1 or 3 or 5); Fold Expression=$2^{-\Delta\Delta Ct}$.

TABLE 2

| Calculation | Group 2 vs Group 1 | | Group 2 vs Group 3 | | Group 2 vs Group 5 | |
|---|---|---|---|---|---|---|
| (unadjusted to Group 4: 5.59) | Group 2 | Group 1 | Group 2 | Group 3 | Group 2 | Group 5 |
| Mean ΔCt | 5.79 | 7.14 | 5.79 | 6.09 | 5.79 | 7.39 |
| ΔΔCt | | −1.35 | | −0.30 | | −1.60 |
| Fold Expression | | 2.55 | | 1.23 | | 3.03 |

The table above indicates that untreated old mice (Control Group 2) express 2.55-fold more p16Ink4a mRNA than the untreated young mice (Control Group 1), as expected. This was observed when comparing Group 2 untreated old mice euthanized at end of recovery Day 85 to Group 1 untreated young mice euthanized at end of treatment Day 22. When results from Group 2 untreated old mice were compared to results from Group 3 treated old mice euthanized Day 85, it was observed that p16Ink4a mRNA was 1.23-fold higher in Group 2 than in Group 3. Therefore, the level of p16Ink4a mRNA expression was lower when the old mice were treated with 2.5 μg/gram/BID/week of antibody.

When results from Group 2 (Control) untreated old mice were compared to results from Group 5 (5 ug/gram) treated old mice euthanized Day 22, it was observed that p16Ink4a mRNA was 3.03-fold higher in Group 2 (controls) than in Group 5 (5 ug/gram). This comparison indicated that the Group 5 animals had lower levels of p16Ink4a mRNA expression when they were treated with 5.0 μg/gram/BID/week, providing p16Ink4a mRNA expression levels comparable to that of the young untreated mice (i.e. Group 1). Unlike Group 3 (2.5 ug/gram) mice that were euthanized at end of recovery Day 85, Group 5 mice were euthanized at end of treatment Day 22.

These results indicate the antibody administration resulted in the killing of senescent cells.

Example 2

Affinity and Kinetics of Test Antibody

The affinity and kinetics of the test antibody used in Example 1 were analyzed using Nα,Nα-bis(carboxymethyl)-L-lysine trifluoroacetate salt (Sigma-Aldrich, St. Louis, Mo.) as a model substrate for an AGE-modified protein of a cell. Label-free interaction analysis was carried out on a BIACORE™ T200 (GE Healthcare, Pittsburgh, Pa.), using a Series S sensor chip CM5 (GE Healthcare, Pittsburgh, Pa.), with Fc1 set as blank, and Fc2 immobilized with the test antibody (molecular weigh of 150,000 Da). The running buffer was a HBS-EP buffer (10 mM HEPES, 150 mM NaCl, 3 mM EDTA and 0.05% P-20, pH of 7.4), at a temperature of 25° C. Software was BIACORE™ T200 evaluation software, version 2.0. A double reference (Fc2-1 and only buffer injection), was used in the analysis, and the data was fitted to a Langmuir 1:1 binding model.

TABLE 3

| Experimental set-up of affinity and kinetics analysis Association and dissociation | |
|---|---|
| Flow path | Fc1 and Fc2 |
| Flow rate (μl/min.) | 30 |
| Association time (s) | 300 |

TABLE 3-continued

| Experimental set-up of affinity and kinetics analysis Association and dissociation | |
|---|---|
| Dissociation time (s) | 300 |
| Sample concentration (μM) | 20 − 5 − 1.25 (×2) − 0.3125 − 0.078 − 0 |

A graph of the response versus time is illustrated in FIG. 1. The following values were determined from the analysis: $k_a$ (1/MS)=$1.857 \times 10^3$; $k_d$ (1/s)=$6.781 \times 10^{-3}$; $K_D$ (M)=$3.651 \times 10^{-6}$; $R_{max}$ (RU)=19.52; and $Chi^2$=0.114. Because the $Chi^2$ value of the fitting is less than 10% of $R_{max}$, the fit is reliable.

Example 3 (Prophetic)

In Vivo Study of the Administration of Anti-Glycation End-Product Antibody and a Mouse Anti-Mouse TNF Antibody, in the Antigen-Induced Arthritis (AIA) Mouse Model of Rheumatoid Arthritis To examine the effects of an anti-glycation end-product antibody and a mouse anti-mouse TNF antibody on rheumatoid arthritis (a classic inflammatory disease, which is also an autoimmune disorder), both antibodies are simultaneously administered to the CD1(ICR) mouse which had been previously treated with methylated bovine serum albumin, first by systemic injection and then injection into the joint, to create AIA mice. Administration of a combination of an anti-glycation end-product antibody and anti-TNF antibody is twice daily by intravenous injection, once a week, for three weeks (Days 1, 8 and 15). The anti-glycation end-product antibody is a commercially available mouse anti-glycation end-product antibody raised against carboxymethyl lysine, a common AGE epitope, conjugated with keyhole limpet hemocyanin. A control reference of physiological saline is used in the first control animals, a second experimental group is administered only anti-glycation end-product antibody, and a second control reference of only anti-TNF antibody is used in the second control animals. Dose Levels of 5 μg/gm/BID/week of each antibody is used.

The animals are observed during the course of the study, and blood is taken to determine levels of TNF. At the end of the study, the animals are euthanized and joint tissue is examined for signs of damage associate with rheumatoid arthritis. The results indicate that the second experimental group and second control group show less joint damage and lower levels of TNF than the first control group. Furthermore, the first experimental group not only show the least joint damage and lowest level of TNF of all the study groups, but the reduction in both joint damage and levels of TNF are greater than would have been expected based solely on the second experimental group and second control group. The results demonstrate the anti-inflammatory effects of anti-glycation end-product antibodies, as well as the synergistic effects of using both an anti-glycation end-product antibody and an anti-inflammation antibody.

REFERENCES

1. Ando K, et al., "Membrane Proteins of Human Erythrocytes Are Modified by Advanced Glycation End Products During Aging in the Circulation," *Biochemical and Biophysical Research Communications*, Vol. 258, 123-27 (1999).
2. Lindsey J B, et al., "Receptor For Advanced Glycation End-Products (RAGE) and soluble RAGE (sRAGE): Cardiovascular Implications," *Diabetes Vascular Disease Research*, Vol. 6(1), 7-14, (2009).
3. Bierhaus A, "AGEs and their interaction with AGE-receptors in vascular disease and diabetes mellitus. I. The AGE concept," Cardiovasc Res, Vol. 37(3), 586-600 (1998).
4. Meuter A., et al. "Markers of cellular senescence are elevated in murine blastocysts cultured in vitro: molecular consequences of culture in atmospheric oxygen" J Assist Reprod Genet. 2014 Aug. 10. [Epub ahead of print].
5. A. Freund "Inflammatory networks during cellular senescence: causes and consequences" Trends Mol Med. 2010 May; 16(5):238-46.
6. Baker, D. J. et al., "Clearance of p16Ink4a-positive senescent cells delays ageing-associated disorders", Nature, vol. 479, pp. 232-236, (2011).
7. Jana Hadrabová, et al. "Chicken immunoglobulins for prophylaxis: Effect of inhaled antibodies on inflammatory parameters in rat airways" Journal of Applied Biomedicine (in press; Available online 5 May 2014).
8. Gianfranco Ferraccioli, et al. "Interleukin-1β and Interleukin-6 in Arthritis Animal Models: Roles in the Early Phase of Transition from Acute to Chronic Inflammation and Relevance for Human Rheumatoid Arthritis" Mol Med. 2010 November-December; 16(11-12): 552-557.

What is claimed is:

1. A composition for treating inflammation or auto-immune disorders, comprising:
   (i) an antibody that binds to an AGE-modified protein on a cell, and
   (ii) an anti-inflammation antibody, wherein the anti-inflammation antibody binds to at least one member selected from the group consisting of TNF, IL-1α, IL-1β, IL-5, IL-6, IL-8, IL-12, IL-23, CD2, CD3, CD20, CD22, CD52, CD80, CD86, C5 complement protein, BAFF, APRIL, IgE, α4β1 integrin and α4β7 integrin.

2. The composition of claim 1, wherein the antibody that binds to an AGE-modified protein on a cell is at least one member selected from the group consisting of antibodies that bind to FFI, pyrraline, AFGP, ALI, carboxymethyllysine and pentosidine.

3. The composition of claim 1, wherein:
   the antibody that binds to an AGE-modified protein on a cell is a human antibody.

4. The composition of claim 1, further comprising a pharmaceutical carrier.

5. The composition of claim 1, wherein the composition is in unit dosage form.

6. The composition of claim 1, wherein the antibody that binds to an AGE-modified protein on a cell is a conjugated antibody.

7. The composition of claim 6, wherein the conjugated antibody is an antibody that binds to an AGE-modified protein on a cell conjugated to a member selected from the group consisting of a toxin, a cytotoxic agent, magnetic nanoparticles, and magnetic spin-vortex discs.

8. The composition of claim 1, wherein the anti-inflammation antibody is a monoclonal antibody, and the antibody that binds to an AGE-modified protein on a cell is a monoclonal antibody.

9. The composition of claim 1, wherein the anti-inflammation antibody and the antibody that binds to an AGE-modified protein on a cell are both antibodies which are non-immunogenic to a species selected from the group consisting of humans, cats, dogs, horses, camels, alpaca, cattle, sheep, and goats.

10. The composition of claim 1, further comprising a pharmaceutical carrier, wherein the antibody that binds to an AGE-modified protein on a cell binds to carboxymethyllysine,
    the antibody that binds to an AGE-modified protein on a cell is a human antibody.

11. The composition of claim 1, wherein the antibody that binds to an AGE-modified protein on a cell binds to carboxymethyllysine.

12. The composition of claim 1, wherein:
    the antibody that binds to an AGE-modified protein on a cell comprises
        a first complementarity determining region comprising SEQ ID NO: 2,
        a second complementarity determining region comprising SEQ ID NO: 3,
        a third complementarity determining region comprising SEQ ID NO: 4,
        a fourth complementarity determining region comprising SEQ ID NO: 5,
        a fifth complementarity determining region comprising SEQ ID NO: 6, and
        a sixth complementarity determining region comprising SEQ ID NO: 7; and
    the anti-inflammation antibody is at least one member selected from the group consisting of abatacept, alefacept, alemtuzumab, atacicept, belimumab, canakinumab, eculizumab, epratuzumab, natalizumab, ocrelizumab, ofatumumab, omalizumab, otelixizumab, rituximab, teplizumab, vedolizumab, adalimumab, briakinumab, certolizumab pegol, etanercept, golimumab, infliximab, mepolizumab, reslizumab, tocilizumab and ustekinumab.

13. A method of treating inflammation or auto-immune disorders, comprising:
    administering an antibody that binds to an AGE-modified protein on a cell, and
    administering an anti-inflammation antibody, wherein the anti-inflammation antibody binds to at least one member selected from the group consisting of TNF, IL-1α, IL-1β, IL-5, IL-6, IL-8, IL-12, IL-23, CD2, CD3, CD20, CD22, CD52, CD80, CD86, C5 complement protein, BAFF, APRIL, IgE, α4β1 integrin and α4β7 integrin.

14. The method of claim 13, wherein the antibody that binds to an AGE-modified protein on a cell is at least one member selected from the group consisting of antibodies that bind to FFI, pyrraline, AFGP, ALI, carboxymethyllysine and pentosidine.

15. The method of claim 13, wherein the antibody that binds to an AGE-modified protein on a cell is administered as a sterile composition comprising a pharmaceutical carrier.

16. The method of claim 13, wherein the antibody that binds to an AGE-modified protein on a cell binds to carboxymethyllysine.

17. The method of claim 13, wherein:
    the antibody that binds to an AGE-modified protein on a cell comprises
        a first complementarity determining region comprising SEQ ID NO: 2,
        a second complementarity determining region comprising SEQ ID NO: 3,
        a third complementarity determining region comprising SEQ ID NO: 4,
        a fourth complementarity determining region comprising SEQ ID NO: 5,
        a fifth complementarity determining region comprising SEQ ID NO: 6, and
        a sixth complementarity determining region comprising SEQ ID NO: 7; and
    the anti-inflammation antibody is at least one member selected from the group consisting of abatacept, alefacept, alemtuzumab, atacicept, belimumab, canakinumab, eculizumab, epratuzumab, natalizumab, ocrelizumab, ofatumumab, omalizumab, otelixizumab, rituximab, teplizumab, vedolizumab, adalimumab, briakinumab, certolizumab pegol, etanercept, golimumab, infliximab, mepolizumab, reslizumab, tocilizumab and ustekinumab.

18. A composition for treating inflammation or auto-immune disorders, comprising:
    (i) an antibody that binds to an AGE-modified protein on a cell, and
    (ii) an anti-inflammation antibody, wherein the anti-inflammation antibody is at least one member selected from the group consisting of abatacept, alefacept, alemtuzumab, atacicept, belimumab, canakinumab, eculizumab, epratuzumab, natalizumab, ocrelizumab, ofatumumab, omalizumab, otelixizumab, rituximab, teplizumab, vedolizumab, adalimumab, briakinumab, certolizumab pegol, etanercept, golimumab, infliximab, mepolizumab, reslizumab, tocilizumab and ustekinumab.

19. The composition of claim 18, wherein the antibody that binds to an AGE-modified protein on a cell is at least one member selected from the group consisting of antibodies that bind to FFI, pyrraline, AFGP, ALI, carboxymethyllysine and pentosidine.

20. The composition of claim 18, wherein:
the antibody that binds to an AGE-modified protein on a cell is a human antibody.

21. The composition of claim 18, wherein the antibody that binds to an AGE-modified protein on a cell is a conjugated antibody.

22. The composition of claim 18, wherein the antibody that binds to an AGE-modified protein on a cell binds to carboxymethyllysine.

23. The composition of claim 18, further comprising a pharmaceutical carrier.

24. The composition of claim 18, wherein the anti-inflammation antibody is a monoclonal antibody, and the antibody that binds to an AGE-modified protein on a cell is a monoclonal antibody.

25. A method of treating inflammation or auto-immune disorders, comprising:
administering an antibody that binds to an AGE-modified protein on a cell, and
administering an anti-inflammation antibody, wherein the anti-inflammation antibody is at least one member selected from the group consisting of abatacept, alefacept, alemtuzumab, atacicept, belimumab, canakinumab, eculizumab, epratuzumab, natalizumab, ocrelizumab, ofatumumab, omalizumab, otelixizumab, rituximab, teplizumab, vedolizumab, adalimumab, briakinumab, certolizumab pegol, etanercept, golimumab, infliximab, mepolizumab, reslizumab, tocilizumab and ustekinumab.

26. The method of claim 25, wherein the antibody that binds to an AGE-modified protein on a cell is at least one member selected from the group consisting of antibodies that bind to FFI, pyrraline, AFGP, ALI, carboxymethyllysine and pentosidine.

27. The method of claim 25, wherein the antibody that binds to an AGE-modified protein on a cell binds to carboxymethyllysine.

28. The method of claim 25, wherein the anti-inflammatory antibody binds to TNF.

29. The method of claim 25, wherein the anti-inflammation antibody is a monoclonal antibody, and the antibody that binds to an AGE-modified protein on a cell is a monoclonal antibody.

* * * * *

SEQUENCE LISTING

<160> NUMBER OF SEQ ID NOS: 11

<210> SEQ ID NO 1
<211> LENGTH: 326
<212> TYPE: PRT
<213> ORGANISM: Artificial sequence
<220> FEATURE:
<223> OTHER INFORMATION: Human constant region

<400> SEQUENCE: 1

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

-continued

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 2
<211> LENGTH: 7
<212> TYPE: PRT
<213> ORGANISM: Artificial sequence
<220> FEATURE:
<223> OTHER INFORMATION: CDR1H (heavy chain)

<400> SEQUENCE: 2

Ser Tyr Thr Met Gly Val Ser
1               5

<210> SEQ ID NO 3
<211> LENGTH: 17
<212> TYPE: PRT
<213> ORGANISM: Artificial sequence
<220> FEATURE:
<223> OTHER INFORMATION: CDR2H (heavy chain)

<400> SEQUENCE: 3

Thr Ile Ser Ser Gly Gly Gly Ser Thr Tyr Tyr Pro Asp Ser Val Lys
1               5                   10                  15

Gly

```
<210> SEQ ID NO 4
<211> LENGTH: 10
<212> TYPE: PRT
<213> ORGANISM: Artificial sequence
<220> FEATURE:
<223> OTHER INFORMATION: CDR3H (heavy chain)
<220> FEATURE:
<221> NAME/KEY: misc_feature
<222> LOCATION: (10)..(10)
<223> OTHER INFORMATION: Xaa can be any naturally occurring amino acid

<400> SEQUENCE: 4

Gln Gly Gly Trp Leu Pro Pro Phe Ala Xaa
1               5                   10

<210> SEQ ID NO 5
<211> LENGTH: 17
<212> TYPE: PRT
<213> ORGANISM: Artificial sequence
<220> FEATURE:
<223> OTHER INFORMATION: CDR1L (light chain)

<400> SEQUENCE: 5

Arg Ala Ser Lys Ser Val Ser Thr Ser Ser Arg Gly Tyr Ser Tyr Met
1               5                   10                  15

His

<210> SEQ ID NO 6
<211> LENGTH: 7
<212> TYPE: PRT
<213> ORGANISM: Artificial sequence
<220> FEATURE:
<223> OTHER INFORMATION: CDR2L (light chain)

<400> SEQUENCE: 6

Leu Val Ser Asn Leu Glu Ser
1               5

<210> SEQ ID NO 7
<211> LENGTH: 9
<212> TYPE: PRT
<213> ORGANISM: Artificial sequence
<220> FEATURE:
<223> OTHER INFORMATION: CDR3L (light chain)

<400> SEQUENCE: 7

Gln His Ile Arg Glu Leu Thr Arg Ser
1               5

<210> SEQ ID NO 8
<211> LENGTH: 9
<212> TYPE: PRT
<213> ORGANISM: Artificial sequence
<220> FEATURE:
<223> OTHER INFORMATION: CDR3L (light chain)
<220> FEATURE:
<221> NAME/KEY: misc_feature
<222> LOCATION: (9)..(9)
<223> OTHER INFORMATION: Xaa is Thr or Ala

<400> SEQUENCE: 8

Gln Arg Tyr Asn Arg Ala Pro Tyr Xaa
1               5

<210> SEQ ID NO 9
<211> LENGTH: 12
<212> TYPE: PRT
```

```
<213> ORGANISM: Artificial sequence
<220> FEATURE:
<223> OTHER INFORMATION: CDR3H (heavy chain)
<220> FEATURE:
<221> NAME/KEY: misc_feature
<222> LOCATION: (12)..(12)
<223> OTHER INFORMATION: Xaa Xaa is Tyr or Asn

<400> SEQUENCE: 9

Val Ser Tyr Leu Ser Thr Ala Ser Ser Leu Asp Xaa
1               5                   10

<210> SEQ ID NO 10
<211> LENGTH: 107
<212> TYPE: PRT
<213> ORGANISM: Artificial sequence
<220> FEATURE:
<223> OTHER INFORMATION: Light chain variable region

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 11
<211> LENGTH: 121
<212> TYPE: PRT
<213> ORGANISM: Artificial sequence
<220> FEATURE:
<223> OTHER INFORMATION: Heavy chain variable region

<400> SEQUENCE: 11

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120
```